United States Patent
Jiang et al.

(10) Patent No.: US 11,014,895 B2
(45) Date of Patent: May 25, 2021

(54) HETEROCYCLIC UREA COMPOUND, AND DRUG COMPOSITION AND APPLICATION THEREOF

(71) Applicant: CHINA PHARMACEUTICAL UNIVERSITY, Nanjing (CN)

(72) Inventors: Sheng Jiang, Nanjing (CN); Zhengchao Tu, Nanjing (CN); Haiping Hao, Nanjing (CN); Hequan Yao, Nanjing (CN); Yatao Qiu, Nanjing (CN); Yiwu Yao, Nanjing (CN); Dong Chen, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 0 days.

(21) Appl. No.: 16/477,779

(22) PCT Filed: Jan. 1, 2018

(86) PCT No.: PCT/CN2018/072046
§ 371 (c)(1),
(2) Date: Jul. 14, 2019

(87) PCT Pub. No.: WO2018/133716
PCT Pub. Date: Jul. 26, 2018

(65) Prior Publication Data
US 2019/0367465 A1  Dec. 5, 2019

(30) Foreign Application Priority Data
Jan. 20, 2017 (CN) .......................... 201710042276.X

(51) Int. Cl.
| | | |
|---|---|---|
| *C07D 261/18* | (2006.01) | |
| *C07D 271/04* | (2006.01) | |
| *C07D 307/68* | (2006.01) | |
| *C07D 407/12* | (2006.01) | |
| *C07D 409/12* | (2006.01) | |
| *C07D 413/12* | (2006.01) | |

(52) U.S. Cl.
CPC .......... *C07D 261/18* (2013.01); *C07D 271/04* (2013.01); *C07D 307/68* (2013.01); *C07D 407/12* (2013.01); *C07D 409/12* (2013.01); *C07D 413/12* (2013.01)

(58) Field of Classification Search
CPC .. C07D 261/18; C07D 271/04; C07D 307/68; C07D 407/12; C07D 409/12; C07D 413/12
See application file for complete search history.

(56) References Cited

U.S. PATENT DOCUMENTS 8,034,953 B2 *  10/2011  Combs ................. A61K 31/541
548/125

FOREIGN PATENT DOCUMENTS

CN  106967004 A  *  7/2017

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface (Year: 2005).*
Patani et al. Chem. Rev. 1996, 96, 3147-3176 (Year: 1996).*

* cited by examiner

*Primary Examiner* — Matthew P Coughlin
(74) *Attorney, Agent, or Firm* — CBM Patent Consulting, LLC

(57) ABSTRACT

A heterocyclic urea compound, and specifically discloses an indoleamine-2,3-dioxygenase inhibitor of a heterocyclic urea compound, which solves the problems of weak curative effect and larger toxic and side effects of existing immunological therapy drugs. The invention further provides a preparation method for an indoleamine-2,3-dioxygenase inhibitor of a heterocyclic urea compound, and an application of the indoleamine-2,3-dioxygenase inhibitor of a heterocyclic urea compound or a pharmaceutically acceptable salt thereof in preparing drugs for treating or preventing tumors.

5 Claims, No Drawings

HETEROCYCLIC UREA COMPOUND, AND DRUG COMPOSITION AND APPLICATION THEREOF

TECHNICAL FIELD

The present invention relates to a heterocyclic urea compound, and more particularly, to a heterocyclic urea compound or a pharmaceutically acceptable salt or a stereoisomer and a prodrug molecule thereof, a drug composition containing the compound, and an application of the compound or the composition in preparing drugs.

BACKGROUND

Tryptophan is one of the essential amino acids in a body of a mammal, and plays an important role in a biosynthesis process of some important proteins and nicotinic acids as well as some neurotransmitters (e.g., 5-hydroxytryptamine, i.e., serotonin) in the body, thus maintaining cell activation and proliferation. The tryptophan needs to be taken in large quantities from food, and the deficiency of the tryptophan may lead to the dysfunction of some important cells.

Indoleamine-2,3-dioxygenase (IDO) is a monomeric enzyme containing heme, which was firstly found in a cell by Hayaishi group in 1967, and a cDNA encoding protein is composed of 403 amino acids with a molecular weight of 45 kDa, and is widely expressed in various mammalian tissues (Hayaishi O. et al *Science*, 1969, 164, 389-396).

The IDO is responsible for cleaning up the tryptophan in a human body, and is the first enzyme in a metabolic pathway of the invivo tryptophan and is a rate-limiting enzyme. The IDO can catalyze the tryptophan to be converted into N-formylkynurenine through oxidation reaction, and when the IDO is overexpressed, a microenvironment of deletion of the invivo tryptophan can be caused. The IDO is closely related to the pathogenesis of many diseases, and it has been proved to be a target of major diseases such as cancer, Alzheimer's disease, depression, and cataract (Swanson et al. *Am. J. Respir. Cell Mol.Biol.* 2003 30, 311) (Guillemin G. J. et al *Neuropathol. and Appl. Neurobiol.* 2005, 31, 395-404). Finding a high-efficiency inhibitor based on the IDO target has become a research hotspot in drug development in recent years.

The research has shown that the IDO can inhibit a local T cell immune response in a tumor microenvironment through the following ways: tryptophan depletion, toxic metabolism and induced regulatory T cell proliferation. In many cases, the IDO is overexpressed in tumors, thus consuming local tryptophan and generating a large number of metabolites such as kynurenine. In fact, under a culture condition of lacking the tryptophan or the kynurenine, proliferation inhibition, activity reduction and even apoptosis can occur to a T cell. However, there is a regulatory point very sensitive to a tryptophan level in the T cell, tryptophan consumption caused by the effect of the IDO can cause the T cell to stagnate in a GI phase, thus inhibiting T cell proliferation and T cell immune response. However, once the T cell proliferation is stopped, the T cell cannot be stimulated again, which is an immune mechanism of the IDO in the body (Mellor A. et al *Biochem. Biophys. Res. Commun.* 2005, 338, 20-24) (LeRond S. et al *J Exp. Med* 2002, 196, 447-457). Inhibition of IDO activity can effectively prevent the degradation of the tryptophan around a tumor cell and promote the T cell proliferation, thus enhancing the body's ability to attack the tumor cell. The IDO inhibitor can also be combined with chemotherapy drugs to reduce a drug resistance of the tumor cell, thus enhancing an anti-tumor activity of conventional cytotoxic therapy. Meanwhile, taking IDO preparation can also improve a curative effect of a therapeutic vaccine for a cancer patient. The research and development of the IDO inhibitor has become a hot field of tumor immunotherapy.

The IDO inhibitor has a broad application prospect as the drug, but no suitable IDO inhibitor has been put on the market as the drug so far, and it is of great theoretical significance and application value to find a new and efficient IDO inhibitor.

SUMMARY

A technical problem to be solved by the present invention is to provide an indoleamine-2,3-dioxygenase inhibitor of a heterocyclic urea compound aiming at the defects existing in the prior art, which is used to solve the problems of weak curative effect and large toxic and side effects of existing immunological therapy drugs.

Another technical problem to be solved by the present invention is to provide a preparation method for the indoleamine-2,3-dioxygenase inhibitor of a heterocyclic urea compound above.

Another technical problem to be solved by the present invention is to provide a pharmaceutical purpose of the indoleamine-2,3-dioxygenase inhibitor of a heterocyclic urea compound above or a pharmaceutically acceptable salt thereof.

The technical problems to be solved by the present invention are achieved by the following technical solutions.

The present invention provides a heterocyclic urea compound having a chemical structure of general formula I, or a pharmaceutically acceptable salt, an isomer, a racemate, a prodrug or a solvate thereof:

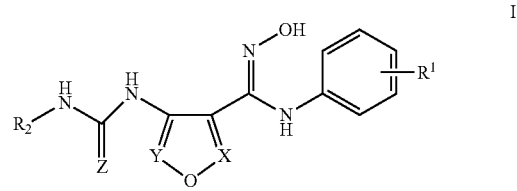

wherein,

X and Y are optionally N or C;

Z is optionally O, S, or N;

$R^1$ represents a substituent on a benzene ring, and is selected from a hydrogen, halogen, a nitro, acyano, a hydroxyl, an amino, a dimethylamino, a $C_{1-6}$ alkyl, $C_{1-6}$ perfluoroalkyl, a $C_{2-6}$ alkenyl, a $C_{2-6}$ alkynyl, a $C_{3-6}$ cycloalkyl, a $C_{3-12}$ heterocyclyl or a $C_{1-6}$ alkoxy; and a $R_2$ group is optionally selected from one of the followings:

1) a hydrogen;
2) a $C_1$-$C_{12}$ alkyl;
3) a —$CH_2$—O—$CH_2$—($C_1$-$C_{12}$ alkyl);
4) a —$CH_2$—NH—$CH_2$—($C_1$-$C_{12}$ alkyl);
5) a —$CH_2$—S—($C_1$-$C_{12}$ alkyl);
6) a $C_6$-$C_{12}$ aryl;
7) a heteroaryl;
8) a —$CH_2$—($C_6$-$C_{12}$ aryl) or a —$CH_2$-heteroaryl;
9) a $C_3$-$C_{12}$ cycloalkyl;
10) a $C_4$-$C_9$ heterocycloalkyl; and
11) a —$CH_2$—NH—$SO_2$—$NH_2$/$CH_3$($C_1$-$C_{12}$ alkyl).

Further, the $C_6$-$C_{12}$ aryl, the heteroaryl, the —$CH_2$—($C_6$-$C_{12}$ aryl) and the —$CH_2$-heteroaryl contain or do not contain one or more substituents, and the substituent is selected from the halogen, the amino, the hydroxyl, the nitro, the cyano, the $C_1$-$C_{12}$ alkyl, the $C_1$-$C_{12}$ alkoxy, a $C_1$-$C_{12}$ aminoalkyl, the $C_1$-$C_{12}$ acyl, the $C_1$-$C_{12}$ acyloxy, a $C_1$-$C_{12}$ thioalkyl, the carboxyl or a phenyl; and the $C_3$-$C_{12}$ cycloalkyl contains or does not contain one or more substituents, and the substituent is selected from the halogen, the amino, the hydroxyl, the nitro, the cyano, the $C_1$-$C_{12}$ alkyl, the $C_1$-$C_{12}$ alkoxy, the $C_1$-$C_{12}$ aminoalkyl, a $C_1$-$C_{12}$ acyl, a $C_1$-$C_{12}$ acyloxy, a $C_1$-$C_{12}$ sulfonylalkyl, the carboxyl or the phenyl.

The present invention further provides a preparation method for the heterocyclic urea compound of formula I, which comprises the following steps of:

(1) performing a chlorination reaction on a compound of formula II under an action of an acid and a chlorination reagent in an organic solvent to obtain a compound of formula III, a reaction process being as follows:

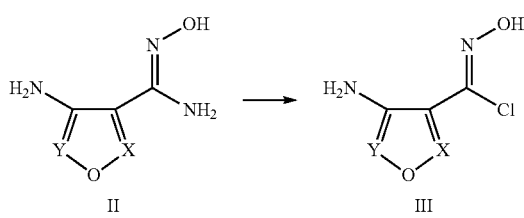

(2) reacting the compound of formula III with an aromatic amine under an action of an alkali in the organic solvent to obtain a compound of formula IV, a reaction process being as follows:

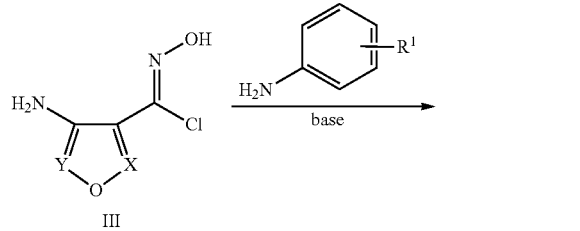

(3) reacting the compound of formula IV under an action of a carbon-based diimidazole (CDI) in the organic solvent to obtain a compound of formula V, a reaction process being as follows:

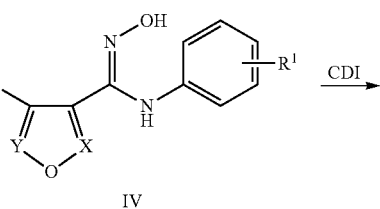

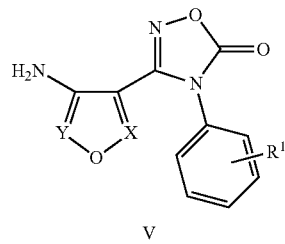

(4) reacting the compound of formula V with an isocyanate, or an isothiocyanate or an isocyanurate in the organic solvent to obtain a compound of formula VI, a reaction process being as follows:

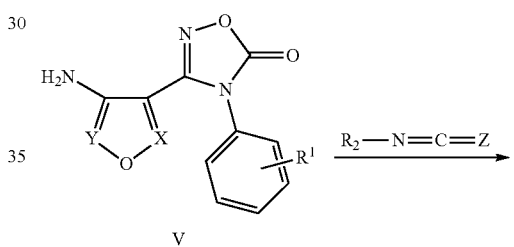

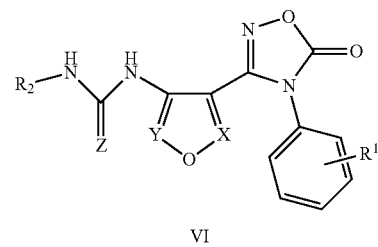

(5) deprotecting the compound of formula VI under the action of the alkali to obtain a compound of formula I, a reaction process being as follows:

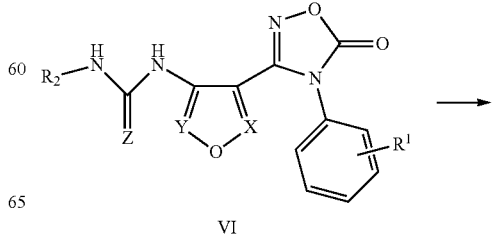

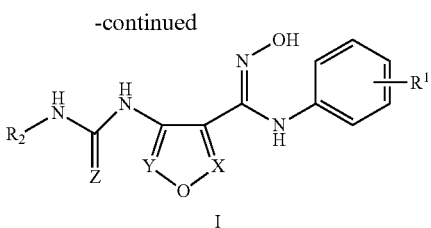

I

Further, the organic solvent is selected from one or more of a dichloromethane, a tetrahydrofuran (THF), a dimethylformamide (DMF), an ethylene glycol dimethyl ether, a 1,2-dichloroethane, a dimethyl phthalate (DMP), a methanol, an ethanol, a petroleum ether, a n-hexane and a diethyl ether.

The acid is selected from one or more of an acetic acid, a trifluoroacetic acid, a formic acid, a propionic acid, a sulfuric acid, a nitric acid and a hydrochloric acid.

The alkali is selected from one or more of a potassium carbonate, a sodium carbonate, a sodium bicarbonate, a magnesium carbonate, a calcium carbonate, a cesium carbonate, a sodium hydroxide, a potassium hydroxide, a lithium hydroxide, a cesium hydroxide, a magnesium hydroxide, an imidazole hydroxide, a triethylamine, a diisopropylethylamine, a piperidine, a dimethylpyridine, an N-methylmorpholine, a DABCO and a pyridine; and the aromatic amine is selected from one or more of an aniline, a phenethylamine, a halogen, a nitro, a cyano, a hydroxyl, an amino, a dimethylamino, a $C_{1-6}$ alkyl, a $C_{1-6}$ perfluoroalkyl, a $C_{2-6}$ alkenyl, a $C_{2-6}$ alkynyl, a $C_{3-6}$ cycloalkyl, and a $C_{3-12}$ heterocyclyl or aniline monosubstituted or polysubstituted by a $C_{1-6}$ alkoxy.

The isocyanate, the isothiocyanate or the isocyanurate is selected from a hydrogen, a $C_1$-$C_{12}$ alkyl, a —$CH_2$—O—$CH_2$—($C_1$-$C_{12}$ alkyl), a —$CH_2$—NH—$CH_2$—($C_1$-$C_{12}$ alkyl), a —$CH_2$—S—($C_1$-$C_{12}$ alkyl), a $C_6$-$C_{12}$ aryl, a heteroaryl, a —$CH_2$—($C_6$-$C_{12}$ aryl) or a —$CH_2$-heteroaryl, a $C_3$-$C_9$ cycloalkyl, a $C_4$-$C_9$ heterocycloalkyl or an isocyanate substituted by a —$CH_2$—NH—$SO_2$—$NH_2$/$CH_3$ ($C_1$-$C_{12}$ alkyl), or an isothiocyanate or an isocyanurate.

The present invention further provides an anti-tumor drug composition, which comprises the heterocyclic urea compound of general formula I, or the pharmaceutically acceptable salt, the isomer, the racemate, the prodrug or the solvate thereof, and a pharmaceutically acceptable vector.

The present invention further provides application of the heterocyclic urea compound of general formula I, and the pharmaceutically acceptable salt, or a stereoisomer or a prodrug molecule thereof in preparing drugs for treating or preventing tumors.

Further, the application is to use an effective dose of the compound to treat a lymphoma, a non-small cell lung cancer, a small cell lung cancer, a lung adenocarcinoma, a lung squamous cell carcinoma, a gastric cancer, a colon cancer, a colorectal cancer, a renal cancer, an ovarian cancer, a pancreatic cancer, a breast cancer, a prostate cancer, a liver cancer, a brain cancer, a melanoma, a multiple myeloma, a skin cancer, an epithelial cell cancer, a leukemia and cervical cancer, comprising metastatic lesions of tissues or organs far away from a primary tumor site.

In another preferred embodiment, the drugs for treating or preventing tumors comprise but are not limited to immunotherapeutic drugs for cancers containing a PD-1 antibody, a PD-L1 antibody, a PD-L2 antibody, a CTLA-4 antibody, and any other chemotherapeutic drugs or targeted therapeutic drugs.

Further, the heterocyclic urea compound and the pharmaceutically acceptable salt thereof can be used for preparing and treating tumor transitional proliferative diseases of human beings and other mammals. The heterocyclic urea compound referred to in the present invention and the pharmaceutically acceptable salt thereof can effectively inhibit the generation of kynurenine in various tumor cells, have an inhibiting effect on indoleamine-2,3-dioxygenase, and can be used for preparing anti-tumor drugs.

The heterocyclic urea compound referred to in the present invention and the pharmaceutically acceptable salt thereof can be used for treating mammalian diseases related to abnormal regulation of indoleamine-2,3-dioxygenase, comprising cancers, neurodegenerative diseases, AIDS and senile dementia.

The heterocyclic urea compound of general formula I according to the present invention or the salt thereof has an IDO inhibition effect, can be used as an effective component for treating or preventing tumors, and has the advantages of good curative effect and small toxic and side effects, and the heterocyclic urea compound of general formula I according to the present invention passes an in vitro biological activity measurement experiment.

DETAILED DESCRIPTION

In the compound of the present invention, when any variable (such as R1, R2, etc.) appears more than once in any component, the definition of the variable in each apearance is independent of definitions of the variable in other apearance. Similarly, combinations of substituents and variables are allowed as long as the combinations stabilize the compound. A line drawn from the substituent into a ring system represents that a bond specified can be connected to any annular atom that can be substituted. If the ring system is polycyclic, the bond is only connected to any suitable carbon atom adjacent to a ring. It should be understood that those of ordinary skills in the art can select the substituent and a substitution type of the compound of the present invention to provide a chemically stable raw material that can be easily obtained by the technology of the art and the methods proposed below, so as to easily synthesize a target compound. If the substituent itself is substituted with more than one group, it should be understood that these groups can be on the same carbon atom or on different carbon atoms as long as the structure is stabilized.

It should be noted that relevant terms such as "alkyl", "aryl", "heteroaryl", "halogen", "acyl", etc. used in the text are not significantly different from the terms in the art in general meaning.

For example, the term "alkyl" refers to a straight chain or a branch chain, and a $C_{1-n}$ alkyl represents a saturated aliphatic group of 1-n carbon atoms, comprising the straight chain and the branch chain, for example, a "$C_{1-12}$ alkyl" refers to that the group is the alkyl, and a number of carbon atoms on a carbon chain of the alkyl is between 1 and 12. It should be noted that when the number of carbon atoms is not particularly limited, only a number of carbon atoms of the alkyl part specified therein is referred, and a number of carbon atoms on the substituent of the alkyl is not comprised. A "cycloalkyl" refers to a monocyclic saturated aliphatic group with a specific number of carbon atoms.

For example, the "cycloalkyl" comprises a cyclopropyl, a methyl-cyclopropyl, a 2,2-dimethyl-cyclobutyl, a 2-ethyl-cyclopentyl, a cyclohexyl, etc.

The term "heteroaryl" represents a stable monocyclic ring with up to 6 atoms in the ring or a bicyclic carbocyclic ring with up to 6 atoms in each ring, wherein at least one ring is an aromatic ring and contains 1 to 4 heteroatoms selected from O, N and S. The heteroaryl in the scope of the definition comprises but is not limited to: an imidazolyl, a thiazolyl, a pyrazolyl, a furyl, a thienyl, an oxazolyl, an isoxazolyl, a pyrazinyl, a pyridazinyl, a pyrimidinyl, a pyrrolyl, and a pyridyl. The "heteroaryl" is also understood to comprise any N-oxide derivative of the heteroaryl containing nitrogen. In the case where a substituent of the heteroaryl is bicyclic and contains one ring that is non-aromatic or contains no heteroatom, it should be understood that each substituent of the heteroaryl is connected by the aromatic ring or the ring containing the heteroatom.

Those of ordinary skills in the art should know the meaning of the following terms or abbreviations.

The term "pharmaceutically acceptable salt" refers to a salt that is suitable for contact with tissues of mammals, especially human beings, without excessive toxicity, irritation, allergic reactions, etc. in a reasonable medical judgment scope and matched with a reasonable benefit/risk ratio, for example, a medically acceptable salt of an amine, a carboxylic acid and other types of compounds is well known in the art.

The term "isomer" refers to two or more compounds with the same molecular composition but different structures and properties.

The term "racemate" refers to an equimolar mixture of a chiral molecule with optical rotation and an enantiomer thereof, which is formed by equal mixing of molecules with opposite optical rotation directions and the same optical rotation capacity, and the optical rotation is cancelled out due to an interaction among these molecules, so as to be not optically rotary.

The term "solvate" refers to a mixture of a compound and a solvent, for example, a crystal is a solvate.

The term "prodrug" refers to a compound rapidly converted in vivo through hydrolysis in blood to produce a parent compound with the chemical formula above.

As understood by those skilled in the art, the "halogen" used in the text is meant to comprise chlorine, fluorine, bromine and iodine.

Unless otherwise defined, substituents of the alkyl, the cycloalkyl, the aryl, the heteroaryl and a heterocyclyl can be unsubstituted or substituted. For example, a $(C_1-C_6)$ alkyl can be substituted with one, two, or three substituents selected from an OH, a halogen, an alkoxy, a dialkylamino, or the heterocyclyl, such as a morpholinyl, a piperidyl, etc.

The present invention comprises a free form of the formula I, as well as the pharmaceutically acceptable salt and a stereoisomer. Some specific exemplary compounds in the text are protonated salts of amine compounds. The term "free form" refers to the amine compound in non-salt form. The pharmaceutically acceptable salt comprises not only an exemplary salt of a specific compound described in the text, but also typical pharmaceutically acceptable salts of all compounds of formula I in free form. The free form of specific salt of the compound can be separated using a technology known in the art. For example, the salt is processed with an appropriate alkali dilute solution such as a sodium hydroxide dilute solution, a sodium carbonate dilute solution, an ammonia dilute solution and a potassium bicarbonate dilute solution to regenerate the free form. The free forms are somewhat different from salt forms in some physical properties such as a solubility in a polar solvent, but for the invention object, the acid salt and the alkali salt are equivalent to the free forms in other pharmaceutical aspects. The pharmaceutically acceptable salt of the present invention can be synthesized from the compound of the present invention containing an alkali part or an acid part by a conventional chemical method. Generally, a salt of an alkali compound is prepared by an ion exchange chromatography or reaction of a free alkali with an inorganic or organic acid with a stoichiometric amount or an excessive amount in a required salt form in an appropriate solvent or a combination of multiple solvents. Similarly, the salt of the compound is formed by reaction with the appropriate inorganic or organic alkali. Therefore, the pharmaceutically acceptable salt of the compound of the present invention comprises a conventional non-toxic salt of the compound of the present invention formed by the reaction of the alkali compound of the present invention with the inorganic or organic acid. For example, the conventional non-toxic salt comprises a salt prepared from the inorganic acid such as a hydrochloric acid, a sulfuric acid, a hydrobromic acid, a sulfamic acid, a phosphoric acid, a nitric acid, etc., as well as a salt prepared from the organic acid such as an acetic acid, a propionic acid, a succinic acid, a glycolic acid, an acetic acid, a stearic acid, a lactic acid, a malic acid, a tartaric acid, a citric acid, an ascorbic acid, a pamoic acid, a maleic acid, a hydroxymaleic acid, a phenylacetic acid, a glutamic acid, a benzoic acid, a salicylic acid, a sulfanilic acid, a fumaric acid, a 2-acetoxyl-benzoic acid, a fumaric acid, a p-toluenesulfonic acid, a methanesulfonic acid, an ethane disulfonic acid, an oxalic acid, a hydroxyethyl sulfonic acid, a trifluoroacetic acid, etc. If the compound of the present invention is acidic, the appropriate "pharmaceutically acceptable salt" refers to a salt prepared with a pharmaceutically acceptable non-toxic alkali comprising the inorganic alkali and the organic alkali. The salt prepared from the inorganic alkali comprises an aluminum salt, an ammonium salt, a calcium salt, a copper salt, an iron salt, a ferrous salt, a lithium salt, a magnesium salt, a manganic salt, a manganous salt, a potassium salt, a sodium salt, a zinc salt, etc. For the pharmaceutically acceptable salt of the organic non-toxic alkali, the alkali comprises a salt of a primary amine, a secondary amine and a tertiary amine, a substituted amine comprises a naturally existing substituted amine, a cyclic amine and an alkaline ion exchange resin, such as arginine, sugar beet, caffeine, choline, N,N'-dibenzylethylenediamine, diethylamine, 2-diethylaminoethanol, 2-dimethylaminoethanol, aminoethanol, ethanolamine, ethylenediamine, N-ethylmorpholine, N-ethylpiperidine, sulfate glucosamine, glucosamine, methylglucosamine, histidine, lysine, isopropylamine, morpholine, piperidine, polyamine resin, procaine, purine, theobromine, triethylamine, trimethylamine, tripropylamine, trometh-amine, etc.

In one embodiment, the application provides a method for treating transitional proliferative diseases or symptoms such as tumors of human beings or other mammals using a compound having the formula (I) and a pharmaceutically acceptable salt thereof.

In one embodiment, the compound designed by the application and the pharmaceutically acceptable salt thereof can be used for treating or controlling the transitional proliferative diseases such as a lymphoma, a non-small cell lung cancer, a small cell lung cancer, a lung adenocarcinoma, a lung squamous carcinoma, a gastric cancer, a pancreatic cancer, a breast cancer, a prostate cancer, a liver cancer, a skin cancer, an epithelial cell cancer, a leukemia, a cervical cancer, etc.

In one embodiment, the compound designed by the application and the pharmaceutically acceptable salt thereof can be used together with a cytotoxin/cell inhibitor, an estrogen receptor modulator, an androgen receptor modulator, a retinoid receptor modulator, an antiproliferative, a protein transferase inhibitor, a HMG-CoA reductase inhibitor, a HIV protease inhibitor, a reverse transcriptase inhibitor, an angiogenesis inhibitor, a cell proliferation and survival signal inhibitor, a drug interfering with a cell cycle checkpoint and an apoptosis inducer, a cytotoxic drug, a tyrosine protein inhibitor, an EGFR inhibitor, a VEGFR inhibitor, a serine/threonine protein inhibitor, a Bcr-Abl inhibitor, a c-Kit inhibitor, a Met inhibitor, a Raf inhibitor, a MEK inhibitor, a MMP inhibitor, a topoisomerase inhibitor, a histone deacetylase inhibitor, a proteasome inhibitor, a CDK inhibitor, a Bcl-2 family protein inhibitor, a MDM2-2 family protein inhibitor, an IAP family protein inhibitor, a STAT family protein inhibitor, a PI3K inhibitor, an AKT inhibitor, a COX-2 inhibitor, an integrin blocker, a P53 activator, a VEGF antibody, a PD-1 antibody, a PD-L1 antibody, a PD-L2 antibody, a CTLA-4 antibody, an EGF antibody and other drugs currently applied or in the development stage to increase a clinical effect.

The compound referred to in the application and the pharmaceutically acceptable salt thereof can be used to treat the following diseases and other diseases not listed below according to the following methods:

1) a method for treating a breast cancer of human beings or other mammals using a pharmaceutical composition comprising the compound that is referred to in the application and has a structure of formula (I) and the pharmaceutically acceptable salt thereof, comprising but being not limited to an invasive ductal carcinoma, an invasive lobular carcinoma, an in-situ ductal carcinoma, and an in-situ lobular carcinoma;

2) a method for treating a respiratory cancer of human beings or other mammals using the pharmaceutical composition comprising the compound that is referred to in the application and has the structure of formula (I) and the pharmaceutically acceptable salt thereof, comprising but being not limited to a small cell & non-small cell lung cancer, a bronchial adenocarcinoma and a pleuropulmonary blastoma;

3) a method for treating a brain cancer of human beings or other mammals using the pharmaceutical composition comprising the compound that is referred to in the application and has the structure of formula (I) and the pharmaceutically acceptable salt thereof, comprising but being not limited to a brain stem glioma and an immediate glioma, a cerebellum astrocytoma and a cerebral astrocytoma, an ependymoma, and a neuroectodermal tumor and a pinealoma;

4) a method for treating a tumor of female and male reproductive organs of human beings or other mammals using the pharmaceutical composition comprising the compound that is referred to in the application and has the structure of formula (I) and the pharmaceutically acceptable salt thereof, the tumor of male reproductive organ comprising but being not limited to a prostate cancer and a testicular cancer, and the tumor of female reproductive organ comprising but being not limited to a cervical cancer, an endometrial cancer, an ovarian cancer, a vaginal cancer and a vulvar cancer, and an intrauterine tumor;

5) a method for treating a gastrointestinal cancer of human beings or other mammals using the pharmaceutical composition comprising the compound that is referred to in the application and has the structure of formula (I) and the pharmaceutically acceptable salt thereof, comprising but being not limited to an anal cancer, a colon cancer, a colorectal cancer, an esophageal cancer, a gastric cancer, a pancreatic cancer, a rectal cancer, a small intestinal cancer and a salivary gland cancer;

6) a method for treating an urethral carcinoma of human beings or other mammals using the pharmaceutical composition comprising the compound that is referred to in the application and has the structure of formula (I) and the pharmaceutically acceptable salt thereof, comprising but being not limited to a bladder cancer, a penis cancer, a kidney cancer, a renal pelvis cancer, an ureter cancer and an urethral carcinoma;

7) a method for treating a cancer eye of human beings or other mammals using the pharmaceutical composition comprising the compound that is referred to in the application and has the structure of formula (I) and the pharmaceutically acceptable salt thereof, comprising but being not limited to an intraocular melanoma and a retinoblastoma;

8) a method for treating a liver cancer of human beings or other mammals using the pharmaceutical composition comprising the compound that is referred to in the application and has the structure of formula (I) and the pharmaceutically acceptable salt thereof, comprising but being not limited to a hepatocellular carcinoma (hepatocellular carcinoma with or without a fiberboard change), a cholangiocarcinoma (intrahepatic cholangiocarcinoma) and a mixed hepatocellular cholangiocarcinoma;

9) a method for treating a skin cancer of human beings or other mammals using the pharmaceutical composition comprising the compound that is referred to in the application and has the structure of formula (I) and the pharmaceutically acceptable salt thereof, comprising but being not limited to a flat cell carcinoma, a Kaposi's sarcoma, a malignant melanoma, a Merck's cell skin cancer and a non-melanoma cell carcinoma;

10) a method for treating a head and neck cancer of human beings or other mammals using the pharmaceutical composition comprising the compound that is referred to in the application and has the structure of formula (I) and the pharmaceutically acceptable salt thereof, comprising but being not limited to a laryngeal cancer, a hypopharyngeal cancer, a nasopharynx cancer, an oropharyngeal cancer, and a lip cancer and oral cancer;

11) a method for treating a lymphoma of human beings or other mammals using the pharmaceutical composition comprising the compound that is referred to in the application and has the structure of formula (I) and the pharmaceutically acceptable salt thereof, comprising but being not limited to an AIDS-related lymphoma, a non-Hodgkin lymphoma, a cutaneous T-cell lymphoma, a systemic T-cell lymphoma, a Hodgkin lymphoma and a central nervous system lymphoma;

12) a method for treating a sarcoma of human beings or other mammals using the pharmaceutical composition comprising the compound that is referred to in the application and has the structure of formula (I) and the pharmaceutically acceptable salt thereof, comprising but being not limited to a soft tissue sarcoma, an osteosarcoma, a malignant fibrous histiocytoma, a lymphosarcoma and a rhabdomyosarcoma; and 13) a method for treating a leukemia of human beings or other mammals using the pharmaceutical composition comprising the compound that is referred to in the application and has the structure of formula (I) and the pharmaceutically acceptable salt thereof, comprising but being not limited to an acute myeloid leukemia, an acute lymphoblastic leukemia, a chronic lymphoblastic leukemia, a chronic myeloid leukemia and a polychaete leukemia.

Administration Method and Dosage Range

According to a standard pharmaceutical technology, the compound of the present invention can be administered to the mammals and preferably human beings separately or in combination with a pharmaceutically acceptable receptor, an excipient or a diluent in the pharmaceutical composition. The compound can be administered orally or subcutaneously, intramuscularly, intraperitoneally, intravenously, rectally and locally, and parenterally, or by eyes, lungs and nasal cavities.

In one embodiment, when the compound of formula (I) is used to treat or control cancer patients, a dosage range is 0.1 to 500 mg/day per kg of body weight orally. An appropriate administration method is single-dose administration per day, multiple administration for twice, three times, four times per day, or administration by a slow release technology. For large mammals, a preferred dosage range is 0.1 to 1500 mg/day/kg per kg of body weight. For patients with an average weight of 70 kg, the dose is 1 mg to 500 mg. For some particularly highly active compounds, the daily dose for adult patients can be as low as 0.1 mg/day.

In one embodiment, when the compound of formula (I) is used to treat or control cancer patients, a dosage range is 0.1 to 500 mg/day/per kg of body weight intravenously. An appropriate administration method is single-dose administration per day, multiple administration for twice, three times, four times per day, or administration by a slow release technology. For large mammals, a preferred dosage range is 0.1 to 1500 mg/day per kg of body weight. For patients with an average weight of 70 kg, the dose is 1 mg to 500 mg. For some particularly highly active compounds, the daily dose for adult patients can be as low as 0.1 mg/day.

Dosage Form

The pharmaceutical composition containing an active ingredient of the present invention can be prepared into a form suitable for oral administration, such as a tablet, a buccal tablet, a lozenge, a water or oil suspension, dispersible powder or granule, an emulsion, a hard capsule or a soft capsule, or a syrup or a tincture. A composition intended for oral administration can be prepared according to any known method in the field of pharmaceutical composition manufacturing, and in order to provide a pharmaceutically refined and palatable preparation, the composition can contain one or more agents selected from a sweetening agent, a flavoring agent, a coloring agent and a preservative.

The tablet contains an active ingredient and a non-toxic pharmaceutically acceptable excipient suitable for manufacturing the tablet. These excipients can be, for example, inert diluents such as calcium carbonate, sodium carbonate, lactose, calcium phosphate or sodium phosphate; granulating agents and disintegrating agents such as microcrystalline cellulose, croscarmellose sodium, corn starch or alginic acid; binders such as starch, gelatin, polyvinylpyrrolidone or acacia; and lubricants such as magnesium stearate, stearic acid or talc. The tablet can be uncoated or coated by a known technology to cover a bad taste of the drug or prolong disintegration and absorption of the drug in a gastrointestinal tract, thus providing a drug effect that lasts longer. For example, a raw material with the taste capable of being covered by water solubility such as hydroxypropyl-methyl cellulose or hydroxypropyl cellulose can be used, or a delayed raw material such as ethyl cellulose and cellulose acetate butyrate can be used. A tablet dosage form can be 0.1 mg/tablet, 0.2 mg/tablet, 0.25 mg/tablet, 0.5 mg/tablet, 1 mg/tablet, 2 mg/tablet, 5 mg/tablet, 10 mg/tablet, 25 mg/tablet, 50 mg/tablet, 100 mg/tablet, and 250 mg/tablet. Other dosage forms such as a capsule can be used as reference for similar dosage.

An oral preparation can also be made into a hard gelatin capsule, wherein the active ingredient is mixed into an inactive solid diluent such as calcium carbonate, sodium carbonate or kaolin; or made into a soft gelatin capsule, wherein the active ingredient is mixed into a water soluble vector such as polyvinyl glycol or oil medium, such as peanut oil, liquid paraffin or olive oil. A water suspension contains an active material mixed with the excipient suitable for preparing the water suspension. The excipient is a suspending agent such as carboxymethylcellulose odium, methylcellulose, hydroxypropyl-methylcellulose, sodium alginate, polyvinylpyrrolidone, or Arabic gum; the water suspension can also contain one or more preservatives such as ethyl p-hydroxybenzoate or n-propyl p-hydroxybenzoate, one or more coloring agents, one or more flavoring agents, and one or more sweetening agents such as sucrose, saccharin or aspartame. The oil suspension can be prepared through suspending the active ingredient in vegetable oil such as peanut oil, sesame oil, coconut oil, or olive oil, and mineral oil such as liquid paraffin. The oil suspension can contain a thickening agent such as beeswax, paraffin wax or cetyl alcohol.

The sweetening agent and the flavoring agent described above can be added to provide the preparation suitable for oral administration. These compositions can be stored by adding an antioxidant such as butylated hydroxyanisole or tocopherol.

Dispersible powder or granule is suitable for preparing the water suspension by adding water to provide the active ingredient mixed with a dispersing or wetting agent, the suspending agent and one or more preservatives. Appropriate dispersing agent or wetting agent and the suspending agent have been described by the examples mentioned above. Other excipients such as the sweetening agent, the flavoring agent and the coloring agent can also be present. These compositions can be stored by adding the antioxidant such as ascorbic acid.

The composition of the present invention can be made in the form of an oil-in-water emulsion. The oil phase can be the vegetable oil such as peanut oil or olive oil, or the mineral oil such as liquid paraffin or a mixture thereof. An appropriate emulsifying agent can be a naturally existing phospholipid such as soybean lecithin and ester or partial ester obtained from a mixture of fatty acid and hexitol anhydride such as dehydrated sorbitol monooleat and a condensation product of the partial ester and alkylene oxide such as polyoxyethylene dehydrated sorbitol monooleat. The emulsion can also contain the sweetening agent, the flavoring agent, the antioxidant and the preservative.

The syrup and the tincture can be prepared with the sweetening agent such as glycerol, propylene glycol, sorbitol, or sucrose. The preparation can also contain the wetting agent, the flavoring agent, the coloring agent, the antioxidant and the preservative.

The composition of the present invention can be made into sterile injectable solution. Water, a Ringer's solution and an isotonic sodium chloride solution can be used in the acceptable vector and the solvent.

The sterile injection can also be made into a sterile injectable oil-in-water microemulsion in which the active ingredient is dissolved in the oil phase. For example, the active ingredient is firstly dissolved in a mixture of soybean oil and lecithin, and then the oil solution is put into a mixture of water and glycerol, and processed to prepare the microemulsion.

The pharmaceutical composition can be made into the sterile injectable solution or the oil suspension for intramuscular or subcutaneous administration. The suspension can be prepared with the dispersing agent or the wetting agent and the suspending agent mentioned above according to the known technology. The sterile injectable preparation can also be made into the sterile injectable solution or the suspension in a non-toxic parenterally acceptable diluent or solvent, such as a solution in 1,3-butanediol. In addition, non-volatile oil is conventionally used as a solvent or a suspension medium. For this purpose, any non-irritating non-volatile oil can be used comprising synthetic monoglyceride or diglyceride. In addition, the fatty acid such as oleic acid has been found to be used in the injectable preparation.

Drug Metabolite and Prodrug

Metabolites of the compound referred to in the application and the pharmaceutically acceptable salt thereof, as well as the prodrugs that can be converted into structures of the compound referred to in the application and the pharmaceutically acceptable salt thereof in vivo are also included in the patent requirements of the application.

The compound of formula (I) can be used in combination with other drugs known to treat or improve similar symptoms. In the case of combined administration, the original drug administration method and dose are unchanged while the compound of formula (I) is administered simultaneously or subsequently. When the compound of formula I is administered simultaneously with one or more other drugs, the pharmaceutical composition containing one or more known drugs and the compound of formula (I) is preferably used. Drug combination also comprises administering the compound of formula (I) and one or more other known drugs in overlapping time periods. When the compound of formula (I) is combined with one or more other drugs, the dose of the compound of formula (I) or the known drug may be lower than the dose while being used separately.

The drug or the active ingredient that can be used in combination with the compound of formula I comprises but is not limited to: a cytotoxin/cell inhibitor, an estrogen receptor modulator, an androgen receptor modulator, a retinoid receptor modulator, an antiproliferative, a protein transferase inhibitor, a HMG-CoA reductase inhibitor, a HIV protease inhibitor, a reverse transcriptase inhibitor, an angiogenesis inhibitor, a cell proliferation and survival signal inhibitor, a drug interfering with a cell cycle checkpoint and an apoptosis inducer, a cytotoxic drug, a tyrosine protein inhibitor, an EGFR inhibitor, a VEGFR inhibitor, a serine/threonine protein inhibitor, a Bcr-Abl inhibitor, a c-Kit inhibitor, a Met inhibitor, a Raf inhibitor, a MEK inhibitor, a MMP inhibitor, a topoisomerase inhibitor, a histone deacetylase inhibitor, a proteasome inhibitor, a CDK inhibitor, a Bcl-2 family protein inhibitor, a MDM2-2 family protein inhibitor, an IAP family protein inhibitor, a STAT family protein inhibitor, a PI3K inhibitor, an AKT inhibitor, a COX-2 inhibitor, an integrin blocker, a P53 activator, a VEGF antibody, a PD-1 antibody, a PD-L1 antibody, a PD-L2 antibody, a CTLA-4 antibody, an EGF antibody, etc.

In one embodiment, the drug that can be used in combination with the compound of formula (I) comprises but is not limited to: aldesleukin, alendronic acid, interferon, alitretinoin, allopurinol, allopurinol sodium, palonosetron hydrochloride, altratamine, aminoglutamide, amifostine, amrubicin, amsacrine, anastrozole, dolasetron, aranesp, arglabin, arsenic trioxide, anoxin, 5-azacytidine, azathioprine, BCG Vaccine, betadine, betamethasone acetate, betamethasone sodium phosphate, bexarotene, bleomycin sulfate, bromogeramine, bortezomib, busulfan, calcitonin, alemtuzumab injection, capecitabine, carboplatin, cisplatin, Casodex, cefesone, celmoleukin, daunorubicin, chlorambucil, cladribine, clodronic acid, cyclophosphamide, Ara-C, dacarbazine, actinomycin D, liposomal daunorubicin, dexamethasone, dexamethasone phosphate, estradiol valerate, denileukin diftitox 2, deslorelin, dexrazoxane, diethylstilbestrol, diflucan, docetaxel, doxifluridine, doxorubicin, dronabinol, chitosan complex, rasburicase, epirubicin hydrochloride, aprepitant, epirubicin, epoetin alfa, erythropoietin, eptaplatin, levamisole tablet, estradiol preparation, 17-β-estradiol, estramustine sodium phosphate, ethinylestradiol, hydroxyl phosphate, etopophos, etoposide, fadrozole, tamoxifen preparation, filgrastim, filletidine, fluorouridine, fluconazole, fludarabine, 5-fluorodeoxyuridine phosphate, 5-fluorouracil, fluoxymesterone, flutamide, fumestan, 1-β-D-arabinofuranoside-5'-stearyl phosphate, fotemustine, fulvestrant, gamma globulin, gemcitabine, gemtuzumab ozogamicin, imatinib, carmustine rice paper capsule, goserelin, granisetron hydrochloride, histrelin, hycamtin, hydrocortisone, erythro-hydroxynonyladenine, hydroxyurea, ibritumomab tiuxetan, idarubicin, isophosphamide, interferon α, interferon α2, interferon α-2A, interferon α-2B, interferon α-n1, interferon α-n3, interferon β, interferon γ-1a, interleukin-2, intron A, irisha, irinotecan kytril, lentinan sulfate, letrozole, leucovorin, leuprorelin, leuprorelin acetate, levamisole, calcium levofolinate, sodium levothyroxine, sodium levothyroxine preparation, lomustine, lonidamine, dronabinol, mecobalamin, medroxyprogesterone acetate, megestrol acetate, melphalan, esterified estrogen, 6-mercaptopurine, mesna, methotrexate, aminolevulinic acid ester, miltefosine, minocycline, mitomycin C, mitotane, mitoxantrone, trilostane, adriamycin citrate liposome, nedaplatin, pegfilgrastim, oprelvekin, neupogen, nilutamide, tamoxifen, NSC-631570, recombinant human interleukin 1-β, octreotide, ondansetron hydrochloride, prednisolone oral liquid, oxaliplatin, paclitaxel, docetaxel, cabazitaxel, prednisolone sodium phosphate, pegaspargase, pegasys, pentostatin, picibanil preparation, pilocarpine hydrochloride, pirarubicin, mithramycin, porfimer sodium, prednimustine, prednisone, prednisolone steaglate, premarin, procarbazine, recombinant human erythropoietin, raltitrexed, Rebif, etidronate rhenium-186, mabthera, redoxon-A, romurtide, pilocarpine hydrochloride tablet, sargramostim, semustine, sizofiran, obuzoxane, solumedrol, spar-fosic acid, streptozocin, strontium chloride-89, levothyroxine sodium, tamoxifen, tamsulosin, tasolnamine, tastolactone, taxotere, teceleukin, temozolomide, teniposide, testosterone propionate, methyltestosterone, thioguanine, thiotepa, thyroid stimulating hormone, tiludronate, topotecan, toremifene, tositumomab, trastuzumab, treosulfan, tretinoin, methotrexate tablet, melamine, trimetrexate, triptorelin acetate, triptorelin pamoate, UFT, uridine, valrubicin, vesnarinone, vinblastine, vincristine, vindesine, vinorelbine, virulizin, dextrazoxane, zinostatin stimalamer, ondansetron, paclitaxel protein stabilizer, acolbifene, affinitak, aminopterin, arzoxifene, asoprisnil, atamestane, atrasentan, avastin, CCI-779, CDC-501, celecoxib, cetuximab, crisnatol, cyclprogestin acetate, gemcitabine, adriamycin-MTC, ibandronic acid, lanreotide, lasofoxifene, mipoxifene, mino kojic acidester, liposome MTP-PE, nafarelin, nolatrexed, paclitaxel polyglutamate, seocalcitol, erlotinib, paclitaxel liposome, tipifarnib, SAHA, tirapazamine, vapreotide, vatalanib, verteporfin, vinflunine, or combinations thereof.

In order to better describe the technical content of the present invention, the present invention is further described below with reference to detailed embodiments, but the embodiments are not intended to limit the protection scope of the present invention.

It should be noted that in the following embodiments, the conventional post-treatment method is as follows: after the reaction is completed, an appropriate amount of water is added to a reaction solution to separate an organic phase and a water phase, and combine the organic phases; and if necessary, drying is performed with 5% HCl solution and/or saturated Na2SO4 in sequence, decompression and drying are performed after filtering to obtain a crude product, and a final product is obtained after column chromatography purification.

Embodiment 1

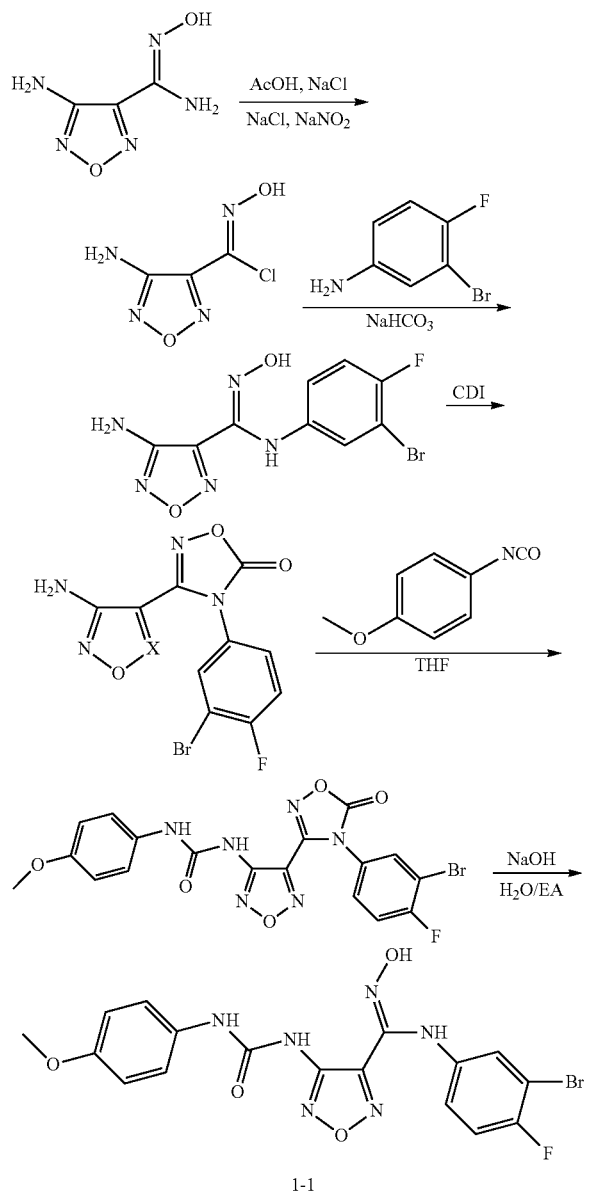

1-1

Step 1. (Z)-4-amino-N'-hydroxy-N-(3-bromo-4-fluorophenyl)-1,2,5-oxadiazole-3-formamidine

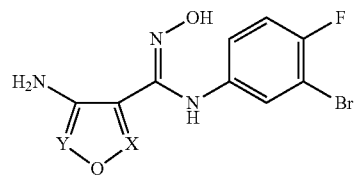

Acetic acid (5 mL), hydrochloric acid (4N) (5 mL), and an aqueous solution (5 ml) of NaNO$_2$ (2.42 g, 34.96 mmol) were added into a raw material (5 g, 34.96 mmol) at 0° C. in sequence, then the mixture was heated to a room temperature to react for 18 h, added with ethyl acetate (25 mL) and laminationed, an aqueous phase was extracted with ethyl acetate (2*25 ml), and then an organic phase was combined, washed with saturated brine (25 ml), dried with anhydrous sodium sulfate, and concentrated to obtain an intermediate (4.5 g). Under the protection of argon, an aqueous solution (20 ml) of NaHCO$_3$ (7.8 g, 93.0 mmol) was added into an aqueous solution of the intermediate (4.5 g) and 3-bromo-4-fluoroaniline (11.8 g, 62.0 mmol) in methanol (20 ml) to react for 12 h at 50° C., then the mixture was concentrated after a TLC detection showed that the reaction was complete, added with ethyl acetate (20 ml) and laminationed, an aqueous phase was extracted with ethyl acetate (2*20 mL), and then an organic phase was combined, washed with saturated brine (20 mL), dried with anhydrous sodium sulfate, concentrated, and subjected to column chromatography to obtain a compound target (7.32 g, 75%). $^1$H NMR (400 MHz, DMSO): δ 8.08 (dd, J=3.6, 2.4 Hz, 1H), 7.71 (m, 1H), 7.60 (t, J=8.8 Hz, 1H), 6.59 (s, 2H) ppm.

Step 2. 3-(4-amino-1,2,5-oxadiazole-3-substituted)-4-(3-bromo-4-fluorophenyl)-1,2,4-oxadiazole-5(4H) carbonyl

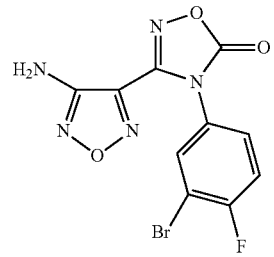 [SMILES: Nc1nonc1-c1noc(=O)n1-c1ccc(F)c(Br)c1]

CDI (8.0 g, 36.3 mmol) was added into an ethyl acetate solution (10 mL) of a raw material (3.8 g, 12.1 mmol), then the mixture was heated to 70° C. to react for 5 h, added with water (20 ml) and laminationed after a TLC detection showed that the reaction was complete, an aqueous phase was extracted with ethyl acetate (2*20 mL), and then an organic phase was combined, washed with saturated brine (10 ml), dried with anhydrous sodium sulfate, concentrated, and subjected to column chromatography to obtain a compound (3.3 g, 81%). $^1$H NMR (400 MHz, DMSO): δ 11.42 (s, 1H), 8.85 (s, 1H), 7.18 (t, J=8.8 Hz, 1H), 7.10 (dd, J=3.2 and 2.8 Hz 1H), 6.76 (m, 1H), 6.24 (s, 2H) ppm.

Step 3. 1-(4-(4-(3-bromo-4-fluorophenyl)-5-carbonyl-4,5-dihydro-1,2,4-oxadiazole-3-substituted)-1,2,5-oxadiazole-3-substituted)-3-(4-methoxyphenyl)urea

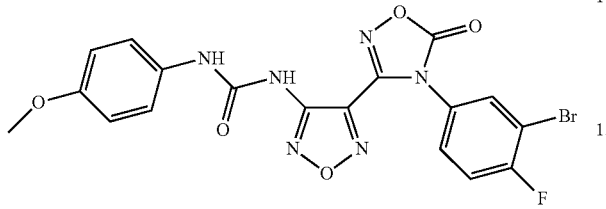

Under the protection of argon at 0° C., a tetrahydrofuran solution (1 mL) of p-methoxybenzene isocyanide (14.4 mg, 0.0965 mmol) was dropwise added into a tetrahydrofuran solution (1 mL) of a raw material (30 mg, 0.0877 mmol) slowly, then the mixture was heated to a room temperature to react for 16 h, concentrated, added with water (1 mL), then added with ethyl acetate (1 mL) and laminationed, an aqueous phase was extracted with ethyl acetate (2*2 mL), and then an organic phase was combined, washed with saturated saline (2 mL), dried with anhydrous sodium sulfate, concentrated, and subjected to column chromatography to obtain a target object (24.92 mg, 58%). MS (EI, m/z): 492 (M$^+$+1).

Step 4. (Z)-1-(4-(N-(3-bromo-4-fluorophenyl)-N'-hydroxyaminoiminomethyl)-1,2,5-oxadiazole-3-substituted)-3-(4-methoxyphenyl)urea 1-1

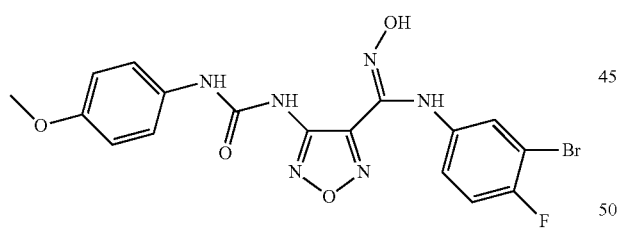

The above raw material (20 mg) was dissolved in ethyl acetate (1 mL), and added with an aqueous solution (0.2 mL, 2M) of NaOH to react for 5 h, added with water (1 mL), and laminationed with ethyl acetate (5 mL), an aqueous phase was extracted with ethyl acetate (2*5 mL), and then an organic phase was combined, washed with saturated saline (2 mL), dried with anhydrous sodium sulfate, concentrated, and subjected to column chromatography to obtain a target compound 1-1 (16.7 mg, 88%). $^1$H NMR (400 MHz, DMSO): δ 11.44 (s, 1H), 8.85 (s, 1H), 7.18 (t, J=8.8 Hz, 1H), 7.10 (m, 1H), 6.78 (m, 1H), 6.25 (s, 1H), 3.57 (m, 1H), 1.85-1.81 (m, 2H), 1.63-1.59 (m, 2H), 1.46-1.19 (m, 4H) ppm. $^{13}$C NMR (125 MHz, DMSO): δ 162.1, 158.1, 154.1, 150.2, 148.3, 139.5, 133.6, 130.6, 120.1, 119.6, 119.1, 118.9, 114.9, 113.6, 54.6 ppm. MS (EI, m/z): 466 (M$^+$+1).

Embodiment 2

(Z)-1-(4-(N-(3-bromo-4-fluorophenyl)-N'-hydroxyaminoiminomethyl)-1,2,5-oxadiazole-3-substituted)-3-(3-ethylphenyl)urea 1-2

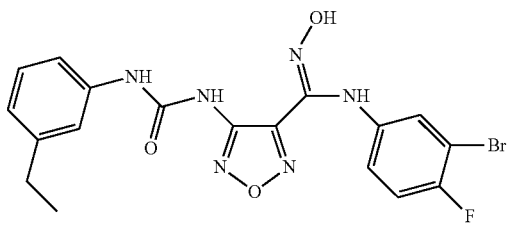 [SMILES: COc1ccccc1NC(=O)Nc1nonc1/C(=N/O)Nc1ccc(F)c(Br)c1]

The synthesis method was the same as that in Embodiment 1.

$^1$H NMR (400 MHz, DMSO): δ 11.43 (s, 1H), 8.85 (s, 1H), 7.37-7.36 (m, 2H), 7.18-7.16 (m, 2H), 7.12-7.09 (m, 1H), 6.79-6.59 (m, 2H), 6.25 (s, 1H), 6.11 (s, 1H), 3.76 (s, 3H) ppm. $^{13}$C NMR (125 MHz, DMSO): δ 163.4, 159.1, 155.1, 151.3, 146.2, 139.9, 136.2, 133.9, 129.8, 121.1, 119.9, 119.1, 116.1, 115.7, 113.1, 110.1, 54.2 ppm. MS (EI, m/z): 465 (M$^+$+1).

Embodiment 3

(Z)-1-(4-(N-(3-bromo-4-fluorophenyl)-N'-hydroxyaminoiminomethyl)-1,2,5-oxadiazole-3-substituted)-3-(2-methoxyphenyl)urea

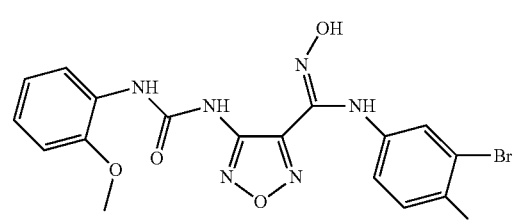

The synthesis method was the same as that in Embodiment 1.

$^1$H NMR (400 MHz, DMSO): δ 11.45 (s, 1H), 8.81 (s, 1H), 7.85 (d, J=8.4 Hz, 1H), 7.19-7.12 (m, 2H), 7.14-7.02 (m, 4H), 6.74-6.53 (m, 2H), 6.21 (s, 1H), 6.07 (s, 1H), 3.72 (s, 3H) ppm. $^{13}$C NMR (125 MHz, DMSO): δ 163.1, 155.6, 151.1, 149.1, 147.8, 139.8, 136.8, 128.9, 124.1, 121.1, 120.5, 119.5, 118.6, 118.1, 115.9, 112.1, 55.1 ppm. MS (EI, m/z): 465 (M$^+$+1).

Embodiment 4

(Z)-1-(4-(N-(3-bromo-4-fluorophenyl)-N'-hydroxyaminoiminomethyl)-1,2,5-oxadiazole-3-substituted)-3-p-methylphenyl)urea

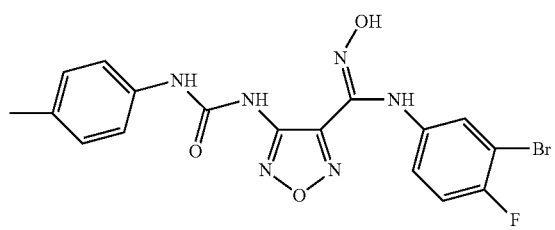 [SMILES: Cc1ccc(NC(=O)Nc2nonc2/C(=N/O)Nc2ccc(F)c(Br)c2)cc1]

The synthesis method was the same as that in Embodiment 1.

¹H NMR (400 MHz, DMSO): δ 11.46 (s, 1H), 8.88 (s, 1H), 7.57 (d, J=8.8 Hz, 2H), 7.25 (d, J=8.8 Hz, 2H), 7.21 (t, J=8.8 Hz, 1H), 7.11-7.07 (m, 1H), 6.77-6.52 (m, 1H), 6.21 (s, 1H), 6.10 (s, 1H), 2.36 (s, 1H) ppm. ¹³C NMR (125 MHz, DMSO): δ 162.5, 154.1, 151.1, 147.2, 140.3, 136.5, 134.6, 139.6, 120.9, 119.6, 119.31, 118.7, 114.2, 21.6 ppm. MS (EI, m/z): 449 (M⁺+1).

Embodiment 5

(Z)-1-(4-(N-(4-bromo-3-fluorophenyl)-N'-hydroxyaminoiminomethyl)-1,2,5-oxadiazole-3-substituted)-3-(4-fluorophenyl)urea

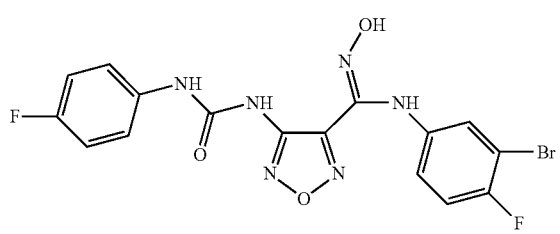 [SMILES: O=C(Nc1ccc(F)cc1)Nc1nonc1/C(=N/O)Nc1ccc(F)c(Br)c1]

The synthesis method was the same as that in Embodiment 1.

¹H NMR (400 MHz, DMSO): δ 11.40 (s, 1H), 8.82 (s, 1H), 7.59 (d, J=6.6 Hz, 2H), 7.20 (d, J=6.6 Hz, 2H), 7.13 (t, J=8.8 Hz, 1H), 7.20-7.05 (m, 1H), 6.71-6.52 (m, 1H), 6.21 (s, 1H), 6.03 (s, 1H) ppm. ¹³C NMR (125 MHz, DMSO): δ 163.8, 160.1, 154.1, 151.5, 148.1, 140.5, 135.2, 134.9, 121.8, 120.9, 119.1, 118.6, 115.9, 114.8 ppm. MS (EI, m/z): 453 (M⁺+1).

Embodiment 6

(Z)-1-(4-(N-(3-bromo-4-fluorophenyl)-N'-hydroxyaminoiminomethyl)-1,2,5-oxadiazole-3-substituted)-3-(4-trifluorotolyl)urea The synthesis method was the same as that in Embodiment 1.

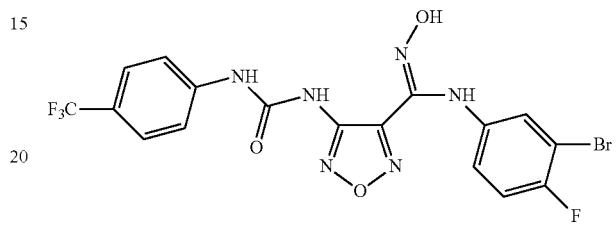

¹H NMR (400 MHz, DMSO): δ 11.43 (s, 1H), 8.85 (s, 1H), 7.60 (d, J=6.6 Hz, 2H), 7.25 (d, J=6.6 Hz, 2H), 7.16 (t, J=8.8 Hz, 1H), 7.20-7.06 (m, 1H), 6.73-6.55 (m, 1H), 6.23 (s, 1H), 6.06 (s, 1H) ppm. ¹³C NMR (125 MHz, DMSO): δ 163.9, 160.1, 154.3, 151.5, 148.1, 140.7, 135.3, 121.8, 120.9, 119.3, 118.8, 115.9, 114.9 ppm. MS (EI, m/z): 504 (M⁺+1).

Embodiment 7

(Z)-1-(4-(N-(3-bromo-4-fluorophenyl)-N'-hydroxyaminoiminomethyl)-1,2,5-oxadiazole-3-substituted)-3-cyclohexylurea

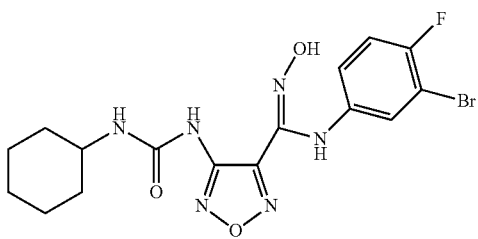 [SMILES: O=C(Nc1nonc1/C(=N/O)Nc1ccc(F)c(Br)c1)NC1CCCCC1]

The synthesis method was the same as that in Embodiment 1.

¹H NMR (400 MHz, DMSO): δ 11.44 (s, 1H), 8.85 (s, 1H), 7.18 (t, J=8.8 Hz, 1H), 7.10 (m, 1H), 6.79-6.75 (m, 1H), 6.25 (s, 1H), 3.58-3.52 (m, 1H), 1.85-1.81 (m, 2H), 1.63-1.59 (m, 2H), 1.46-1.19 (m, 6H) ppm. ¹³C NMR (125 MHz, DMSO): δ 163.1, 159.2, 154.4, 149.2, 145.7, 135.1, 134.6, 112.6, 107.4, 100.3, 52.1, 31.9, 25.9, 24.8 ppm. MS (EI, m/z): 442 (M⁺+1).

Embodiment 8

(Z)-1-(4-(N-(3-bromo-4-fluorophenyl)-N'-hydroxyaminoiminomethyl)-1,2,5-oxadiazole-3-substituted)-3-cyclopentylurea

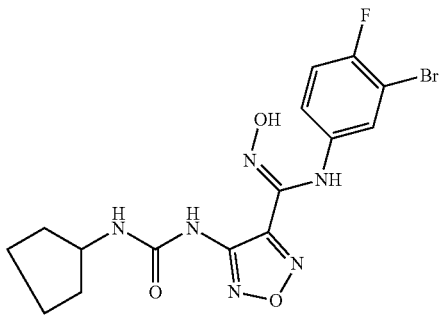 [SMILES: O=C(Nc1nonc1/C(=N/O)Nc1ccc(F)c(Br)c1)NC1CCCC1]

The synthesis method was the same as that in Embodiment 1.

¹H NMR (400 MHz, DMSO): δ 11.52 (s, 1H), 8.82 (s, 1H), 7.16 (t, J=8.8 Hz, 1H), 7.13-7.01 (m, 1H), 6.77-6.61 (m, 1H), 6.14 (s, 1H), 3.61-3.58 (m, 1H), 1.85-1.62 (m, 4H), 1.56-1.48 (m, 4H) ppm. ¹³C NMR (125 MHz, DMSO): δ 163.8, 158.2, 153.9, 148.1, 145.9, 135.2, 134.3, 112.3, 107.5, 101.1, 58.1, 32.4, 24.6 ppm. MS (EI, m/z): 428 (M⁺+1).

Embodiment 9

(Z)-1-(4-(N-(3-bromo-4-fluorophenyl)-N'-hydroxyaminoiminomethyl)-1,2,5-oxadiazole-3-substituted)-3-(4-methylcyclohexyl)urea

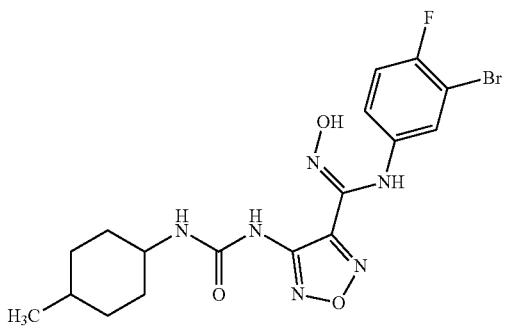

The synthesis method was the same as that in Embodiment 1.

¹H NMR (400 MHz, DMSO): δ 11.48 (s, 1H), 8.83 (s, 1H), 7.12 (t, J=8.8 Hz, 1H), 7.15-7.08 (m, 1H), 6.82-6.71 (m, 1H), 6.22 (s, 1H), 3.56-3.51 (m, 1H), 1.84-1.82 (m, 2H), 1.65-1.56 (m, 2H), 1.48-1.21 (m, 5H), 0.98 (s, 3H) ppm. ¹³C NMR (125 MHz, DMSO): δ 164.2, 159.1, 153.6, 149.2, 145.3, 135.1, 133.9, 112.6, 107.1, 100.6, 53.2, 33.9, 32.4, 31.6, 20.9 ppm. MS (EI, m/z): 456 (M⁺+1).

Embodiment 10

(Z)-1-(4-(N-(3-bromo-4-fluorophenyl)-N'-hydroxyaminoiminomethyl)-1,2,5-oxadiazole-3-substituted)-3-(tetrahydro-2H-pyran-4-substituted)urea The synthesis method was the same as that in Embodiment 1.

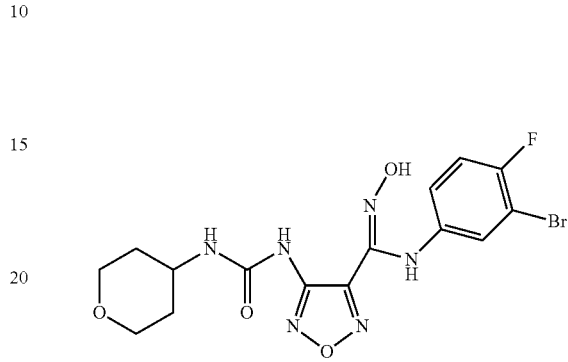

¹H NMR (400 MHz, DMSO): δ 11.53 (s, 1H), 8.85 (s, 1H), 7.19 (t, J=8.8 Hz, 1H), 7.13 (m, 1H), 6.85-6.75 (m, 1H), 6.29 (s, 1H), 3.66-3.58 (m, 4H), 3.55 (m, 1H), 1.68-1.56 (m, 4H) ppm. ¹³C NMR (125 MHz, DMSO): 5163.3, 159.5, 154.5, 149.3, 145.7, 135.3, 134.8, 112.7, 107.5, 100.6, 63.9, 52.8, 32.6 ppm. MS (EI, m/z): 444 (M⁺+1).

Embodiment 11

(Z)-1-(4-(N-(3-bromo-4-fluorophenyl)-N'-hydroxyaminoiminomethyl)-1,2,5-oxadiazole-3-substituted)-3-(piperidine-4-substituted)urea The synthesis method was the same as that in Embodiment 1.

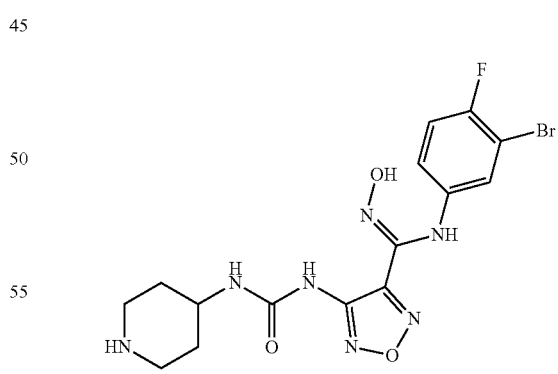

¹H NMR (400 MHz, DMSO): δ 11.52 (s, 1H), 8.83 (s, 1H), 7.17 (t, J=8.8 Hz, 1H), 7.11 (m, 1H), 6.85 (m, 1H), 6.28 (s, 1H), 3.56 (m, 1H), 2.79-2.69 (m, 4H), 1.67-1.55 (m, 4H) ppm. ¹³C NMR (125 MHz, DMSO): 5163.3, 159.5, 154.5, 149.3, 145.7, 135.3, 134.8, 112.7, 107.5, 100.6, 51.8, 42.6, 32.0 ppm. MS (EI, m/z): 443 (M⁺+1).

Embodiment 12

(Z)-1-(4-(N-(3-bromo-4-fluorophenyl)-N'-hydroxyaminoiminomethyl)-1,2,5-oxadiazole-3-substituted)-3-(1(methsulfonyl)piperidine-4-substituted) urea The synthesis method was the same as that in Embodiment 1.

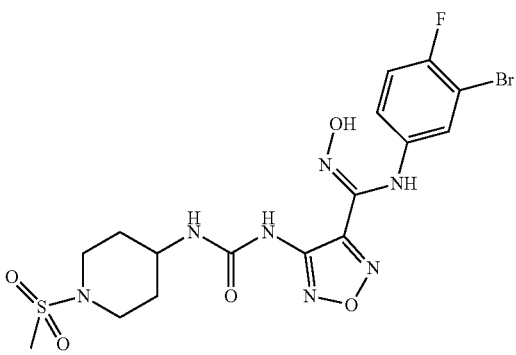 [SMILES: CS(=O)(=O)N1CCC(NC(=O)Nc2nonc2/C(=N/O)Nc2ccc(F)c(Br)c2)CC1]

¹H NMR (400 MHz, DMSO): δ 11.53 (s, 1H), 8.85 (s, 1H), 7.19 (t, J=8.8 Hz, 1H), 7.13 (m, 1H), 6.88 (m, 1H), 6.29 (s, 1H), 3.59 (m, 1H), 2.86 (s, 3H), 2.81-2.72 (m, 4H), 1.71-1.63 (m, 4H) ppm. ¹³C NMR (125 MHz, DMSO): 5163.3, 159.5, 154.5, 149.3, 145.7, 135.3, 134.8, 112.7, 107.5, 100.6, 52.9, 38.6, 33.7, 28.5 ppm. MS (EI, m/z): 521 (M⁺+1).

Embodiment 13

(Z)-1-(4-(N-(3-bromo-4-fluorophenyl)-N'-hydroxyaminoiminomethyl)-1,2,5-oxadiazole-3-substituted)-3-(3-hydroxypropane)urea The synthesis method was the same as that in Embodiment 1.

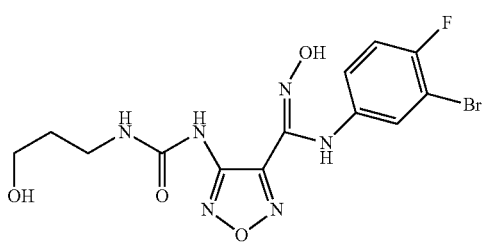 [SMILES: O=C(NCCCO)Nc1nonc1/C(=N/O)Nc1ccc(F)c(Br)c1]

¹H NMR (400 MHz, DMSO): δ 11.51 (s, 1H), 8.83 (s, 1H), 7.17 (t, J=8.8 Hz, 1H), 7.10 (m, 1H), 6.83 (m, 1H), 6.27 (s, 1H), 3.56 (t, J=6.8 Hz, 2H), 3.15 (t, J=6.6 Hz, 2H), 1.79 (m, 2H) ppm. ¹³C NMR (125 MHz, DMSO): 5163.0, 159.2, 154.3, 149.2, 145.5, 135.1, 134.8, 112.6, 107.3, 100.5, 59.9, 39.3, 31.6 ppm. MS (EI, m/z): 418 (M⁺+1).

Embodiment 14

(Z)-1-(4-(N-(3-bromo-4-fluorophenyl)-N'-hydroxyaminoiminomethyl)-1,2,5-oxadiazole-3-substituted)-3-(3-aminopropane)urea The synthesis method was the same as that in Embodiment 1.

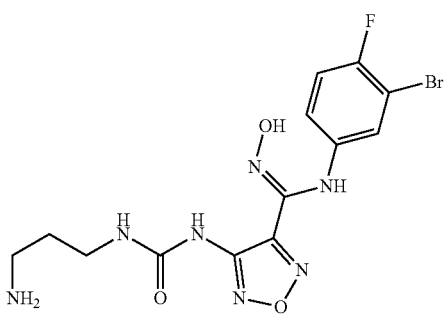 [SMILES: NCCCNC(=O)Nc1nonc1/C(=N/O)Nc1ccc(F)c(Br)c1]

¹H NMR (400 MHz, DMSO): δ 11.50 (s, 1H), 8.82 (s, 1H), 7.15 (t, J=8.8 Hz, 1H), 7.09 (m, 1H), 6.82 (m, 1H), 6.26 (s, 1H), 3.13 (t, J=6.8 Hz, 2H), 2.56 (t, J=6.6 Hz, 2H), 1.76 (m, 2H) ppm. ¹³C NMR (125 MHz, DMSO): δ 163.1, 159.3, 154.2, 149.1, 145.3, 135.2, 134.6, 112.5, 107.2, 100.3, 39.9, 38.6, 30.7 ppm. MS (EI, m/z): 417 (M⁺+1).

Embodiment 15

(Z)-1-(4-(N-(3-bromo-4-fluorophenyl)-N'-hydroxyaminoiminomethyl)-1,2,5-oxadiazole-3-substituted)-3-(1(aminosulfonyl)piperidine-4-substituted) urea The synthesis method was the same as that in Embodiment 1.

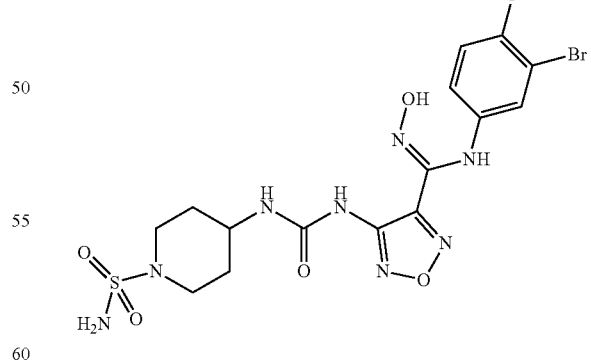

¹H NMR (400 MHz, DMSO): δ 11.52 (s, 1H), 8.83 (s, 1H), 7.18 (t, J=8.8 Hz, 1H), 7.12 (m, 1H), 6.87 (m, 1H), 6.28 (s, 1H), 3.58 (m, 1H), 2.80-2.70 (m, 4H), 1.85-1.66 (m, 4H) ppm. ¹³C NMR (125 MHz, DMSO): δ 163.2, 159.3, 154.2, 149.1, 145.6, 135.2, 134.6, 112.6, 107.3, 100.5, 46.1, 38.9, 28.3 ppm. MS (EI, m/z): 522 (M⁺+1).

Embodiment 16

(Z)-1-(4-(N-(3-bromo-4-fluorophenyl)-N'-hydroxyaminoiminomethyl)-1,2,5-oxadiazole-3-substituted)-3-(2-aminoethyl)urea The synthesis method was the same as that in Embodiment 1.

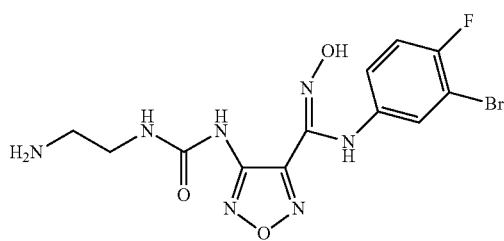 [SMILES: NCCNC(=O)Nc1nonc1/C(=N/O)Nc1ccc(F)c(Br)c1]

$^1$H NMR (400 MHz, DMSO): δ 11.48 (s, 1H), 8.81 (s, 1H), 7.12 (t, J=8.8 Hz, 1H), 7.05 (m, 1H), 6.80 (m, 1H), 6.23 (s, 1H), 3.36 (t, J=6.8 Hz, 2H), 2.86 (t, J=6.8 Hz, 2H) ppm. $^{13}$C NMR (125 MHz, DMSO): δ 163.2, 159.1, 154.1, 149.0, 145.1, 135.0, 134.3, 112.3, 107.0, 100.1, 43.7, 39.6, ppm. MS (EI, m/z): 403 (M$^+$+1).

Embodiment 17

(Z)-1-(4-(N-(3-bromo-4-fluorophenyl)-N'-hydroxyaminoiminomethyl)-1,2,5-oxadiazole-3-substituted)-3-(3-methamido-propyl)urea The synthesis method was the same as that in Embodiment 1.

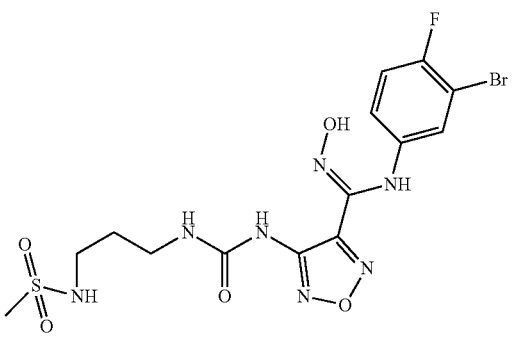 [SMILES: CS(=O)(=O)NCCCNC(=O)Nc1nonc1/C(=N/O)Nc1ccc(F)c(Br)c1]

$^1$H NMR (400 MHz, DMSO): δ 11.52 (s, 1H), 8.83 (s, 1H), 7.16 (t, J=8.8 Hz, 1H), 7.09 (m, 1H), 6.83 (m, 1H), 6.26 (s, 1H), 3.18 (t, J=6.8 Hz, 2H), 2.88 (s, 3H), 2.66 (t, J=6.6 Hz, 2H), 1.83 (m, 2H) ppm. $^{13}$C NMR (125 MHz, DMSO): δ 163.2, 159.5, 154.2, 149.2, 145.3, 135.1, 134.6, 112.6, 107.3, 100.4, 42.1, 39.7, 38.8, 27.9 ppm. MS (EI, m/z): 495 (M$^+$+1).

Embodiment 18

(Z)-1-(4-(N-(3-bromo-4-fluorophenyl)-N'-hydroxyaminoiminomethyl)-1,2,5-oxadiazole-3-substituted)-3-(3-aminosulfonylamino-propyl)urea The synthesis method was the same as that in Embodiment 1.

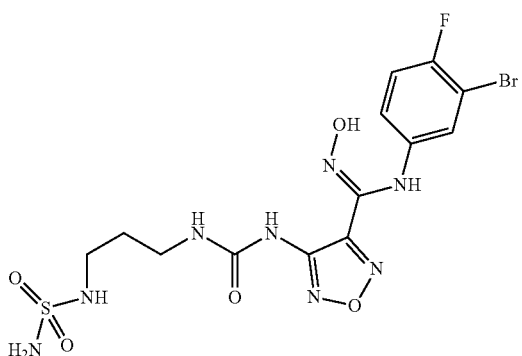

$^1$H NMR (400 MHz, DMSO): δ 11.51 (s, 1H), 8.84 (s, 1H), 7.16 (t, J=8.8 Hz, 1H), 7.08 (m, 1H), 6.82 (m, 1H), 6.25 (s, 1H), 3.16 (t, J=6.8 Hz, 2H), 2.65 (t, J=6.6 Hz, 2H), 1.81 (m, 2H) ppm. $^{13}$C NMR (125 MHz, DMSO): δ 163.1, 159.2, 154.0-, 149.2, 145.3, 135.0, 134.3, 112.2, 107.3, 100.3, 39.5, 37.2, 27.3 ppm. MS (EI, m/z): 496 (M$^+$+1).

Embodiment 19

(Z)-1-(4-(N-(4-bromo-3-fluorophenyl)-N'-hydroxyaminoiminomethyl)-1,2,5-oxadiazole-3-substituted)-3-phenylurea The synthesis method was the same as that in Embodiment 1.

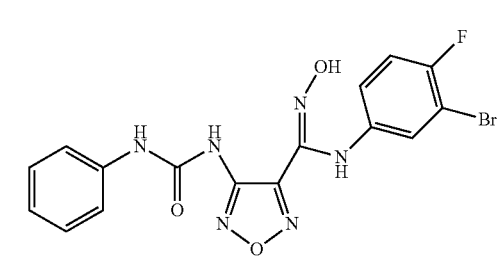 [SMILES: O=C(Nc1ccccc1)Nc1nonc1/C(=N/O)Nc1ccc(F)c(Br)c1]

$^1$H NMR (400 MHz, DMSO): δ 11.46 (s, 1H), 8.80 (s, 1H), 7.83 (d, J=8.4 Hz, 1H), 7.18-7.12 (m, 2H), 7.14-7.01 (m, 4H), 6.73-6.52 (m, 3H), 6.21 (s, 1H), 6.07 (s, 1H) ppm. $^{13}$C NMR (125 MHz, DMSO): δ 163.6, 160.0, 154.0, 151.4, 148.1, 140.3, 135.1, 134.8, 121.7, 120.6, 119.0, 118.6, 115.7, 114.6 ppm. MS (EI, m/z): 436 (M$^+$+1).

Embodiment 20

(Z)-1-(4-(N-(3-bromo-4-fluorophenyl)-N'-hydroxyaminoiminomethyl)-1,2,5-oxadiazole-3-substituted)-3-(4-methoxy-2-fluorophenyl)urea The synthesis method was the same as that in Embodiment 1.

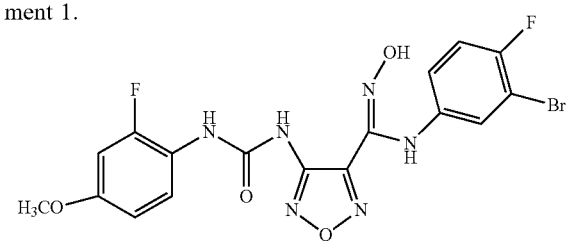

$^1$H NMR (400 MHz, DMSO): δ 11.47 (s, 1H), 8.89 (s, 1H), 7.57 (s, 1H), 7.25-7.21 (m, 2H), 7.21 (d, J=8.8 Hz, 1H), 7.11 (m, 1H), 6.77-6.52 (m, 1H), 6.21 (s, 1H), 6.10 (s, 1H), 3.76 (s, 3H) ppm. $^{13}$C NMR (125 MHz, DMSO): δ 162.3, 154.0, 151.1, 147.2, 140.1, 136.3, 134.6, 139.3, 120.8, 119.6, 119.3, 118.7, 114.3, 54.8 ppm. MS (EI, m/z): 484 (M$^+$+1).

Embodiment 21

(Z)-1-(4-(N-(3-bromo-4-fluorophenyl)-N'-hydroxyaminoiminomethyl)-1,2,5-oxadiazole-3-substituted)-3-(4-methoxy-2-trifluoromethylphenyl)urea The synthesis method was the same as that in Embodiment 1.

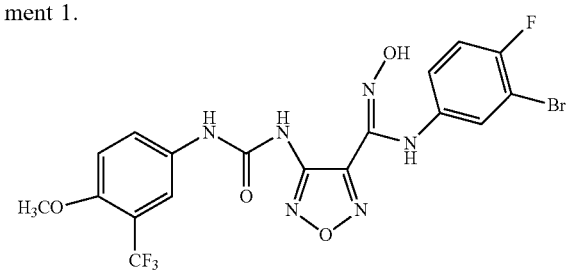

$^1$H NMR (400 MHz, DMSO): δ 11.49 (s, 1H), 8.89 (s, 1H), 7.59 (s, 1H), 7.28-7.23 (m, 2H), 7.23 (d, J=8.8 Hz, 1H), 7.15 (m, 1H), 6.79-6.55 (m, 1H), 6.23 (s, 1H), 6.13 (s, 1H), 3.78 (s, 3H) ppm. $^{13}$C NMR (125 MHz, DMSO): δ 162.5, 154.3, 151.2, 147.3, 140.2, 136.5, 134.8, 139.5, 120.9, 119.7, 119.4, 118.7, 114.5, 54.9 ppm. MS (EI, m/z): 534 (M$^+$+1).

Embodiment 22

(Z)-1-(4-(N-(3-chloro-4-fluorophenyl)-N'-hydroxyaminoiminomethyl)-1,2,5-oxadiazole-3-substituted)-3-(4-methoxyphenyl)urea The synthesis method was the same as that in Embodiment 1.

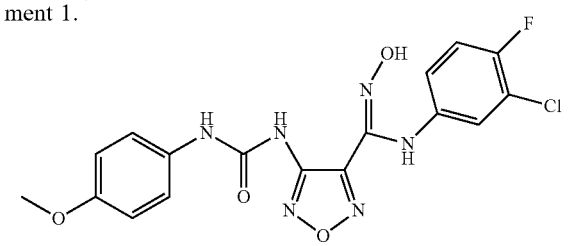

$^1$H NMR (400 MHz, DMSO): δ 11.42 (s, 1H), 8.82 (s, 1H), 7.16 (t, J=8.8 Hz, 1H), 7.08 (m, 1H), 6.76 (m, 1H), 6.23 (s, 1H), 3.56 (m, 1H), 1.84-1.80 (m, 2H), 1.61-1.58 (m, 2H), 1.45-1.16 (m, 4H) ppm. $^{13}$C NMR (125 MHz, DMSO): δ 162.0, 158.1, 153.9, 150.1, 148.3, 139.3, 133.5, 130.6, 120.1, 119.3, 119.0, 118.7, 114.7, 113.6, 54.5 ppm. MS (EI, m/z): 421 (M$^+$+1).

Embodiment 23

(Z)-1-(4-(N-(3-chloro-4-fluorophenyl)-N'-hydroxyaminoiminomethyl)-1,2,5-oxadiazole-3-substituted)-3-(4-methoxyphenyl)urea The synthesis method was the same as that in Embodiment 1.

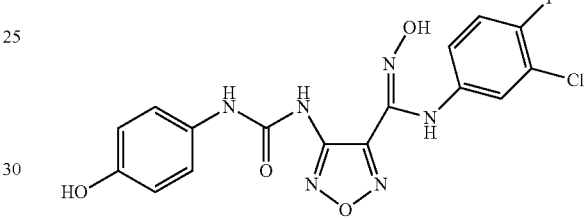

$^1$H NMR (400 MHz, DMSO): δ 11.41 (s, 1H), 8.80 (s, 1H), 7.15 (t, J=8.8 Hz, 1H), 7.06 (m, 1H), 6.75 (m, 1H), 6.23 (s, 1H), 3.53 (m, 1H) ppm. $^{13}$C NMR (125 MHz, DMSO): δ 162.0, 158.0, 153.7, 150.1, 148.2, 139.1, 133.3, 130.6, 120.1, 119.3, 119.0, 118.5, 114.3, 113.2 ppm. MS (EI, m/z): 407 (M$^+$+1).

Embodiment 24

(Z)-1-(4-(N-(3-chloro-4-fluorophenyl)-N'-hydroxyaminoiminomethyl)-1,2,5-oxadiazole-3-substituted)-3-(4-aminophenyl)urea The synthesis method was the same as that in Embodiment 1.

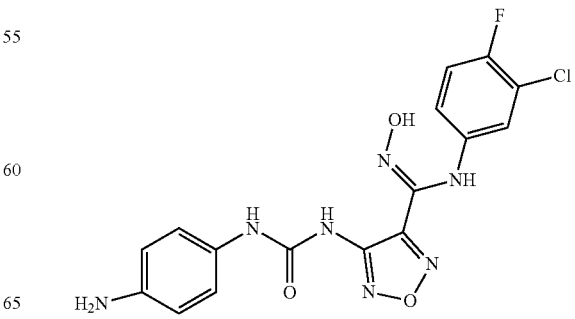

$^1$H NMR (400 MHz, DMSO): δ 11.38 (s, 1H), 8.79 (s, 1H), 7.13 (t, J=8.8 Hz, 1H), 7.03 (m, 1H), 6.72 (m, 1H), 6.21 (s, 1H), ppm. $^{13}$C NMR (125 MHz, DMSO): δ 161.8, 157.8, 153.7, 150.0, 148.1, 139.0, 133.2, 130.3, 120.0, 119.2, 119.0, 118.3, 114.2, 113.1 ppm. MS (EI, m/z): 406 (M$^+$+1).

Embodiment 25

(Z)-1-(4-(N-(3-chloro-4-fluorophenyl)-N'-hydroxyaminoiminomethyl)-1,2,5-oxadiazole-3-substituted)-3-cyclohexylurea

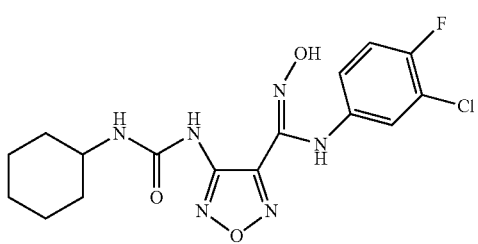 [SMILES: O=C(Nc1nonc1/C(=N/O)Nc1ccc(F)c(Cl)c1)NC1CCCCC1]

The synthesis method was the same as that in Embodiment 1.

$^1$H NMR (400 MHz, DMSO): δ 11.42 (s, 1H), 8.84 (s, 1H), 7.17 (t, J=8.8 Hz, 1H), 7.10 (m, 1H), 6.78-6.75 (m, 1H), 6.23 (s, 1H), 3.57-3.51 (m, 1H), 1.84-1.80 (m, 2H), 1.62-1.57 (m, 2H), 1.45-1.17 (m, 6H) ppm. $^{13}$C NMR (125 MHz, DMSO): δ 163.0, 159.1, 154.2, 149.1, 145.5, 135.0, 134.3, 112.5, 107.3, 100.2, 52.0, 31.8, 25.8, 24.7 ppm. MS (EI, m/z): 397 (M$^+$+1).

Embodiment 26

(Z)-1-(4-(N-(3-bromo-4-fluorophenyl)-N'-hydroxyaminoiminomethyl)-1,2,5-oxadiazole-3-substituted)-3-(4-aminocyclohexyl)urea

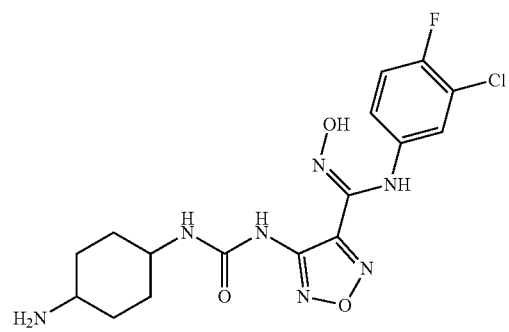 [SMILES: NC1CCC(NC(=O)Nc2nonc2/C(=N/O)Nc2ccc(F)c(Cl)c2)CC1]

The synthesis method was the same as that in Embodiment 1.

$^1$H NMR (400 MHz, DMSO): δ 11.47 (s, 1H), 8.82 (s, 1H), 7.11 (t, J=8.8 Hz, 1H), 7.14-7.07 (m, 1H), 6.81-6.70 (m, 1H), 6.22 (s, 1H), 3.55-3.50 (m, 1H), 2.86 (m, 1H), 1.83-1.81 (m, 2H), 1.64-1.55 (m, 2H), 1.47-1.21 (m, 5H) ppm. $^{13}$C NMR (125 MHz, DMSO): δ 164.1, 159.0, 153.5, 149.1, 145.2, 135.0, 133.8, 112.5, 107.0, 100.5, 53.1, 33.8, 33.8, 32.2, 31.3 ppm. MS (EI, m/z): 412 (M$^+$+1).

Embodiment 27

(Z)-1-(4-(N-(3-bromo-4-fluorophenyl)-N'-hydroxyaminoiminomethyl)-1,2,5-oxadiazole-3-substituted)-3-(4-aminocyclohexyl)urea

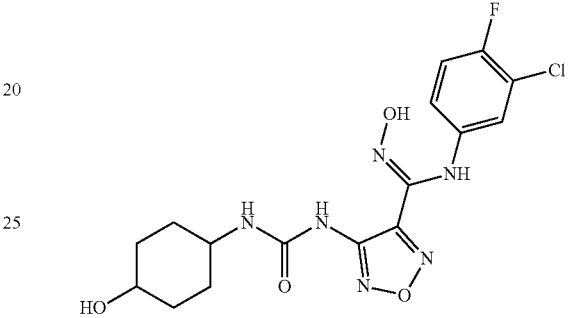

$^1$H NMR (400 MHz, DMSO): δ 11.49 (s, 1H), 8.85 (s, 1H), 7.13 (t, J=8.8 Hz, 1H), 7.13-7.06 (m, 1H), 6.83-6.72 (m, 1H), 6.25 (s, 1H), 3.57-3.53 (m, 1H), 3.39 (m, 1H), 1.85-1.82 (m, 2H), 1.66-1.56 (m, 2H), 1.48-1.23 (m, 5H) ppm. $^{13}$C NMR (125 MHz, DMSO): δ 164.3, 159.2, 153.7, 149.3, 145.3, 135.3, 133.9, 112.8, 107.3, 100.7, 53.5, 51.9, 33.9, 32.6, 31.5 ppm. MS (EI, m/z): 413 (M$^+$+1).

Embodiment 28

(Z)-1-(4-(N-(3-chloro-4-fluorophenyl)-N'-hydroxyaminoiminomethyl)-1,2,5-oxadiazole-3-substituted)-3-(23-hydroxyethane)urea The synthesis method was the same as that in Embodiment 1.

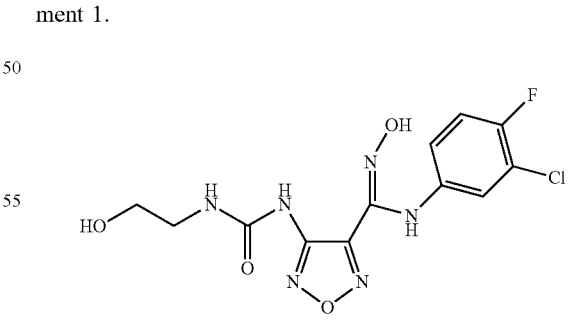

$^1$H NMR (400 MHz, DMSO): δ 11.53 (s, 1H), 8.85 (s, 1H), 7.19 (t, J=8.8 Hz, 1H), 7.13 (m, 1H), 6.85 (m, 1H), 6.28 (s, 1H), 3.58 (t, J=6.8 Hz, 2H), 3.19 (t, J=6.8 Hz, 2H) ppm. $^{13}$C NMR (125 MHz, DMSO): δ 163.2, 159.3, 154.6, 149.5, 145.7, 135.3, 134.9, 112.8, 107.5, 100.6, 59.9, 39.8 ppm. MS (EI, m/z): 359 (M$^+$+1).

Embodiment 29

(Z)-1-(4-(N-(3-chloro-4-fluorophenyl)-N'-hydroxyaminoiminomethyl)-1,2,5-oxadiazole-3-substituted)-3-(3-methamido-ethyl)urea

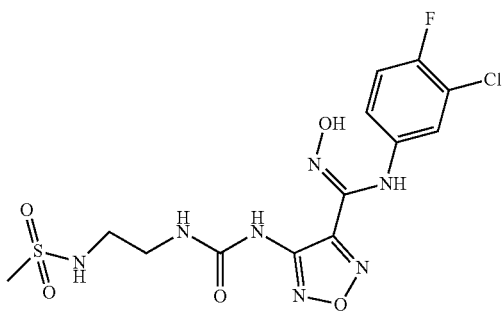 [SMILES: CS(=O)(=O)NCCNC(=O)Nc1nonc1/C(=N/O)Nc1ccc(F)c(Cl)c1]

The synthesis method was the same as that in Embodiment 1.

$^1$H NMR (400 MHz, DMSO): δ 11.53 (s, 1H), 8.85 (s, 1H), 7.18 (t, J=8.8 Hz, 1H), 7.09 (m, 1H), 6.84 (m, 1H), 6.27 (s, 1H), 3.41 (t, J=6.8 Hz, 2H), 2.93 (t, J=6.8 Hz, 2H), 2.83 (s, 3H) ppm. $^{13}$C NMR (125 MHz, DMSO): δ 163.0, 159.2, 154.1, 149.2, 145.1, 135.0, 134.3, 112.5, 107.2, 100.3, 42.3, 41.7, 40.2 ppm. MS (EI, m/z): 436 (M$^+$+1).

Embodiment 30

(Z)-1-(4-(N-(3-chloro-4-fluorophenyl)-N'-hydroxyaminoiminomethyl)-1,2,5-oxadiazole-3-substituted)-3-(3-methamido-ethyl)urea

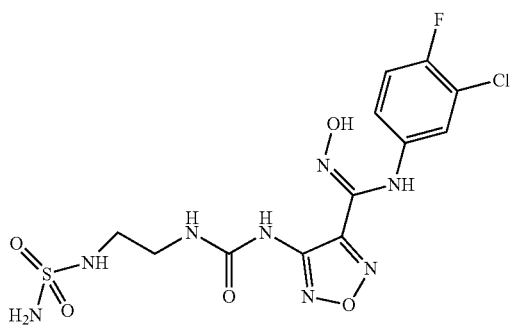 [SMILES: NS(=O)(=O)NCCNC(=O)Nc1nonc1/C(=N/O)Nc1ccc(F)c(Cl)c1]

The synthesis method was the same as that in Embodiment 1.

$^1$H NMR (400 MHz, DMSO): δ 11.54 (s, 1H), 8.86 (s, 1H), 7.19 (t, J=8.8 Hz, 1H), 7.09 (m, 1H), 6.83 (m, 1H), 6.28 (s, 1H), 3.43 (t, J=6.8 Hz, 2H), 2.95 (t, J=6.8 Hz, 2H), 2.03 (s, 2H) ppm. $^{13}$C NMR (125 MHz, DMSO): δ 163.1, 159.3, 154.3, 149.4, 145.1, 135.1, 134.3, 112.6, 107.3, 100.4, 40.7, 39.6 ppm. MS (EI, m/z): 437 (M$^+$+1).

Embodiment 31

(Z)-1-(4-(N-(3-bromo-4-fluorophenyl)-N'-hydroxyaminoiminomethyl)-1,2,5-oxadiazole-3-substituted)-3-cyclobutylurea

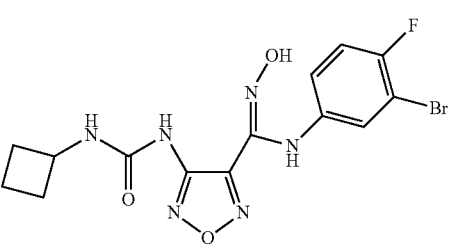 [SMILES: O=C(Nc1nonc1/C(=N/O)Nc1ccc(F)c(Br)c1)NC1CCC1]

The synthesis method was the same as that in Embodiment 1.

$^1$H NMR (400 MHz, DMSO): δ 11.53 (s, 1H), 8.83 (s, 1H), 7.17 (t, J=8.8 Hz, 1H), 7.14-7.02 (m, 1H), 6.77-6.62 (m, 1H), 6.15 (s, 1H), 4.09 (m, 1H), 2.33-2.08 (m, 4H), 2.02-1.93 (m, 2H) ppm. $^{13}$C NMR (125 MHz, DMSO): δ 163.9, 158.3, 153.9, 148.2, 145.9, 135.3, 134.4, 112.3, 107.6, 101.2, 48.3, 31.2, 16.6 ppm. MS (EI, m/z): 414 (M$^+$+1).

Embodiment 32

(Z)-1-(4-(N-(3-bromo-4-fluorophenyl)-N'-hydroxyaminoiminomethyl)-1,2,5-oxadiazole-3-substituted)-3-cyclopropylurea

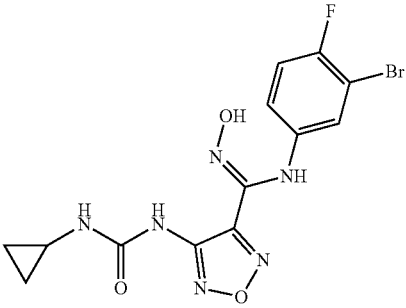 [SMILES: O=C(Nc1nonc1/C(=N/O)Nc1ccc(F)c(Br)c1)NC1CC1]

The synthesis method was the same as that in Embodiment 1.

$^1$H NMR (400 MHz, DMSO): δ 11.51 (s, 1H), 8.80 (s, 1H), 7.15 (t, J=8.8 Hz, 1H), 7.13-7.01 (m, 1H), 6.75-6.60 (m, 1H), 6.13 (s, 1H), 3.33 (m, 1H), 1.25-1.03 (m, 4H) ppm. $^{13}$C NMR (125 MHz, DMSO): δ 163.3, 158.0, 153.6, 148.0, 145.5, 135.1, 134.2, 112.3, 107.2, 101.0, 38.3, 11.2 ppm. MS (EI, m/z): 400 (M$^+$+1).

Embodiment 33

(Z)-1-(4-(N-(3-bromo-4-fluorophenyl)-N'-hydroxyaminoiminomethyl)-1,2,5-oxadiazole-3-substituted)-3-cycloheptylurea

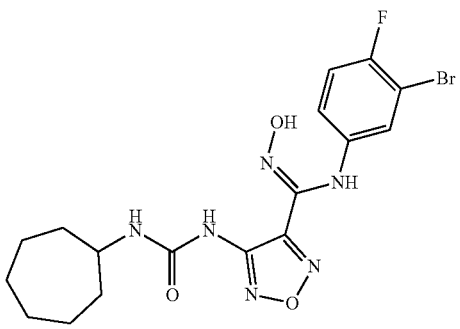 [SMILES: O=C(Nc1nonc1/C(=N/O)Nc1ccc(F)c(Br)c1)NC1CCCCCC1]

The synthesis method was the same as that in Embodiment 1.

¹H NMR (400 MHz, DMSO): δ 11.42 (s, 1H), 8.84 (s, 1H), 7.16 (t, J=8.8 Hz, 1H), 7.10 (m, 1H), 6.77-6.73 (m, 1H), 6.24 (s, 1H), 3.57 (m, 1H), 1.68-1.41 (m, 4H), 1.38-1.28 (m, 4H), 1.30-1.25 (m, 4H) ppm. ¹³C NMR (125 MHz, DMSO): δ 163.0, 159.2, 154.4, 149.2, 145.7, 135.1, 134.6, 112.6, 107.4, 100.3, 49.9, 31.7, 29.1, 23.8 ppm. MS (EI, m/z): 456 (M⁺+1).

Embodiment 34

(Z)-1-(4-(N-(3-bromo-4-fluorophenyl)-N'-hydroxyaminoiminomethyl)-1,2,5-oxadiazole-3-substituted)-3-(1H-indole-4-substituted)urea

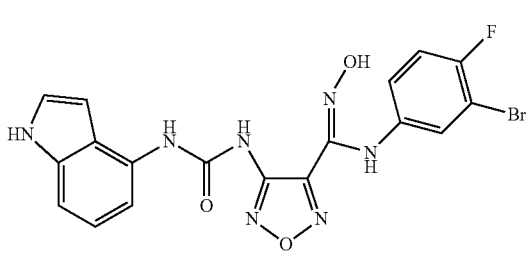 [SMILES: O=C(Nc1nonc1/C(=N/O)Nc1ccc(F)c(Br)c1)Nc1cccc2[nH]ccc12]

The synthesis method was the same as that in Embodiment 1.

¹H NMR (400 MHz, DMSO): δ 11.43 (s, 1H), 10.2 (s, 1H), 8.82 (s, 1H), 7.39 (d, J=8.6 Hz, 1H), 7.28 (d, J=8.8 Hz, 1H), 7.17 (t, J=8.8 Hz, 1H), 7.14 (d, J=8.6 Hz, 1H), 7.09 (m, 1H), 7.05 (m, 1H), 6.78 (m, 1H), 6.55 d, J=8.6 Hz, 1H), 6.24 (s, 1H) ppm. ¹³C NMR (125 MHz, DMSO): δ 162.1, 158.2, 153.8, 150.2, 148.5, 139.4, 135.8, 133.5, 130.7, 130.3, 124.3, 120.3, 120.1, 119.3, 119.0, 118.7, 114.7, 113.6, 112.4, 106.7, 102.3 ppm. MS (EI, m/z): 475 (M⁺+1).

Embodiment 35

(Z)-1-(4-(N-(4-bromo-3-fluorophenyl)-N'-hydroxyaminoiminomethyl)-1,2,5-oxadiazole-3-substituted)-3-(piperidine-4-substituted)urea

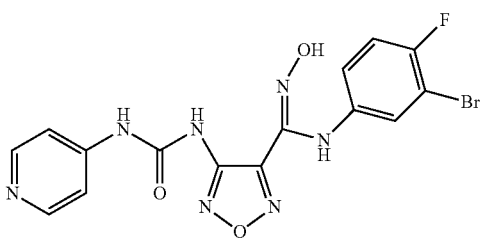 [SMILES: O=C(Nc1ccncc1)Nc1nonc1/C(=N/O)Nc1ccc(F)c(Br)c1]

The synthesis method was the same as that in Embodiment 1.

¹H NMR (400 MHz, DMSO): δ 11.54 (s, 1H), 8.85 (s, 1H), 8.45 (d, J=7.6 Hz, 2H), 7.17 (t, J=8.8 Hz, 1H), 7.15-7.03 (m, 1H), 6.78-6.62 (m, 1H), 6.60 (d, J=7.6 Hz, 2H), 6.15 (s, 1H) ppm. ¹³C NMR (125 MHz, DMSO): δ 163.9, 158.3, 155.3, 153.9, 150.3, 148.2, 145.9, 135.3, 134.4, 112.3, 109.1, 107.6, 101.2, ppm. MS (EI, m/z): 437 (M⁺+1).

Embodiment 36

(Z)-1-(4-(N-(3-bromo-4-fluorophenyl)-N'-hydroxyaminoiminomethyl)-1,2,5-oxadiazole-3-substituted)-3-(1H-indole-7-substituted)urea

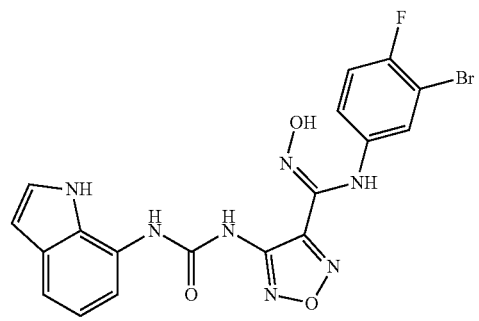 [SMILES: O=C(Nc1nonc1/C(=N/O)Nc1ccc(F)c(Br)c1)Nc1cccc2cc[nH]c12]

The synthesis method was the same as that in Embodiment 1.

¹H NMR (400 MHz, DMSO): δ 11.53 (s, 1H), 8.83 (s, 1H), 7.46 (d, J=7.8 Hz, 1H), 7.29 (d, J=7.6 Hz, 1H), 7.25 (d, J=7.8 Hz, 1H), 7.17 (t, J=8.8 Hz, 1H), 7.14-7.02 (m, 1H), 6.98 (m, 1H), 6.77-6.62 (m, 1H), 6.46 (d, J=7.8 Hz, 1H), 6.15 (s, 1H), ppm. ¹³C NMR (125 MHz, DMSO): δ 163.9, 158.3, 153.9, 148.2, 145.9, 140.5, 135.3, 134.4, 128.3, 124.4, 122.4, 120.7, 114.6, 112.7, 112.3, 107.6, 102.3, 101.2 ppm. MS (EI, m/z): 475 (M⁺+1).

Embodiment 37

(Z)-1-(4-(N-(3-bromo-4-fluorophenyl)-N'-hydroxyaminoiminomethyl)-1,2,5-oxadiazole-3-substituted)-3-(1H-indole-3-substituted)urea

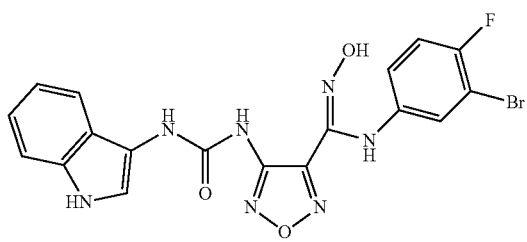 [SMILES: O=C(Nc1nonc1/C(=N/O)Nc1ccc(F)c(Br)c1)Nc1c[nH]c2ccccc12]

The synthesis method was the same as that in Embodiment 1.

$^1$H NMR (400 MHz, DMSO): δ 11.53 (s, 1H), 10.2 (s, 1H), 8.83 (s, 1H), 7.61 (d, J=7.8 Hz, 1H), 7.40 (d, J=7.2 Hz, 1H), 7.32 (s, 1H), 7.17 (t, J=8.8 Hz, 1H), 7.14-7.03 (m, 2H), 7.01 (m, 1H), 6.77 (m, 1H), 6.15 (s, 1H) ppm. $^{13}$C NMR (125 MHz, DMSO): δ 163.9, 158.3, 153.9, 148.2, 145.9, 135.6, 135.3, 134.4, 124.0, 122.2, 120.5, 120.1, 119.0, 112.3, 111.1, 107.6, 102.3, 101.2 ppm. MS (EI, m/z): 475 (M$^+$+1).

Embodiment 38

(Z)-1-(4-(N-(3-bromo-4-fluorophenyl)-N'-hydroxyaminoiminomethyl)-1,2,5-oxadiazole-3-substituted)-3-(benzofuran-3-substituted)urea

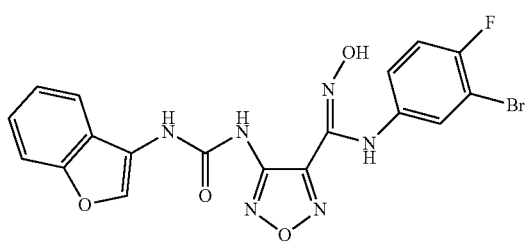 [SMILES: O=C(Nc1nonc1/C(=N/O)Nc1ccc(F)c(Br)c1)Nc1coc2ccccc12]

The synthesis method was the same as that in Embodiment 1.

$^1$H NMR (400 MHz, DMSO): δ 11.54 (s, 1H), 8.83 (s, 1H), 7.55 (d, J=7.6 Hz, 1H), 7.50 (s, 1H), 7.42 (d, J=7.6 Hz, 1H), 7.25 (m, 1H), 7.17 (t, J=8.8 Hz, 1H), 7.14-7.02 (m, 2H), 6.75 (m, 1H), 6.15 (s, 1H) ppm. $^{13}$C NMR (125 MHz, DMSO): δ 163.9, 158.3, 156.4, 153.9, 148.2, 145.9, 145.0, 135.3, 134.4, 124.7, 123.9, 123.3, 121.2, 112.3, 111.6, 107.6, 107.0, 101.2 ppm. MS (EI, m/z): 476 (M$^+$+1).

Embodiment 39

(Z)-1-(4-(N-(3-bromo-4-fluorophenyl)-N'-hydroxyaminoiminomethyl)-1,2,5-oxadiazole-3-substituted)-3-(benzothiophene-3-substituted)urea

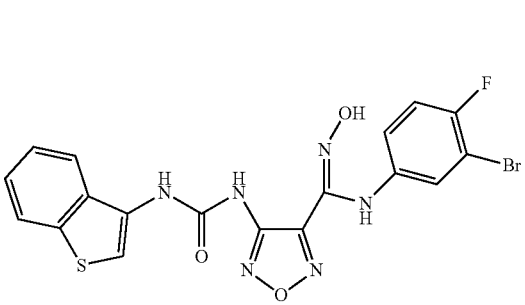 [SMILES: O=C(Nc1nonc1/C(=N/O)Nc1ccc(F)c(Br)c1)Nc1csc2ccccc12]

The synthesis method was the same as that in Embodiment 1.

$^1$H NMR (400 MHz, DMSO): δ 11.53 (s, 1H), 8.83 (s, 1H), 7.86 (d, J=7.2 Hz, 1H), 7.78 (d, J=7.2 Hz, 1H), 7.33-7.30 (m, 2H), 7.17 (t, J=8.8 Hz, 1H), 7.13 (m, 1H), 6.77 (m, 1H), 6.30 (s, 1H), 6.15 (s, 1H), ppm. $^{13}$C NMR (125 MHz, DMSO): δ 163.9, 158.3, 153.9, 148.2, 145.9, 139.5, 136.0, 135.3, 134.4, 127.2, 124.4, 124.3, 123.3, 122.8, 112.3, 109.7, 107.6, 101.2 ppm. MS (EI, m/z): 492 (M$^+$+1).

Embodiment 40

(Z)-1-(4-(N-(3-bromo-4-fluorophenyl)-N'-hydroxyaminoiminomethyl)-1,2,5-oxadiazole-3-substituted)-3-(1H-pyrrole-3-substituted)urea

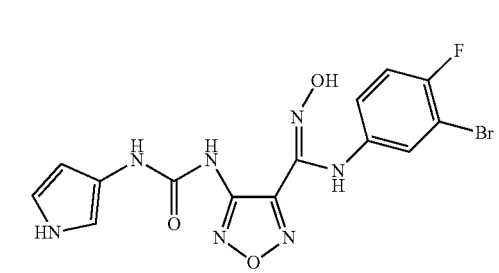 [SMILES: O=C(Nc1cc[nH]c1)Nc1nonc1/C(=N/O)Nc1ccc(F)c(Br)c1]

The synthesis method was the same as that in Embodiment 1.

$^1$H NMR (400 MHz, DMSO): δ 11.53 (s, 1H), 8.83 (s, 1H), 7.17 (t, J=8.8 Hz, 1H), 7.12 (m, 1H), 6.74 (m, 1H), 6.63 (s, 1H), 6.59 (d, J=6.8 Hz, 1H), 6.15 (s, 1H), 6.10 (d, J=6.8 Hz, 1H) ppm. $^{13}$C NMR (125 MHz, DMSO): δ 163.9, 158.3, 153.9, 148.2, 145.9, 135.3, 134.4, 131.9, 112.3, 117.5, 109.3, 108.0, 107.6, 101.2, ppm. MS (EI, m/z): 425 (M$^+$+1).

Embodiment 41

(Z)-1-(4-(N-(3-bromo-4-fluorophenyl)-N'-hydroxyaminoiminomethyl)-1,2,5-oxadiazole-3-substituted)-3-(furan-3-substituted)urea

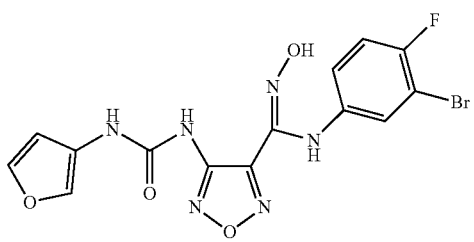 [SMILES: O=C(Nc1ccoc1)Nc1nonc1/C(=N/O)Nc1ccc(F)c(Br)c1]

The synthesis method was the same as that in Embodiment 1.

$^1$H NMR (400 MHz, DMSO): δ 11.53 (s, 1H), 8.83 (s, 1H), 7.45 (s 1H), 7.40 (d, J=7.0 Hz, 1H), 7.17 (t, J=8.8 Hz, 1H), 7.13 (m, 1H), 6.76 (m, 1H), 6.33 (d, J=7.0 Hz, 1H), 6.15 (s, 1H) ppm. $^{13}$C NMR (125 MHz, DMSO): δ 163.9, 158.3, 153.9, 148.2, 145.9, 144.2, 141.6, 135.3, 134.4, 130.4, 124.7, 112.3, 107.6, 101.2 ppm. MS (EI, m/z): 426 (M$^+$+1).

Embodiment 42

(Z)-1-(4-(N-(3-bromo-4-fluorophenyl)-N'-hydroxyaminoiminomethyl)-1,2,5-oxadiazole-3-substituted)-3-(thiophene-3-substituted)urea

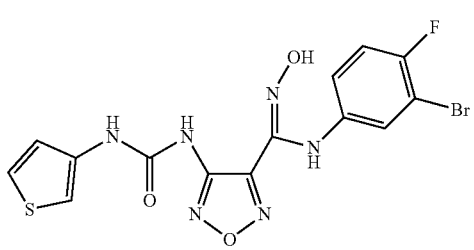 [SMILES: O=C(Nc1ccsc1)Nc1nonc1/C(=N/O)Nc1ccc(F)c(Br)c1]

The synthesis method was the same as that in Embodiment 1.

$^1$H NMR (400 MHz, DMSO): δ 11.53 (s, 1H), 8.83 (s, 1H), 7.17 (t, J=8.8 Hz, 1H), 7.12 (m, 1H), 6.95 (d, J=6.6 Hz, 1H), 6.74 (m, 1H), 6.43 (d, J=6.6 Hz, 1H), 6.15 (s, 1H), 6.10 (s, 1H) ppm. $^{13}$C NMR (125 MHz, DMSO): δ 163.9, 158.3, 153.9, 148.2, 145.9, 138.7, 135.3, 134.4, 124.6, 116.0, 112.3, 107.6, 101.2, 86.8 ppm. MS (EI, m/z): 442 (M$^+$+1).

Embodiment 43

(Z)-1-(4-(N-(3-bromo-4-fluorophenyl)-N'-hydroxyaminoiminomethyl)-1,2,5-oxadiazole-3-substituted)-3-(pyrimidine-2-substituted)urea

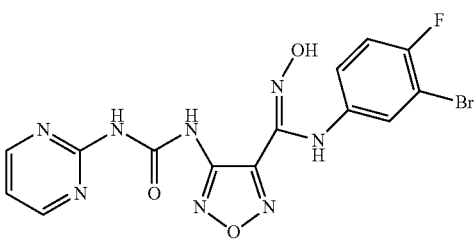 [SMILES: O=C(Nc1ncccn1)Nc1nonc1/C(=N/O)Nc1ccc(F)c(Br)c1]

The synthesis method was the same as that in Embodiment 1.

$^1$H NMR (400 MHz, DMSO): δ 11.53 (s, 1H), 8.83 (s, 1H), 8.38 (d, J=8.0 Hz, 2H), 7.17 (t, J=8.8 Hz, 1H), 7.12 (m, 1H), 6.75 (m, 1H), 6.58 (d, J=8.0 Hz, 1H), 6.15 (s, 1H) ppm. $^{13}$C NMR (125 MHz, DMSO): δ 163.9, 158.3, 158.0, 157.6, 153.9, 148.2, 145.9, 135.3, 134.4, 112.3, 110.3, 107.6, 101.2, ppm. MS (EI, m/z): 438 (M$^+$+1).

Embodiment 44

(Z)-1-(4-(N-(3-bromo-4-fluorophenyl)-N'-hydroxyaminoiminomethyl)-1,2,5-oxadiazole-3-substituted)-3-(1,3,5-triazine-2-substituted)urea

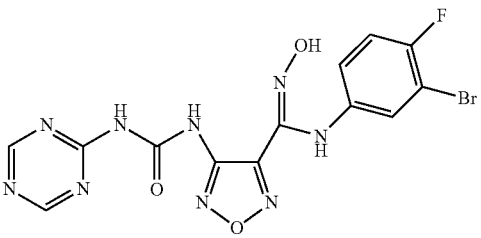 [SMILES: O=C(Nc1ncncn1)Nc1nonc1/C(=N/O)Nc1ccc(F)c(Br)c1]

The synthesis method was the same as that in Embodiment 1.

$^1$H NMR (400 MHz, DMSO): δ 11.53 (s, 1H), 8.86 (s, 1H), 8.83 (s, 1H), 7.17 (t, J=8.8 Hz, 1H), 7.142 (m, 1H), 6.762 (m, 1H), 6.15 (s, 1H) ppm. $^{13}$C NMR (125 MHz, DMSO): δ 166.9, 164.1, 163.9, 158.3, 153.9, 148.2, 145.9, 135.3, 134.4, 112.3, 107.6, 101.2 ppm. MS (EI, m/z): 439 (M$^+$+1).

Embodiment 45

(Z)-1-(4-(N-(3-bromo-4-fluorophenyl)-N'-hydroxyaminoiminomethyl)-1,2,5-oxadiazole-3-substituted)-3-(pyrimidine-4-substituted)urea

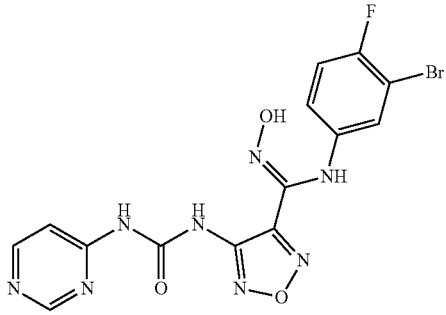 [SMILES: O=C(Nc1ccncn1)Nc1nonc1/C(=N/O)Nc1ccc(F)c(Br)c1]

The synthesis method was the same as that in Embodiment 1.

$^1$H NMR (400 MHz, DMSO): δ 11.53 (s, 1H), 8.83 (s, 1H), 8.39 (s, 1H), 8.05 (d, J=8.0 Hz, 1H), 7.17 (t, J=8.8 Hz, 1H), 7.13 (m, 1H), 6.75 (m, 1H), 6.45 (d, J=8.0 Hz, 2H), 6.15 (s, 1H) ppm. $^{13}$C NMR (125 MHz, DMSO): δ 163.9, 159.5, 158.3, 158.1, 156.3, 153.9, 148.2, 145.9, 135.3, 134.4, 112.3, 107.6, 107.2, 101.2 ppm. MS (EI, m/z): 438 (M$^+$+1).

Embodiment 46

(Z)-1-(4-(N-(3-bromo-4-fluorophenyl)-N'-hydroxyaminoiminomethyl)-1,2,5-oxadiazole-3-substituted)-3-(1H-imidazole-2-substituted)urea

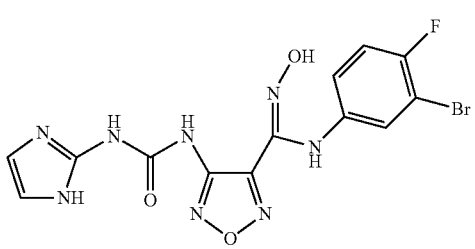 [SMILES: O=C(Nc1ncc[nH]1)Nc1nonc1/C(=N/O)Nc1ccc(F)c(Br)c1]

The synthesis method was the same as that in Embodiment 1.

$^1$H NMR (400 MHz, DMSO): 512.5 (s, 1H), 11.53 (s, 1H), 8.83 (s, 1H), 7.17 (t, J=8.8 Hz, 1H), 7.15 (d, J=5.8 Hz, 1H), 7.13 (m, 1H), 6.72 (m, 1H), 6.13 (s, 1H) ppm. $^{13}$C NMR (125 MHz, DMSO): δ 163.9, 158.3, 153.9, 148.2, 145.9, 136.0, 135.3, 134.4, 127.8, 112.3, 107.6, 101.2, ppm. MS (EI, m/z): 426 (M$^+$+1).

Embodiment 47

(Z)-1-(4-(N-(3-bromo-4-fluorophenyl)-N'-hydroxyaminoiminomethyl)-1,2,5-oxadiazole-3-substituted)-3-(tetrahydrofuran-substituted)urea

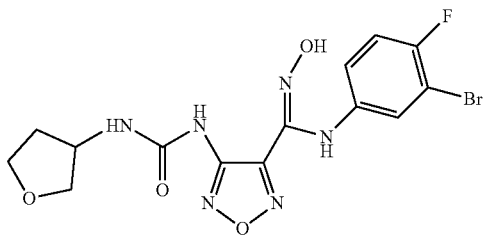 [SMILES: O=C(Nc1nonc1/C(=N/O)Nc1ccc(F)c(Br)c1)NC1CCOC1]

The synthesis method was the same as that in Embodiment 1.

$^1$H NMR (400 MHz, DMSO): δ 11.53 (s, 1H), 8.83 (s, 1H), 7.17 (t, J=8.8 Hz, 1H), 7.15 (m, 1H), 6.77 (m, 1H), 6.15 (s, 1H), 4.10-3.93 (m, 2H), 3.90 (m, 1H), 3.80-3.70 (m, 2H), 2.19-1.95 (m, 2H) ppm. $^{13}$C NMR (125 MHz, DMSO): δ 163.9, 158.3, 153.9, 148.2, 145.9, 135.3, 134.4, 112.3, 107.6, 101.2, 77.6, 67.9, 51.8, 51.5 ppm. MS (EI, m/z): 430 (M$^+$+1).

Embodiment 48

(Z)-1-(4-(N-(3-bromo-4-fluorophenyl)-N'-hydroxyaminoiminomethyl)-1,2,5-oxadiazole-3-substituted)piperazine-1-carbamide

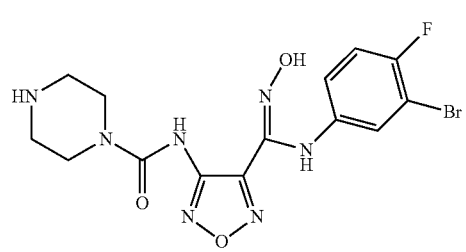 [SMILES: O=C(Nc1nonc1/C(=N/O)Nc1ccc(F)c(Br)c1)N1CCNCC1]

The synthesis method was the same as that in Embodiment 1.

$^1$H NMR (400 MHz, DMSO): δ 11.53 (s, 1H), 8.83 (s, 1H), 7.17 (t, J=8.8 Hz, 1H), 7.13 (m, 1H), 6.75 (m, 1H), 6.15 (s, 1H), 3.28 (t, J=7.8 Hz, 2H), 2.81 (t, J=7.8 Hz, 2H) ppm. $^{13}$C NMR (125 MHz, DMSO): δ 163.9, 158.3, 153.9, 148.2, 145.9, 135.3, 134.4, 112.3, 107.6, 101.2, 51.8, 45.3 ppm. MS (EI, m/z): 429 (M$^+$+1).

Embodiment 49

(Z)-1-(4-(N-(3-bromo-4-fluorophenyl)-N'-hydroxyaminoiminomethyl)-1,2,5-oxadiazole-3-substituted)morpholine-1-carbamide

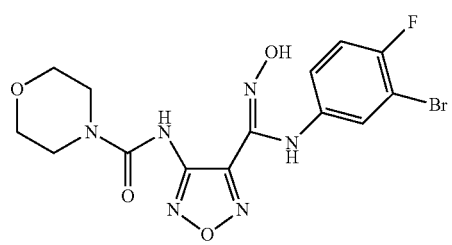 [SMILES: O=C(Nc1nonc1/C(=N/O)Nc1ccc(F)c(Br)c1)N1CCOCC1]

The synthesis method was the same as that in Embodiment 1.

¹H NMR (400 MHz, DMSO): δ 11.53 (s, 1H), 8.83 (s, 1H), 7.17 (t, J=8.8 Hz, 1H), 7.12 (m, 1H), 6.75 (m, 1H), 6.15 (s, 1H), 3.68 (t, J=7.8 Hz, 2H), 3.48 (t, J=7.8 Hz, 2H) ppm. ¹³C NMR (125 MHz, DMSO): δ 163.9, 158.3, 153.9, 148.2, 145.9, 135.3, 134.4, 112.3, 107.6, 101.2, 65.9, 47.7 ppm. MS (EI, m/z): 430 (M⁺+1).

Embodiment 50

(Z)-1-(4-(N-(3-bromo-4-fluorophenyl)-N'-hydroxyaminoiminomethyl)-1,2,5-oxadiazole-3-substituted)-4-(methsulfonyl)piperidine-1-carbamide

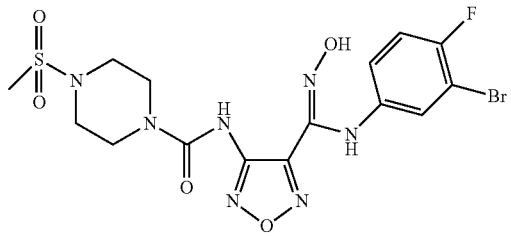 [SMILES: CS(=O)(=O)N1CCN(C(=O)Nc2nonc2/C(=N/O)Nc2ccc(F)c(Br)c2)CC1]

The synthesis method was the same as that in Embodiment 1.

¹H NMR (400 MHz, DMSO): δ 11.53 (s, 1H), 8.83 (s, 1H), 7.17 (t, J=8.8 Hz, 1H), 7.13 (m, 1H), 6.76 (m, 1H), 6.15 (s, 1H), 3.28 (t, J=7.8 Hz, 2H), 2.88 (s, 3H), 2.85 (t, J=7.8 Hz, 2H), ppm. ¹³C NMR (125 MHz, DMSO): δ 163.9, 158.3, 153.9, 148.2, 145.9, 135.3, 134.4, 112.3, 107.6, 101.2, 48.6, 45.7, 39.8 ppm. MS (EI, m/z): 507 (M⁺+1).

Embodiment 51

(Z)-1-(4-(N-(4-fluorophenyl)-N'-hydroxyaminoiminomethyl)-1,2,5-oxadiazole-3-substituted)-3-phenylurea

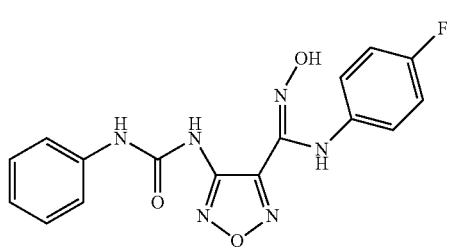 [SMILES: O=C(Nc1ccccc1)Nc1nonc1/C(=N/O)Nc1ccc(F)cc1]

The synthesis method was the same as that in Embodiment 1.

¹H NMR (400 MHz, DMSO): δ 11.46 (s, 1H), 8.80 (s, 1H), 7.83 (d, J=8.4 Hz, 1H), 7.18-7.12 (m, 2H), 7.14-7.01 (m, 4H), 6.73-6.52 (m, 4H), 6.21 (s, 1H), 6.07 (s, 1H) ppm. ¹³C NMR (125 MHz, DMSO): δ 163.7, 160.1, 154.0, 151.3, 148.2, 140.3, 135.2, 134.8, 121.8, 120.6, 119.1, 118.6, 115.7, 114.7 ppm. MS (EI, m/z): 357 (M⁺+1).

Embodiment 52

(Z)-1-(4-(N-(4-fluorophenyl)-N'-hydroxyaminoiminomethyl)-1,2,5-oxadiazole-3-substituted)-3-cyclohexylurea

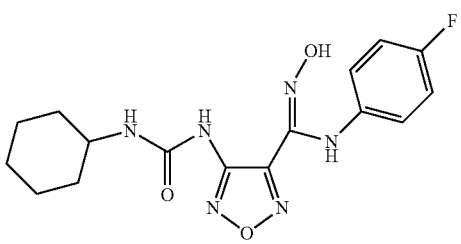 [SMILES: O=C(Nc1nonc1/C(=N/O)Nc1ccc(F)cc1)NC1CCCCC1]

The synthesis method was the same as that in Embodiment 1.

¹H NMR (400 MHz, DMSO): δ 11.44 (s, 1H), 8.85 (s, 1H), 6.79 (d, J=8.2 Hz, 2H), 6.53 (d, J=8.2 Hz, 2H), 6.15 (s, 1H), 3.55 (m, 1H), 1.83-1.79 (m, 2H), 1.60-1.54 (m, 2H), 1.46-1.19 (m, 6H) ppm. ¹³C NMR (125 MHz, DMSO): δ 163.0, 159.1, 154.3, 149.2, 145.7, 135.2, 134.5, 117.6, 107.3, 100.3, 52.1, 31.9, 25.9, 24.8 ppm. MS (EI, m/z): 363 (M⁺+1).

Embodiment 53

(Z)-1-(4-(N-(4-fluorophenyl)-N'-hydroxyaminoiminomethyl)-1,2,5-oxadiazole-3-substituted)-4-(methsulfonyl)piperidine-1-carbamide

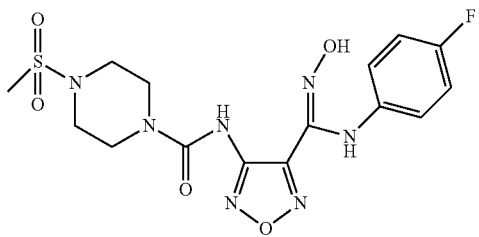 [SMILES: CS(=O)(=O)N1CCN(C(=O)Nc2nonc2/C(=N/O)Nc2ccc(F)cc2)CC1]

The synthesis method was the same as that in Embodiment 1.

¹H NMR (400 MHz, DMSO): δ 11.52 (s, 1H), 8.83 (s, 1H), 6.75 (d, J=8.0 Hz, 2H), 6.50 (d, J=8.0 Hz, 2H), 6.14 (s, 1H), 3.28 (t, J=7.8 Hz, 2H), 2.87 (s, 3H), 2.83 (t, J=7.8 Hz, 2H) ppm. ¹³C NMR (125 MHz, DMSO): δ 163.6, 158.1, 153.8, 148.2, 145.9, 135.2, 134.3, 116.3, 107.6, 101.2, 48.2, 45.5, 39.7 ppm. MS (EI, m/z): 428 (M⁺+1).

Embodiment 54

(Z)-1-(4-(N-(4-fluorophenyl)-N'-hydroxyaminoiminomethyl)-1,2,5-oxadiazole-3-substituted)-3-(4-methoxyphenyl)urea

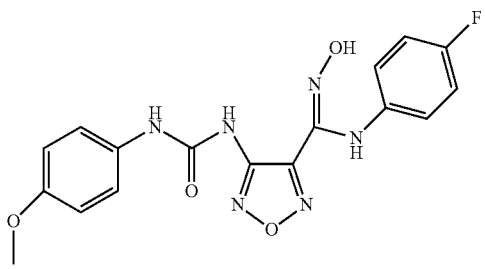 [SMILES: COc1ccc(NC(=O)Nc2nonc2/C(=N/O)Nc2ccc(F)cc2)cc1]

The synthesis method was the same as that in Embodiment 1.

¹H NMR (400 MHz, DMSO): δ 11.42 (s, 1H), 8.83 (s, 1H), 7.53 (d, J=8.6 Hz, 2H), 6.82 (d, J=8.6 Hz, 2H), 6.74 (d, J=8.0 Hz, 2H), 6.51 (d, J=8.0 Hz, 2H), 6.20 (s, 1H), 3.73 (s, 3H) ppm. ¹³C NMR (125 MHz, DMSO): δ 162.1, 158.1, 154.1, 150.2, 148.3, 139.5, 133.6, 130.6, 120.1, 119.6, 119.1, 115.6 54.6 ppm. MS (EI, m/z): 387 (M$^+$+1).

Embodiment 55

(Z)-1-(4-(N-(4-fluorophenyl)-N'-hydroxyaminoiminomethyl)-1,2,5-oxadiazole-3-substituted)-3-(4-aminocyclohexyl)urea

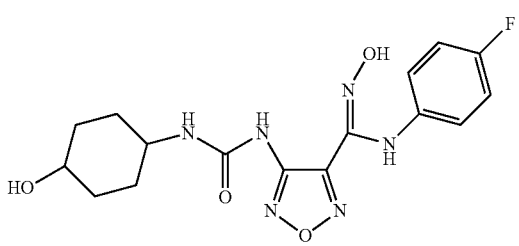 [SMILES: O=C(Nc1nonc1/C(=N/O)Nc1ccc(F)cc1)NC1CCC(O)CC1]

The synthesis method was the same as that in Embodiment 1.

¹H NMR (400 MHz, DMSO): δ 11.48 (s, 1H), 8.83 (s, 1H), 6.76 (d, J=8.0 Hz, 2H), 6.52 (d, J=8.0 Hz, 2H), 6.25 (s, 1H), 3.55 (m, 1H), 3.29 (m, 1H), 1.80-1.75 (m, 2H), 1.66-1.56 (m, 2H) ppm. ¹³C NMR (125 MHz, DMSO): δ 164.3, 159.2, 153.7, 149.3, 145.3, 135.3, 133.9, 112.9, 107.3, 72.8, 49.8, 31.0, 27.1 ppm. MS (EI, m/z): 379 (M$^+$+1).

Embodiment 56

(Z)-1-(4-(N-(3-bromo-4-fluorophenyl)-N'-hydroxyaminoiminomethyl)-1,2,5-oxadiazole-3-substituted)-4-(aminosulfonyl)piperidine-1-carbamide

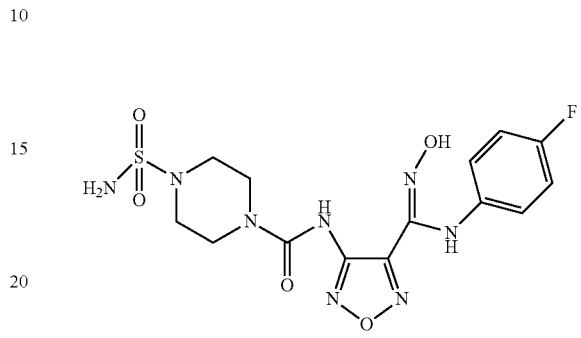

The synthesis method was the same as that in Embodiment 1.

¹H NMR (400 MHz, DMSO): δ 11.53 (s, 1H), 8.83 (s, 1H), 6.70 (d, J=7.8 Hz, 2H), 6.45 (d, J=7.8 Hz, 2H), 6.15 (s, 1H), 3.29 (t, J=7.6 Hz, 2H), 2.83 (t, J=7.6 Hz, 2H) ppm. ¹³C NMR (125 MHz, DMSO): δ 163.8, 158.3, 153.9, 148.2, 145.9, 135.3, 110.3, 107.6, 47.9, 42.9 ppm. MS (EI, m/z): 429 (M$^+$+1).

Embodiment 57

(Z)-1-(4-(N-(4-fluorophenyl)-N'-hydroxyaminoiminomethyl)-1,2,5-oxadiazole-3-substituted)-3-(4-cyanophenyl)urea

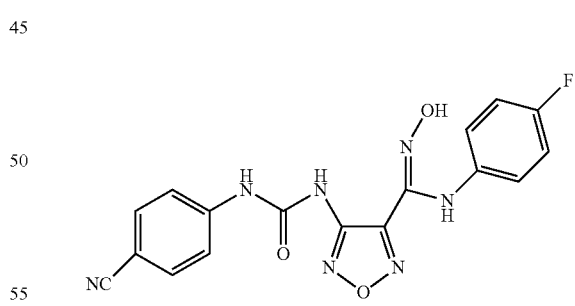

The synthesis method was the same as that in Embodiment 1.

¹H NMR (400 MHz, DMSO): δ 11.43 (s, 1H), 8.85 (s, 1H), 7.37 (d, J=8.4 Hz, 2H), 6.76 (d, J=8.8 Hz, 2H), 6.60 (d, J=8.4 Hz, 2H), 6.50 (d, J=8.8 Hz, 2H), 6.25 (s, 1H) ppm. ¹³C NMR (125 MHz, DMSO): δ 163.1, 152.1, 150.1, 146.3, 141.5, 139.2, 134.6, 131.9, 120.8, 120.1, 118.9, 118.6, 115.7 ppm. MS (EI, m/z): 382 (M$^+$+1).

Embodiment 58

(Z)-1-(4-(N-(3-bromo-4-fluorophenyl)-N'-hydroxyaminoiminomethyl)-furan-3-substituted)-3-(4-methoxyphenyl)urea

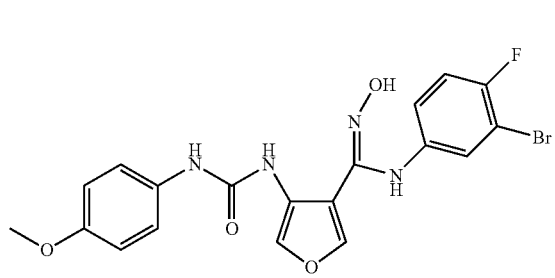 [SMILES: COc1ccc(NC(=O)Nc2cocc2/C(=N/O)Nc2ccc(F)c(Br)c2)cc1]

The synthesis method was the same as that in Embodiment 1.

$^1$H NMR (400 MHz, DMSO): δ 10.33 (s, 1H), 8.80 (s, 1H), 7.53 (d, J=8.6 Hz, 2H), 7.44 (s, 1H), 7.41 (s, 1H), 6.86 (d, J=8.6 Hz, 2H), 6.73 (s, 1H), 6.63 (d, J=8.0 Hz, 1H), 6.43 (d, J=8.0 Hz, 1H), 6.15 (s, 1H), 3.73 (s, 3H) ppm. $^{13}$C NMR (125 MHz, DMSO): δ 161.7, 152.0, 150.1, 146.1, 142.8, 141.7, 141.3, 139.0, 134.3, 131.7, 120.6, 120.1, 118.7, 118.5, 115.6, 55.9 ppm. MS (EI, m/z): 464 (M$^+$+1).

Embodiment 59

(Z)-1-(4-(N-(3-bromo-4-fluorophenyl)-N'-hydroxyaminoiminomethyl)-furan-3-substituted)-3-(3-methoxyphenyl)urea

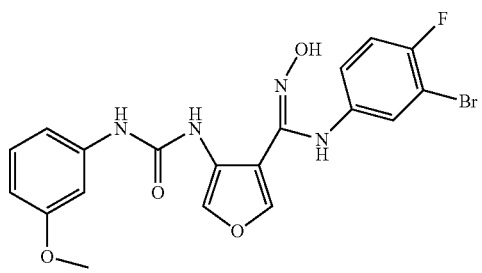 [SMILES: COc1cccc(NC(=O)Nc2cocc2/C(=N/O)Nc2ccc(F)c(Br)c2)c1]

The synthesis method was the same as that in Embodiment 1.

$^1$H NMR (400 MHz, DMSO): δ 10.32 (s, 1H), 8.81 (s, 1H), 7.32 (d, J=7.6 Hz, 1H), 7.43 (s, 1H), 7.40 (s, 1H), 7.19 (s, 1H), 7.13 (m, 1H), 6.80 (s, 1H), 6.70 (d, J=7.0 Hz, 1H), 6.59 (d, J=7.6 Hz, 1H), 6.39 (d, J=7.0 Hz, 1H), 6.15 (s, 1H), 3.72 (s, 3H) ppm. $^{13}$C NMR (125 MHz, DMSO): δ 161.7, 152.1, 150.0, 146.2, 142.8, 141.6, 141.2, 139.0, 134.1, 131.7, 120.5, 120.1, 118.8, 118.5, 115.5, 55.8 ppm. MS (EI, m/z): 464 (M$^+$+1).

Embodiment 60

(Z)-1-(4-(N-(3-bromo-4-fluorophenyl)-N'-hydroxyaminoiminomethyl)-furan-3-substituted)-3-phenylurea

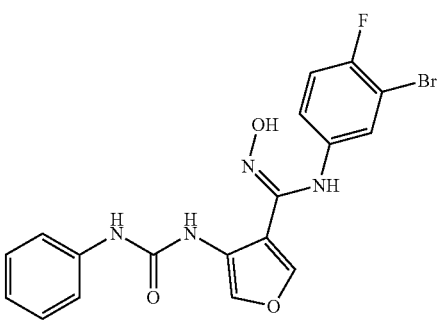 [SMILES: O=C(Nc1ccccc1)Nc1cocc1/C(=N/O)Nc1ccc(F)c(Br)c1]

The synthesis method was the same as that in Embodiment 1.

$^1$H NMR (400 MHz, DMSO): δ 10.30 (s, 1H), 8.78 (s, 1H), 7.60-7.28 (m, 5H), 7.42 (s, 1H), 7.39 (s, 1H), 6.78 (s, 1H), 6.69 (d, J=6.8 Hz, 1H), 6.49 (d, J=6.8 Hz, 1H), 6.15 (s, 1H) ppm. $^{13}$C NMR (125 MHz, DMSO): δ 161.7, 152.1, 150.0, 146.1, 142.7, 141.5, 141.1, 138.9, 134.0, 131.4, 120.3, 120.0, 118.6, 118.1, 115.2 ppm. MS (EI, m/z): 434 (M$^+$+1).

Embodiment 61

(Z)-1-(4-(N-(3-bromo-4-fluorophenyl)-N'-hydroxyaminoiminomethyl)-furan-3-substituted)-3-cyclohexylurea

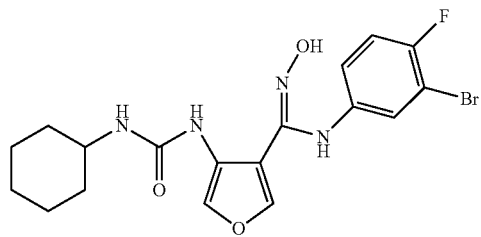 [SMILES: O=C(Nc1cocc1/C(=N/O)Nc1ccc(F)c(Br)c1)NC1CCCCC1]

The synthesis method was the same as that in Embodiment 1.

$^1$H NMR (400 MHz, DMSO): δ 10.29 (s, 1H), 8.76 (s, 1H), 7.41 (s, 1H), 7.39 (s, 1H), 6.76 (s, 1H), 6.66 (d, J=6.8 Hz, 1H), 6.46 (d, J=6.8 Hz, 1H), 6.12 (s, 1H), 1.83-1.78 (m, 2H), 1.63-1.56 (m, 2H), 1.43-1.19 (m, 6H) ppm. $^{13}$C NMR (125 MHz, DMSO): δ 161.7, 152.1, 150.0, 146.1, 142.7, 141.5, 141.1, 138.9, 134.0, 131.4, 120.3, 120.0, 118.6, 118.1, 115.2, 49.5, 33.6, 28.1, 22.5 ppm. MS (EI, m/z): 440 (M$^+$+1).

Embodiment 62

(Z)-1-(4-(N-(3-bromo-4-fluorophenyl)-N'-hydroxyaminoiminomethyl)-furan-3-substituted)-3-cyclopentylurea

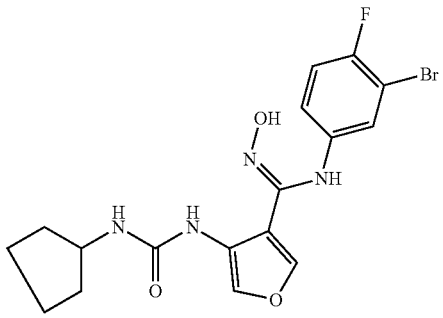 [SMILES: O=C(Nc1cocc1/C(=N/O)Nc1ccc(F)c(Br)c1)NC1CCCC1]

The synthesis method was the same as that in Embodiment 1.

$^1$H NMR (400 MHz, DMSO): δ 10.28 (s, 1H), 8.75 (s, 1H), 7.40 (s, 1H), 7.38 (s, 1H), 6.75 (s, 1H), 6.64 (d, J=6.8 Hz, 1H), 6.43 (d, J=6.8 Hz, 1H), 6.12 (s, 1H), 3.61 (m, 1H), 1.86-1.68 (m, 4H), 1.59-1.49 (m, 4H) ppm. $^{13}$C NMR (125 MHz, DMSO): δ 161.6, 152.2, 150.1, 146.2, 142.8, 141.6, 141.1, 138.9, 134.1, 131.5, 120.3, 120.1, 118.7, 118.2, 115.2, 56.2, 34.6, 24.9 ppm. MS (EI, m/z): 426 (M$^+$+1).

Embodiment 63

(Z)-1-(4-(N-(3-bromo-4-fluorophenyl)-N'-hydroxyaminoiminomethyl)-furan-3-substituted)-3-(4-hydroxycyclohexyl)urea

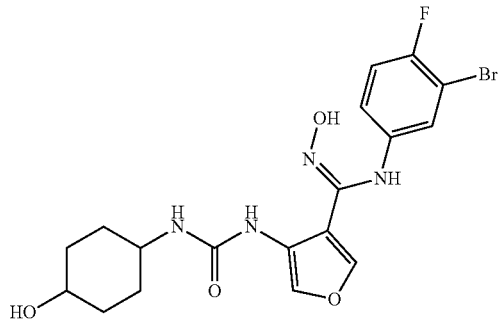

The synthesis method was the same as that in Embodiment 1.

$^1$H NMR (400 MHz, DMSO): δ 10.32 (s, 1H), 8.78 (s, 1H), 7.43 (s, 1H), 7.40 (s, 1H), 6.76 (s, 1H), 6.65 (d, J=6.8 Hz, 1H), 6.44 (d, J=6.8 Hz, 1H), 6.15 (s, 1H), 3.60 (m, 1H), 3.19 (m, 1H), 1.80-1.70 (m, 4H), 1.55-1.49 (m, 4H) ppm. $^{13}$C NMR (125 MHz, DMSO): δ 161.8, 152.4, 150.3, 146.3, 142.8, 141.7, 141.1, 138.9, 134.2, 131.6, 120.4, 120.1, 118.9, 118.3, 115.3, 72.7, 49.8, 31.6, 27.0 ppm. MS (EI, m/z): 456 (M$^+$+1).

Embodiment 64

(Z)-1-(4-(N-(3-bromo-4-fluorophenyl)-N'-hydroxyaminoiminomethyl)-furan-3-substituted)-3-(piperidine-4-substituted)urea

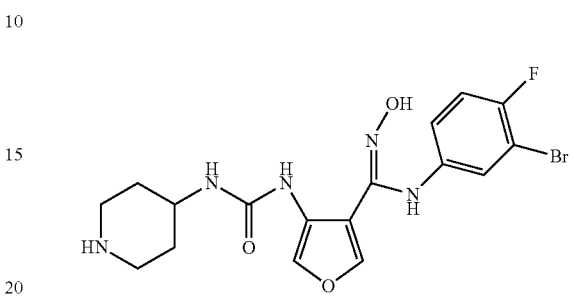

The synthesis method was the same as that in Embodiment 1.

$^1$H NMR (400 MHz, DMSO): δ 10.31 (s, 1H), 8.77 (s, 1H), 7.42 (s, 1H), 7.40 (s, 1H), 6.75 (s, 1H), 6.63 (d, J=6.6 Hz, 1H), 6.43 (d, J=6.6 Hz, 1H), 6.14 (s, 1H), 3.59 (m, 1H), 2.79-2.69 (m, 4H), 1.85-1.63 (m, 4H) ppm. $^{13}$C NMR (125 MHz, DMSO): δ 161.7, 152.2, 150.2, 146.3, 142.7, 141.6, 141.1, 138.8, 134.2, 131.5, 120.3, 120.0, 118.8, 118.3, 115.2, 46.0, 42.8, 32.0 ppm. MS (EI, m/z): 441 (M$^+$+1).

Embodiment 65

(Z)-1-(4-(N-(3-bromo-4-fluorophenyl)-N'-hydroxyaminoiminomethyl)-furan-3-substituted)-3-cyclopentylurea

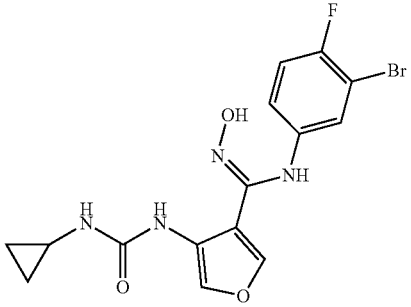 [SMILES: O=C(Nc1cocc1/C(=N/O)Nc1ccc(F)c(Br)c1)NC1CC1]

The synthesis method was the same as that in Embodiment 1.

$^1$H NMR (400 MHz, DMSO): δ 10.20 (s, 1H), 8.72 (s, 1H), 7.39 (s, 1H), 7.36 (s, 1H), 6.73 (s, 1H), 6.62 (d, J=6.6 Hz, 1H), 6.41 (d, J=6.6 Hz, 1H), 6.11 (s, 1H), 2.32 (m, 1H), 0.59-0.39 (m, 4H) ppm. $^{13}$C NMR (125 MHz, DMSO): δ 161.3, 152.0, 150.0, 145.9, 142.5, 141.3, 140.8, 138.7, 134.0, 131.2, 120.3, 119.8, 118.5, 118.0, 115.0, 26.5, 7.9 ppm. MS (EI, m/z): 398 (M$^+$+1).

Embodiment 66

(Z)-1-(4-(N-(3-bromo-4-fluorophenyl)-N'-hydroxyaminoiminomethyl)-furan-3-substituted)-3-(4-aminocyclohexyl)urea

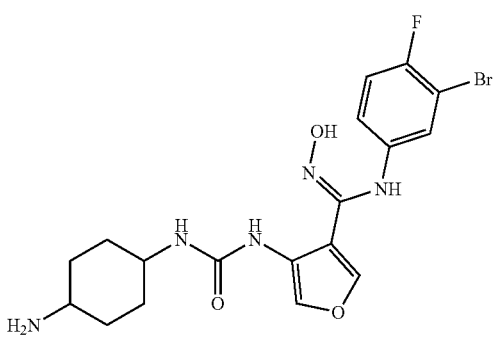 [SMILES: NC1CCC(NC(=O)Nc2cocc2/C(=N/O)Nc2ccc(F)c(Br)c2)CC1]

The synthesis method was the same as that in Embodiment 1.

¹H NMR (400 MHz, DMSO): δ 10.30 (s, 1H), 8.76 (s, 1H), 7.42 (s, 1H), 7.40 (s, 1H), 6.73 (s, 1H), 6.63 (d, J=6.8 Hz, 1H), 6.42 (d, J=6.8 Hz, 1H), 6.14 (s, 1H), 3.55 (m, 1H), 2.57 (m, 1H), 1.80-1.70 (m, 4H), 1.65-1.53 (m, 4H) ppm. ¹³C NMR (125 MHz, DMSO): δ 161.6, 152.2, 150.1, 146.1, 142.5, 141.6, 141.1, 138.7, 134.1, 131.5, 120.3, 120.0, 118.8, 118.1, 115.1, 50.3, 49.6, 31.0, 28.3 ppm. MS (EI, m/z): 455 (M$^+$+1).

Embodiment 67

(Z)-1-(4-(N-(3-bromo-4-fluorophenyl)-N'-hydroxyaminoiminomethyl)-furan-3-substituted)-3-(3-aminopropyl)urea

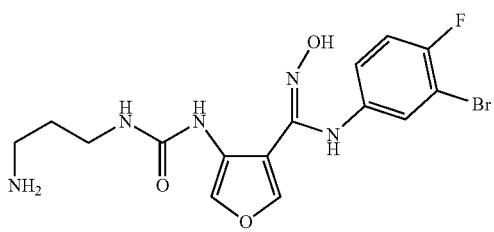 [SMILES: NCCCNC(=O)Nc1cocc1/C(=N/O)Nc1ccc(F)c(Br)c1]

The synthesis method was the same as that in Embodiment 1.

¹H NMR (400 MHz, DMSO): δ 10.30 (s, 1H), 8.76 (s, 1H), 7.42 (s, 1H), 7.40 (s, 1H), 6.73 (s, 1H), 6.63 (d, J=6.8 Hz, 1H), 6.42 (d, J=6.8 Hz, 1H), 6.14 (s, 1H), 3.18 (t, J=6.6 Hz, 2H), 2.66 (t, J=6.6 Hz, 2H), 1.81 (m, 2H) ppm. ¹³C NMR (125 MHz, DMSO): δ 161.6, 152.2, 150.1, 146.1, 142.5, 141.6, 141.1, 138.7, 134.1, 131.5, 120.3, 120.0, 118.8, 118.1, 115.1, 50.3, 49.6, 31.0, 28.3 ppm. MS (EI, m/z): 415 (M$^+$+1).

Embodiment 68

(Z)-1-(4-(N-(3-bromo-4-fluorophenyl)-N'-hydroxyaminoiminomethyl)-furan-3-substituted)+3-(2-hydroxyethyl)urea

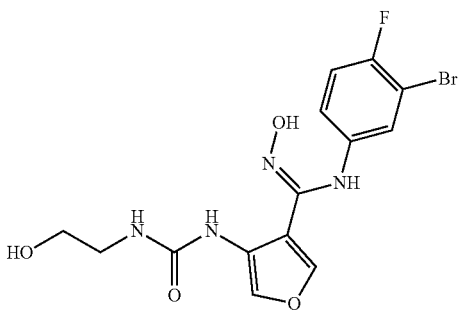 [SMILES: O=C(NCCO)Nc1cocc1/C(=N/O)Nc1ccc(F)c(Br)c1]

The synthesis method was the same as that in Embodiment 1.

¹H NMR (400 MHz, DMSO): δ 10.32 (s, 1H), 8.76 (s, 1H), 7.43 (s, 1H), 7.41 (s, 1H), 6.75 (s, 1H), 6.64 (d, J=6.8 Hz, 1H), 6.43 (d, J=6.8 Hz, 1H), 6.16 (s, 1H), 3.79 (t, J=6.8 Hz, 2H), 3.35 (t, J=6.8 Hz, 2H) ppm. ¹³C NMR (125 MHz, DMSO): δ 161.7, 152.3, 150.2, 146.2, 142.6, 141.7, 141.2, 138.7, 134.2, 131.6, 120.4, 120.1, 118.9, 118.2, 115.2, 60.6, 43.7 ppm. MS (EI, m/z): 402 (M$^+$+1).

Embodiment 69

(Z)-1-(4-(N-(3-bromo-4-fluorophenyl)-N'-hydroxyaminoiminomethyl)-furan-3-substituted)-3-(2-aminoethyl)urea

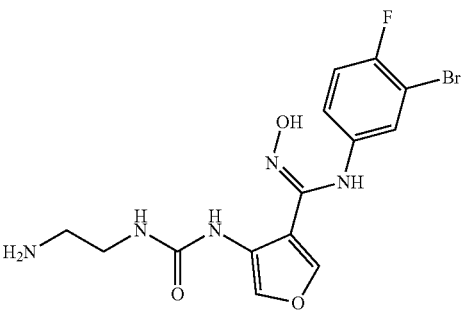 [SMILES: NCCNC(=O)Nc1cocc1/C(=N/O)Nc1ccc(F)c(Br)c1]

The synthesis method was the same as that in Embodiment 1.

¹H NMR (400 MHz, DMSO): δ 10.29 (s, 1H), 8.75 (s, 1H), 7.42 (s, 1H), 7.40 (s, 1H), 6.73 (s, 1H), 6.62 (d, J=6.8 Hz, 1H), 6.42 (d, J=6.8 Hz, 1H), 6.15 (s, 1H), 3.42 (t, J=6.6 Hz, 2H), 2.91 (t, J=6.6 Hz, 2H) ppm. ¹³C NMR (125 MHz, DMSO): δ 161.6, 152.2, 150.1, 146.1, 142.5, 141.6, 141.1, 138.7, 134.1, 131.5, 120.3, 120.0, 118.8, 118.1, 115.1, 45.0, 40.1 ppm. MS (EI, m/z): 401 (M$^+$+1).

Embodiment 70

(Z)-1-(4-(N-(3-bromo-4-fluorophenyl)-N'-hydroxyaminoiminomethyl)-furan-3-substituted)-3-propylurea

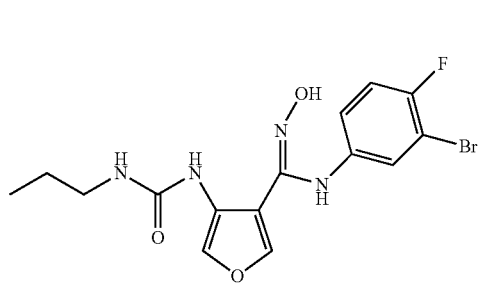 [SMILES: CCCNC(=O)Nc1cocc1/C(=N/O)Nc1ccc(F)c(Br)c1]

The synthesis method was the same as that in Embodiment 1.

$^1$H NMR (400 MHz, DMSO): δ 10.27 (s, 1H), 8.75 (s, 1H), 7.41 (s, 1H), 7.39 (s, 1H), 6.72 (s, 1H), 6.62 (d, J=6.8 Hz, 1H), 6.41 (d, J=6.8 Hz, 1H), 6.13 (s, 1H), 3.15 (t, J=6.6 Hz, 2H), 1.59 (m, 2H), 0.97 (t, J=6.6 Hz, 3H) ppm. $^{13}$C NMR (125 MHz, DMSO): δ 161.3, 152.0, 150.0, 145.8, 142.2, 141.3, 140.8, 138.5, 134.0, 131.2, 120.0, 119.7, 118.5, 117.8, 115.0, 44.7, 22.7, 10.8 ppm. MS (EI, m/z): 400 (M$^+$+1).

Embodiment 71

(Z)-1-(4-(N-(3-bromo-4-fluorophenyl)-N'-hydroxyaminoiminomethyl)-furan-3-substituted)-3-isopropylurea

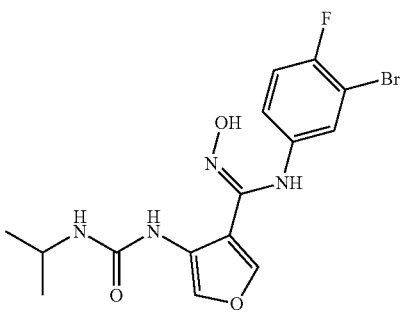 [SMILES: CC(C)NC(=O)Nc1cocc1/C(=N/O)Nc1ccc(F)c(Br)c1]

The synthesis method was the same as that in Embodiment 1.

$^1$H NMR (400 MHz, DMSO): δ 10.27 (s, 1H), 8.75 (s, 1H), 7.41 (s, 1H), 7.39 (s, 1H), 6.72 (s, 1H), 6.62 (d, J=6.8 Hz, 1H), 6.41 (d, J=6.8 Hz, 1H), 6.13 (s, 1H), 3.94 (m, 2H), 1.25 (d, J=6.8 Hz, 6H) ppm. $^{13}$C NMR (125 MHz, DMSO): δ 161.4, 152.1, 150.0, 145.9, 142.3, 141.3, 140.9, 138.6, 134.1, 131.3, 120.1, 119.8, 118.6, 117.9, 115.1, 43.2, 22.8 ppm. MS (EI, m/z): 400 (M$^+$+1).

Embodiment 72

(Z)-1-(4-(N-(3-bromo-4-fluorophenyl)-N'-hydroxyaminoiminomethyl)-furan-3-substituted)-3-(2-methamidoethyl)urea

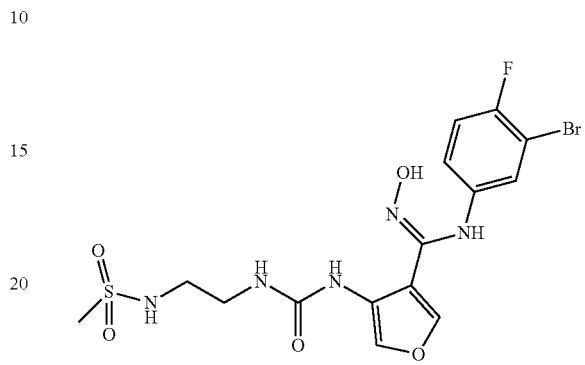

The synthesis method was the same as that in Embodiment 1.

$^1$H NMR (400 MHz, DMSO): δ 10.29 (s, 1H), 8.76 (s, 1H), 7.43 (s, 1H), 7.41 (s, 1H), 6.74 (s, 1H), 6.63 (d, J=6.8 Hz, 1H), 6.43 (d, J=6.8 Hz, 1H), 6.16 (s, 1H), 3.45 (t, J=6.8 Hz, 2H), 2.94 (t, J=6.8 Hz, 2H), 2.83 (s, 3H) ppm. $^{13}$C NMR (125 MHz, DMSO): δ 161.6, 152.2, 150.1, 146.1, 142.5, 141.6, 141.1, 138.7, 134.1, 131.5, 120.3, 120.0, 118.8, 118.1, 115.1, 42.9, 41.7, 40.3 ppm. MS (EI, m/z): 479 (M$^+$+1).

Embodiment 73

(Z)-1-(4-(N-(3-bromo-4-fluorophenyl)-N'-hydroxyaminoiminomethyl)-furan-3-substituted)-3-(4-aminoindole)urea

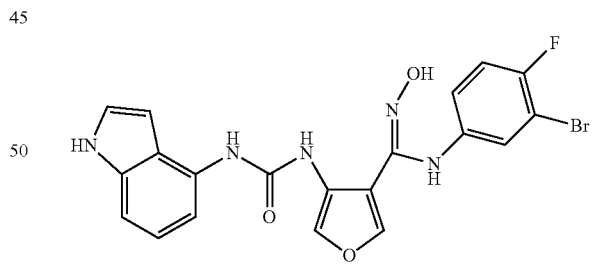

The synthesis method was the same as that in Embodiment 1.

$^1$H NMR (400 MHz, DMSO): δ 10.29 (s, 1H), 8.75 (s, 1H), 7.42 (s, 1H), 7.40 (s, 1H), 7.38 (d, J=7.6 Hz, 1H), 7.27 (d, J=7.0 Hz, 1H), 7.14 (d, J=7.6 Hz, 1H), 7.06 (m, 1H), 6.73 (s, 1H), 6.62 (d, J=6.8 Hz, 1H), 6.49 (d, J=7.0 Hz, 1H), 6.42 (d, J=6.8 Hz, 1H), 6.15 (s, 1H) ppm. $^{13}$C NMR (125 MHz, DMSO): δ 161.6, 152.2, 150.1, 146.1, 142.5, 141.6, 141.1, 138.7, 135.7, 134.1, 131.5, 130.2, 124.3, 120.5, 120.3, 120.0, 118.8, 118.1, 115.1, 114.7, 112.3, 106.7, 102.5 ppm. MS (EI, m/z): 473 (M$^+$+1).

Embodiment 74

(Z)-1-(4-(N-(3-bromo-4-fluorophenyl)-N'-hydroxyaminoiminomethyl)-furan-3-substituted)-3-(3-aminoindole)urea

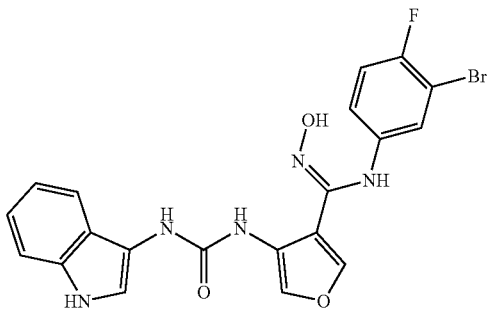 [SMILES: O=C(Nc1cocc1/C(=N/O)Nc1ccc(F)c(Br)c1)Nc1c[nH]c2ccccc12]

The synthesis method was the same as that in Embodiment 1.

$^1$H NMR (400 MHz, DMSO): δ 10.29 (s, 1H), 10.11 (s, 1H), 8.75 (s, 1H), 7.60 (d, J=6.6 Hz, 1H), 7.45 (d, J=6.6 Hz, 1H), 7.42 (s, 1H), 7.40 (s, 1H), 7.37 (s, 1H), 7.12-7.07 (m, 2H), 6.73 (s, 1H), 6.62 (d, J=6.8 Hz, 1H), 6.42 (d, J=6.8 Hz, 1H), 6.15 (s, 1H) ppm. $^{13}$C NMR (125 MHz, DMSO): δ 161.6, 152.2, 150.1, 146.1, 142.5, 141.6, 141.1, 138.7, 135.6, 134.1, 131.5, 124.1, 12.2, 120.6, 120.3, 120.0, 119.0, 118.8, 118.1, 115.1, 111.1 ppm. MS (EI, m/z): 473 (M$^+$+1).

Embodiment 75

(Z)-1-(4-(N-(3-bromo-4-fluorophenyl)-N'-hydroxyaminoiminomethyl)-furan-3-substituted)-3-(3-aminopyridine)urea

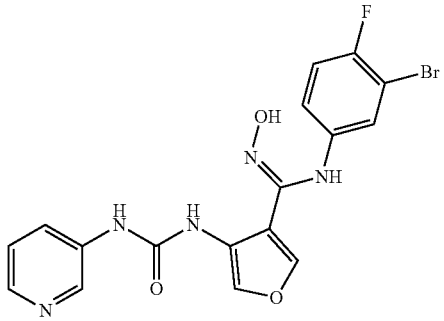 [SMILES: O=C(Nc1cccnc1)Nc1cocc1/C(=N/O)Nc1ccc(F)c(Br)c1]

The synthesis method was the same as that in Embodiment 1.

$^1$H NMR (400 MHz, DMSO): δ 10.29 (s, 1H), 8.75 (s, 1H), 8.53 (s, 1H), 8.23 (d, J=6.6 Hz, 1H), 7.42 (s, 1H), 7.40 (s, 1H), 7.37 (m, 1H), 7.26 (d, J=6.6 Hz, 1H), 6.72 (s, 1H), 6.62 (d, J=6.8 Hz, 1H), 6.41 (d, J=6.8 Hz, 1H), 6.14 (s, 1H) ppm. $^{13}$C NMR (125 MHz, DMSO): δ 161.6, 152.2, 150.1, 146.1, 142.5, 141.6, 141.1, 138.9, 138.7, 137.6, 134.4, 134.1, 131.5, 124.7, 122.8, 120.3, 120.0, 118.7, 118.1, 115.0 ppm. MS (EI, m/z): 435 (M$^+$+1).

Embodiment 76

(Z)-1-(4-(N-(3-bromo-4-fluorophenyl)-N'-hydroxyaminoiminomethyl)-furan-3-substituted)-3-(1H-pyrrole-3-substituted)urea

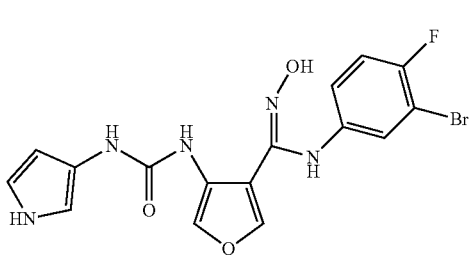 [SMILES: O=C(Nc1cc[nH]c1)Nc1cocc1/C(=N/O)Nc1ccc(F)c(Br)c1]

The synthesis method was the same as that in Embodiment 1.

$^1$H NMR (400 MHz, DMSO): δ 10.29 (s, 1H), 8.75 (s, 1H), 7.42 (s, 1H), 7.40 (s, 1H), 6.73 (s, 1H), 6.69 (s, 1H), 6.65 (d, J=6.6 Hz, 1H), 6.62 (d, J=6.8 Hz, 1H), 6.42 (d, J=6.8 Hz, 1H), 6.15 (s, 1H), 6.10 (d, J=6.6 Hz, 1H) ppm. $^{13}$C NMR (125 MHz, DMSO): δ 161.6, 152.2, 150.1, 146.1, 142.5, 141.6, 141.1, 138.7, 134.1, 131.9, 131.5, 120.3, 120.0, 118.8, 118.1, 117.5, 115.1, 109.3, 108.0 ppm. MS (EI, m/z): 423 (M$^+$+1).

Embodiment 77

(Z)-1-(4-(N-(3-bromo-4-fluorophenyl)-N'-hydroxyaminoiminomethyl)-furan-3-substituted)-3-(1H-pyrrole-3-substituted)urea

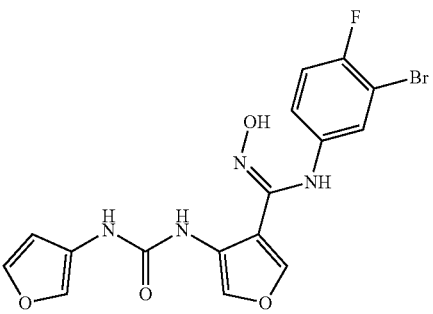 [SMILES: O=C(Nc1ccoc1)Nc1cocc1/C(=N/O)Nc1ccc(F)c(Br)c1]

The synthesis method was the same as that in Embodiment 1.

$^1$H NMR (400 MHz, DMSO): δ 10.29 (s, 1H), 8.75 (s, 1H), 7.42 (s, 1H), 7.40 (s, 1H), 7.38 (s, 1H), 7.33 (d, J=6.6 Hz, 1H), 6.73 (s, 1H), 6.62 (d, J=6.8 Hz, 1H), 6.42 (d, J=6.8 Hz, 1H), 6.38 (d, J=6.6 Hz, 1H), 6.15 (s, 1H) ppm. $^{13}$C NMR (125 MHz, DMSO): δ 161.6, 152.2, 150.1, 146.1, 144.2, 142.5, 141.6, 141.1, 138.7, 134.1, 131.5, 130.5, 124.7, 120.3, 120.0, 118.8, 118.1, 115.1, ppm. MS (EI, m/z): 424 (M$^+$+1).

Embodiment 78

(Z)-1-(4-(N-(3-bromo-4-fluorophenyl)-N'-hydroxyaminoiminomethyl)-furan-3-substituted)-3-(1H-pyrrole-3-substituted)urea

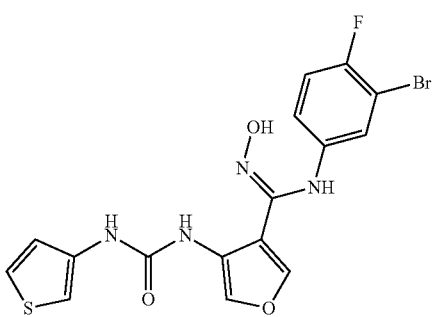

The synthesis method was the same as that in Embodiment 1.

$^1$H NMR (400 MHz, DMSO): δ 10.29 (s, 1H), 8.75 (s, 1H), 7.42 (s, 1H), 7.40 (s, 1H), 6.96 (d, J=6.6 Hz, 1H), 6.73 (s, 1H), 6.62 (d, J=6.8 Hz, 1H), 6.48 (d, J=6.6 Hz, 1H), 6.42 (d, J=6.8 Hz, 1H), 6.15 (s, 1H), 6.10 (s, 1H) ppm. $^{13}$C NMR (125 MHz, DMSO): δ 161.6, 152.2, 150.1, 146.1, 142.5, 141.6, 141.1, 138.7, 134.1, 131.5, 124.6, 120.4, 120.1, 118.8, 118.1, 116.0, 115.1, 86.8 ppm. MS (EI, m/z): 440 (M$^+$+1).

Embodiment 79

(Z)-1-(4-(N-(3-bromo-4-fluorophenyl)-N'-hydroxyaminoiminomethyl)-isoxazole-3-substituted)-3-(4-methoxyphenyl)urea

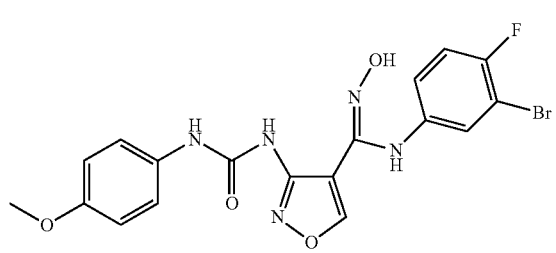 [SMILES: COc1ccc(NC(=O)Nc2nocc2/C(=N/O)Nc2ccc(F)c(Br)c2)cc1]

The synthesis method was the same as that in Embodiment 1.

$^1$H NMR (400 MHz, DMSO): δ 10.28 (s, 1H), 8.75 (s, 1H), 7.53 (d, J=7.2 Hz, 2H), 7.48 (s, 1H), 6.78 (d, J=7.2 Hz, 2H), 6.73 (s, 1H), 6.62 (d, J=6.8 Hz, 1H), 6.41 (d, J=6.8 Hz, 1H), 6.12 (s, 1H), 3.73 (s, 3H) ppm. 13C NMR (125 MHz, DMSO): δ 161.3, 156.3, 152.8, 152.1, 150.1, 146.0, 141.1, 138.5, 134.1, 131.2, 128.2, 122.6, 120.3, 120.0, 118.6, 118.0, 115.1, 114.5, 57.8 ppm. MS (EI, m/z): 465 (M$^+$+1).

Embodiment 80

(Z)-1-(4-(N-(3-bromo-4-fluorophenyl)-N'-hydroxyaminoiminomethyl)-isoxazole-3-substituted)-3-(3-methoxyphenyl)urea

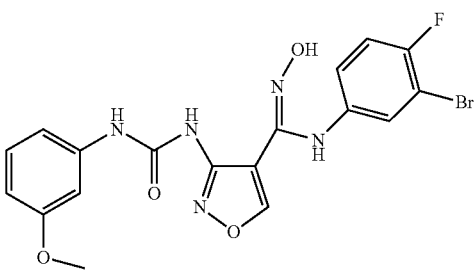 [SMILES: COc1cccc(NC(=O)Nc2nocc2/C(=N/O)Nc2ccc(F)c(Br)c2)c1]

The synthesis method was the same as that in Embodiment 1.

$^1$H NMR (400 MHz, DMSO): δ 10.28 (s, 1H), 8.75 (s, 1H), 7.48 (s, 1H), 7.20 (d, J=6.6 Hz, 1H), 7.17 (s, 1H), 7.13 (m, 1H), 6.73 (s, 1H), 6.62 (d, J=6.8 Hz, 1H), 6.51 (d, J=6.6 Hz, 1H), 6.41 (d, J=6.8 Hz, 1H), 6.12 (s, 1H), 3.70 (s, 3H) ppm. $^{13}$C NMR (125 MHz, DMSO): δ 161.3, 160.9, 152.8, 152.1, 150.1, 146.0, 141.1, 138.5, 136.9, 134.1, 131.2, 130.0, 120.3, 120.0, 118.6, 118.0, 115.1, 113.9, 109.9, 104.8, 55.9 ppm. MS (EI, m/z): 465 (M$^+$+1).

Embodiment 81

(Z)-1-(4-(N-(3-bromo-4-fluorophenyl)-N'-hydroxyaminoiminomethyl)-isoxazole-3-substituted)-3-phenylurea

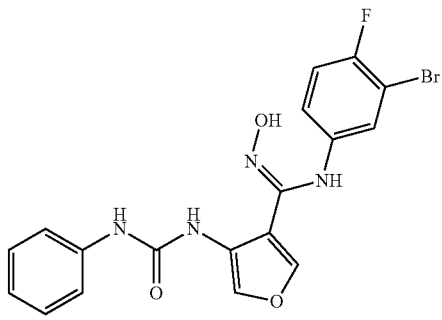 [SMILES: O=C(Nc1ccccc1)Nc1cocc1/C(=N/O)Nc1ccc(F)c(Br)c1]

The synthesis method was the same as that in Embodiment 1.

$^1$H NMR (400 MHz, DMSO): δ 10.28 (s, 1H), 8.75 (s, 1H), 7.48 (s, 1H), 7.43-7.22 (m, 5H), 6.73 (s, 1H), 6.62 (d, J=6.8 Hz, 1H), 6.41 (d, J=6.8 Hz, 1H), 6.12 (s, 1H) ppm. $^{13}$C NMR (125 MHz, DMSO): δ 161.3, 152.8, 152.1, 150.1, 146.0, 141.1, 138.5, 135.9, 134.1, 131.2, 129.0, 124.5, 121.6, 120.3, 120.0, 118.6, 118.0, 115.1 ppm. MS (EI, m/z): 435 (M$^+$+1).

Embodiment 82

(Z)-1-(4-(N-(3-bromo-4-fluorophenyl)-N'-hydroxyaminoiminomethyl)-isoxazole-3-substituted)-3-(cyclohexyl)urea

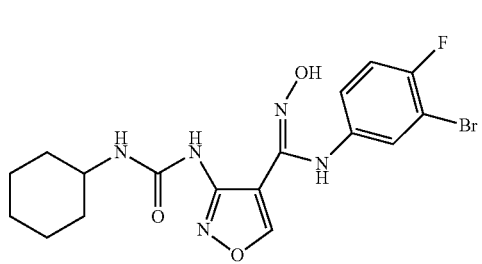 [SMILES: O=C(Nc1nocc1/C(=N/O)Nc1ccc(F)c(Br)c1)NC1CCCCC1]

The synthesis method was the same as that in Embodiment 1.

$^1$H NMR (400 MHz, DMSO): δ 10.28 (s, 1H), 8.75 (s, 1H), 7.48 (s, 1H), 6.73 (s, 1H), 6.62 (d, J=6.8 Hz, 1H), 6.41 (d, J=6.8 Hz, 1H), 6.12 (s, 1H), 3.54 (m, 1H), 1.79-1.55 (m, 4H), 1.49-1.38 (m, 6H) ppm. $^{13}$C NMR (125 MHz, DMSO): δ 161.3, 152.8, 152.1, 150.1, 146.0, 141.1, 138.5, 134.1, 131.2, 120.3, 120.0, 118.6, 118.0, 115.1, 49.6, 33.3, 28.0, 22.5 ppm. MS (EI, m/z): 441 (M$^+$+1).

Embodiment 83

(Z)-1-(4-(N-(3-bromo-4-fluorophenyl)-N'-hydroxyaminoiminomethyl)-isoxazole-3-substituted)-3-(cyclopentyl)urea

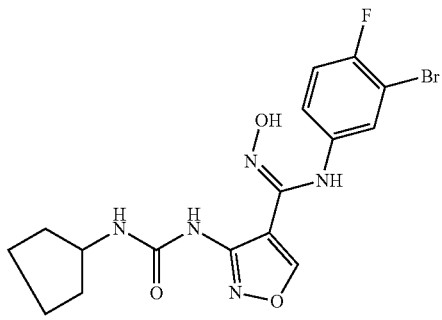 [SMILES: O=C(Nc1nocc1/C(=N/O)Nc1ccc(F)c(Br)c1)NC1CCCC1]

The synthesis method was the same as that in Embodiment 1.

$^1$H NMR (400 MHz, DMSO): δ 10.28 (s, 1H), 8.75 (s, 1H), 7.48 (s, 1H), 6.73 (s, 1H), 6.62 (d, J=6.8 Hz, 1H), 6.41 (d, J=6.8 Hz, 1H), 6.12 (s, 1H), 3.61 (m, 1H), 1.89-1.65 (m, 4H), 1.55-1.46 (m, 4H) ppm. $^{13}$C NMR (125 MHz, DMSO): δ 161.3, 152.8, 152.1, 150.1, 146.0, 141.1, 138.5, 134.1, 131.2, 120.3, 120.0, 118.6, 118.0, 115.1, 56.2, 34.4, 24.9 ppm. MS (EI, m/z): 427 (M$^+$+1).

Embodiment 84

(Z)-1-(4-(N-(3-bromo-4-fluorophenyl)-N'-hydroxyaminoiminomethyl)-isoxazole-3-substituted)-3-(4-hydroxycyclohexyl)urea

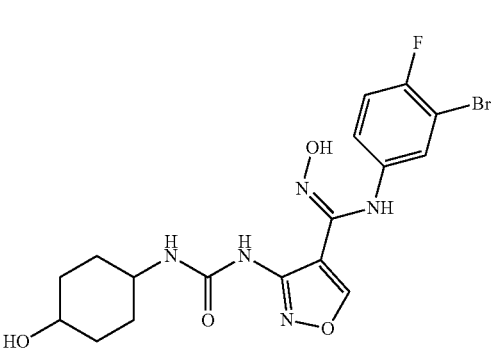

The synthesis method was the same as that in Embodiment 1.

$^1$H NMR (400 MHz, DMSO): δ 10.29 (s, 1H), 8.76 (s, 1H), 7.49 (s, 1H), 6.74 (s, 1H), 6.63 (d, J=6.8 Hz, 1H), 6.42 (d, J=6.8 Hz, 1H), 6.13 (s, 1H), 3.59 (m, 1H), 3.22 (m, 1H), 1.77-1.49 (m, 8H) ppm. $^{13}$C NMR (125 MHz, DMSO): δ 161.3, 152.8, 152.1, 150.1, 146.0, 141.1, 138.5, 134.1, 131.2, 120.3, 120.0, 118.6, 118.0, 115.1, 72.9, 49.8, 31.0, 27.1 ppm. MS (EI, m/z): 457 (M$^+$+1).

Embodiment 85

(Z)-1-(4-(N-(3-bromo-4-fluorophenyl)-N'-hydroxyaminoiminomethyl)-isoxazole-3-substituted)-3-(piperidine-4-substituted)urea

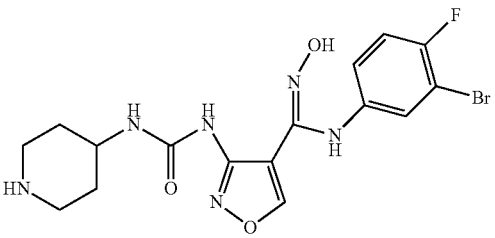 [SMILES: O=C(Nc1nocc1/C(=N/O)Nc1ccc(F)c(Br)c1)NC1CCNCC1]

The synthesis method was the same as that in Embodiment 1.

$^1$H NMR (400 MHz, DMSO): δ 10.28 (s, 1H), 8.75 (s, 1H), 7.48 (s, 1H), 6.73 (s, 1H), 6.62 (d, J=6.8 Hz, 1H), 6.41 (d, J=6.8 Hz, 1H), 6.12 (s, 1H), 3.61 (m, 1H), 2.79-2.69 (m, 4H), 1.85-1.60 (m, 4H) ppm. $^{13}$C NMR (125 MHz, DMSO): δ 161.3, 152.8, 152.1, 150.1, 146.0, 141.1, 138.5, 134.1, 131.2, 120.3, 120.0, 118.6, 118.0, 115.1, 46.0, 42.9, 32.0 ppm. MS (EI, m/z): 442 (M$^+$+1).

Embodiment 86

(Z)-1-(4-(N-(3-bromo-4-fluorophenyl)-N'-hydroxyaminoiminomethyl)-isoxazole-3-substituted)-3-(cyclopropyl)urea

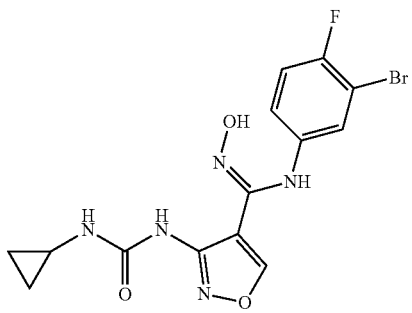 [SMILES: O=C(Nc1nocc1/C(=N/O)Nc1ccc(F)c(Br)c1)NC1CC1]

The synthesis method was the same as that in Embodiment 1.

¹H NMR (400 MHz, DMSO): δ 10.28 (s, 1H), 8.75 (s, 1H), 7.48 (s, 1H), 6.73 (s, 1H), 6.62 (d, J=6.8 Hz, 1H), 6.41 (d, J=6.8 Hz, 1H), 6.12 (s, 1H), 2.35 (m, 1H), 0.56-0.33 (m, 4H) ppm. ¹³C NMR (125 MHz, DMSO): δ 161.1, 152.6, 152.1, 150.1, 146.0, 141.1, 138.3, 134.1, 131.2, 120.2, 120.0, 118.6, 118.0, 115.1, 26.3, 7.1 ppm. MS (EI, m/z): 399 (M⁺+1).

Embodiment 87

(Z)-1-(4-(N-(3-bromo-4-fluorophenyl)-N'-hydroxyaminoiminomethyl)-isoxazole-3-substituted)-3-(4-aminocyclohexyl)urea

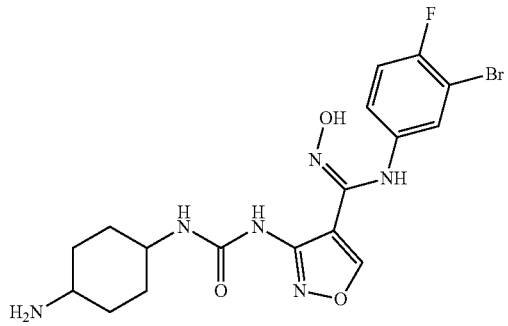 [SMILES: NC1CCC(NC(=O)Nc2nocc2/C(=N/O)Nc2ccc(F)c(Br)c2)CC1]

The synthesis method was the same as that in Embodiment 1.

¹H NMR (400 MHz, DMSO): δ 10.28 (s, 1H), 8.75 (s, 1H), 7.48 (s, 1H), 6.73 (s, 1H), 6.62 (d, J=6.8 Hz, 1H), 6.41 (d, J=6.8 Hz, 1H), 6.12 (s, 1H), 3.58 (m, 1H), 2.59 (m, 1H), 1.80-1.53 (m, 8H) ppm. ¹³C NMR (125 MHz, DMSO): δ 161.3, 152.8, 152.1, 150.1, 146.0, 141.1, 138.5, 134.1, 131.2, 120.3, 120.0, 118.6, 118.0, 115.0, 50.3, 49.6, 31.0, 28.3 ppm. MS (EI, m/z): 456 (M⁺+1).

Embodiment 88

(Z)-1-(4-(N-(3-bromo-4-fluorophenyl)-N'-hydroxyaminoiminomethyl)-isoxazole-3-substituted)-3-(3-propyl)urea

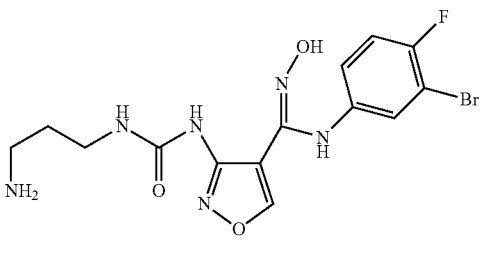 [SMILES: NCCCNC(=O)Nc1nocc1/C(=N/O)Nc1ccc(F)c(Br)c1]

The synthesis method was the same as that in Embodiment 1.

¹H NMR (400 MHz, DMSO): δ 10.28 (s, 1H), 8.75 (s, 1H), 7.48 (s, 1H), 6.73 (s, 1H), 6.62 (d, J=6.8 Hz, 1H), 6.41 (d, J=6.8 Hz, 1H), 6.12 (s, 1H), 3.16 (d, J=6.8 Hz, 2H), 2.66 (d, J=6.6 Hz, 1H), 1.82 (m, 2H) ppm. ¹³C NMR (125 MHz, DMSO): δ 161.3, 152.8, 152.1, 150.1, 146.0, 141.1, 138.5, 134.1, 131.2, 120.3, 120.0, 118.6, 118.0, 115.1, 39.6, 38.8, 31.0 ppm. MS (EI, m/z): 416 (M⁺+1).

Embodiment 89

(Z)-1-(4-(N-(3-bromo-4-fluorophenyl)-N'-hydroxyaminoiminomethyl)-isoxazole-3-substituted)+3-(2-hydroxyethyl)urea

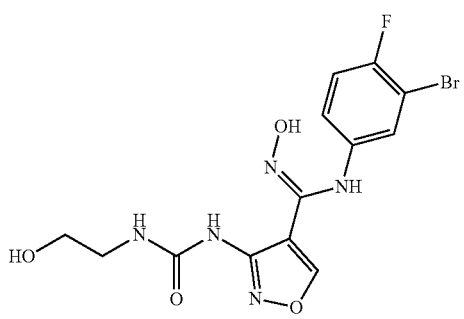 [SMILES: O=C(NCCO)Nc1nocc1/C(=N/O)Nc1ccc(F)c(Br)c1]

The synthesis method was the same as that in Embodiment 1.

¹H NMR (400 MHz, DMSO): δ 10.28 (s, 1H), 8.75 (s, 1H), 7.48 (s, 1H), 6.73 (s, 1H), 6.62 (d, J=6.8 Hz, 1H), 6.41 (d, J=6.8 Hz, 1H), 6.12 (s, 1H), 3.79 (d, J=6.8 Hz, 2H), 3.63 (d, J=6.8 Hz, 1H) ppm. ¹³C NMR (125 MHz, DMSO): δ 161.3, 152.8, 152.1, 150.1, 146.0, 141.1, 138.5, 134.1, 131.2, 120.3, 120.0, 118.6, 118.0, 115.1, 60.6, 43.8 ppm. MS (EI, m/z): 403 (M⁺+1).

Embodiment 90

(Z)-1-(4-(N-(3-bromo-4-fluorophenyl)-N'-hydroxyaminoiminomethyl)-isoxazole-3-substituted)+3-(2-aminoethyl)urea

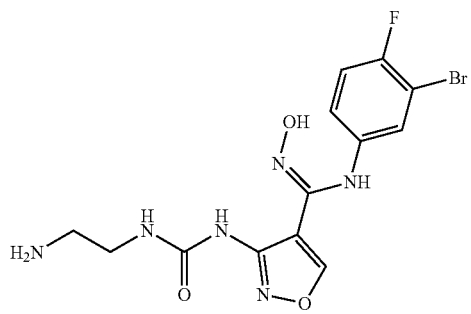 [SMILES: NCCNC(=O)Nc1nocc1/C(=N/O)Nc1ccc(F)c(Br)c1]

The synthesis method was the same as that in Embodiment 1.

$^1$H NMR (400 MHz, DMSO): δ 10.28 (s, 1H), 8.75 (s, 1H), 7.48 (s, 1H), 6.73 (s, 1H), 6.62 (d, J=6.8 Hz, 1H), 6.41 (d, J=6.8 Hz, 1H), 6.12 (s, 1H), 3.42 (d, J=6.6 Hz, 2H), 2.91 (d, J=6.6 Hz, 2H) ppm. $^{13}$C NMR (125 MHz, DMSO): δ 161.3, 152.8, 152.1, 150.1, 146.0, 141.1, 138.5, 134.1, 131.2, 120.3, 120.0, 118.6, 118.0, 115.1, 45.1, 40.2 ppm. MS (EI, m/z): 402 (M$^+$+1).

Embodiment 91

(Z)-1-(4-(N-(3-bromo-4-fluorophenyl)-N'-hydroxyaminoiminomethyl)-isoxazole-3-substituted)-3-(propyl)urea

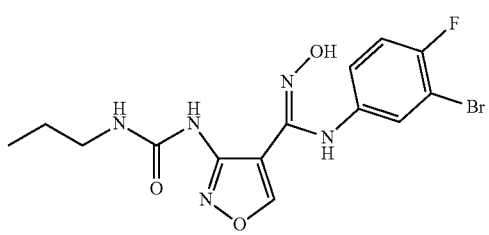 [SMILES: CCCNC(=O)Nc1nocc1/C(=N/O)Nc1ccc(F)c(Br)c1]

The synthesis method was the same as that in Embodiment 1.

$^1$H NMR (400 MHz, DMSO): δ 10.28 (s, 1H), 8.75 (s, 1H), 7.48 (s, 1H), 6.73 (s, 1H), 6.62 (d, J=6.8 Hz, 1H), 6.41 (d, J=6.8 Hz, 1H), 6.12 (s, 1H), 3.16 (d, J=6.6 Hz, 2H), 1.59 (m, 2H), 0.96 (d, J=6.7 Hz, 3H) ppm. $^{13}$C NMR (125 MHz, DMSO): δ 161.3, 152.8, 152.1, 150.1, 146.0, 141.1, 138.5, 134.1, 131.2, 120.3, 120.0, 118.6, 118.0, 115.1, 44.7, 22.7, 10.8 ppm. MS (EI, m/z): 401 (M$^+$+1).

Embodiment 92

(Z)-1-(4-(N-(3-bromo-4-fluorophenyl)-N'-hydroxyaminoiminomethyl)-isoxazole-3-substituted)-3-(isopropyl)urea

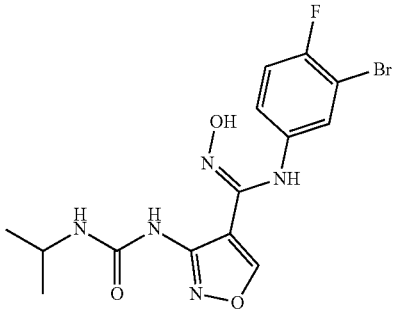 [SMILES: CC(C)NC(=O)Nc1nocc1/C(=N/O)Nc1ccc(F)c(Br)c1]

The synthesis method was the same as that in Embodiment 1.

$^1$H NMR (400 MHz, DMSO): δ 10.28 (s, 1H), 8.75 (s, 1H), 7.48 (s, 1H), 6.73 (s, 1H), 6.62 (d, J=6.8 Hz, 1H), 6.41 (d, J=6.8 Hz, 1H), 6.12 (s, 1H), 3.95 (m, 1H), 1.25 (d, J=6.8 Hz, 6H) ppm. $^{13}$C NMR (125 MHz, DMSO): δ 161.3, 152.8, 152.1, 150.1, 146.0, 141.1, 138.5, 134.1, 131.2, 120.3, 120.0, 118.6, 118.0, 115.1, 43.2, 22.8 ppm. MS (EI, m/z): 401 (M$^+$+1).

Embodiment 93

(Z)-1-(4-(N-(3-bromo-4-fluorophenyl)-N'-hydroxyaminoiminomethyl)-isoxazole-3-substituted)-3-(2-methamidoethyl)urea

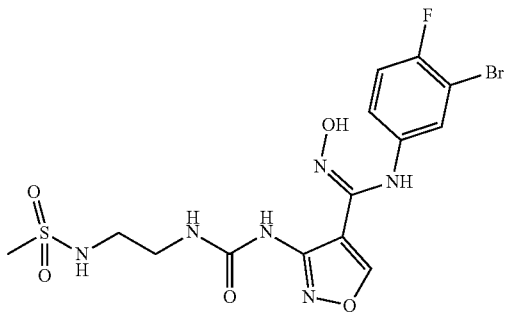 [SMILES: CS(=O)(=O)NCCNC(=O)Nc1nocc1/C(=N/O)Nc1ccc(F)c(Br)c1]

The synthesis method was the same as that in Embodiment 1.

$^1$H NMR (400 MHz, DMSO): δ 10.28 (s, 1H), 8.75 (s, 1H), 7.48 (s, 1H), 6.73 (s, 1H), 6.62 (d, J=6.8 Hz, 1H), 6.41 (d, J=6.8 Hz, 1H), 6.12 (s, 1H), 3.43 (d, J=6.6 Hz, 2H), 2.91 (d, J=6.6 Hz, 6H), 2.81 (s, 3H) ppm. $^{13}$C NMR (125 MHz, DMSO): δ 161.3, 152.8, 152.1, 150.1, 146.0, 141.1, 138.5, 134.1, 131.2, 120.3, 120.0, 118.6, 118.0, 115.1, 41.9, 41.3, 40.2 ppm. MS (EI, m/z): 480 (M$^+$+1).

Embodiment 94

(Z)-1-(4-(N-(3-bromo-4-fluorophenyl)-N'-hydroxyaminoiminomethyl)-isoxazole-3-substituted)-3-(4-aminoindole)urea

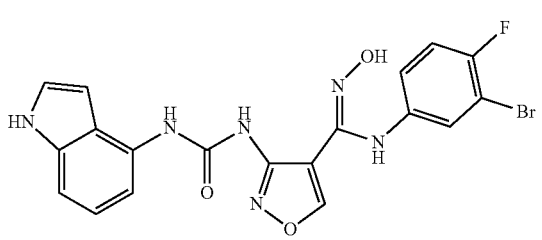 [SMILES: O=C(Nc1nocc1/C(=N/O)Nc1ccc(F)c(Br)c1)Nc1cccc2[nH]ccc12]

The synthesis method was the same as that in Embodiment 1.

$^1$H NMR (400 MHz, DMSO): δ 10.28 (s, 1H), 8.75 (s, 1H), 7.48 (s, 1H), 7.37 (d, J=7.2 Hz, 1H), 7.26 (d, J=7.0 Hz, 1H), 7.15 (d, J=7.2 Hz, 1H), 7.06 (m, 1H), 6.73 (s, 1H), 6.62 (d, J=6.8 Hz, 1H), 6.45 (d, J=7.0 Hz, 1H), 6.41 (d, J=6.8 Hz, 1H), 6.12 (s, 1H) ppm. $^{13}$C NMR (125 MHz, DMSO): δ 161.3, 152.8, 152.1, 150.1, 146.0, 141.1, 138.5, 135.7, 134.1, 131.2, 130.2, 124.3, 120.3, 120.0, 118.6, 118.0, 115.1, 114.7, 112.3, 106.7, 102.3 ppm. MS (EI, m/z): 474 (M$^+$+1).

Embodiment 95

(Z)-1-(4-(N-(3-bromo-4-fluorophenyl)-N'-hydroxyaminoiminomethyl)-isoxazole-3-substituted)-3-(3-aminoindole)urea

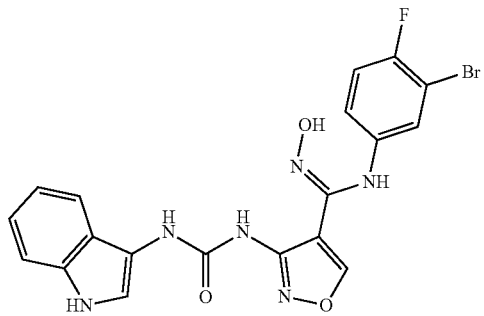 [SMILES: O=C(Nc1nocc1/C(=N/O)Nc1ccc(F)c(Br)c1)Nc1c[nH]c2ccccc12]

The synthesis method was the same as that in Embodiment 1.

$^1$H NMR (400 MHz, DMSO): δ 10.28 (s, 1H), 10.10 (s, 1H), 8.75 (s, 1H), 7.62 (d, J=7.6 Hz, 1H), 7.48 (s, 1H), 7.43 (d, J=7.2 Hz, 1H), 7.33 (d, J=7.0 Hz, 1H), 7.13 (m 1H), 7.05 (m 1H), 6.73 (s, 1H), 6.62 (d, J=6.8 Hz, 1H), 6.40 (d, J=6.8 Hz, 1H), 6.12 (s, 1H), ppm. $^{13}$C NMR (125 MHz, DMSO): δ 161.3, 152.8, 152.1, 150.1, 146.0, 141.1, 138.5, 135.5, 134.1, 131.2, 124.1, 122.2, 120.5, 120.2, 120.0, 119.1, 118.6, 118.0, 115.1, 111.1, 102.3 ppm. MS (EI, m/z): 474 (M$^+$+1).

Embodiment 96

(Z)-1-(4-(N-(3-bromo-4-fluorophenyl)-N'-hydroxyaminoiminomethyl)-isoxazole-3-substituted)-3-(3-aminopyridine)urea

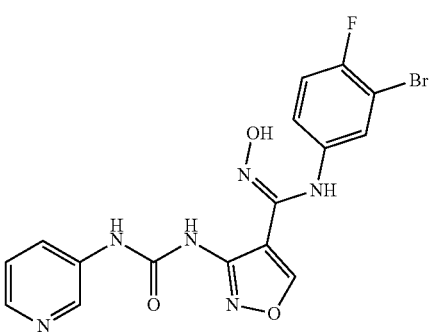 [SMILES: O=C(Nc1cccnc1)Nc1nocc1/C(=N/O)Nc1ccc(F)c(Br)c1]

The synthesis method was the same as that in Embodiment 1.

$^1$H NMR (400 MHz, DMSO): δ 10.28 (s, 1H), 8.75 (s, 1H), 8.53 (s, 1H), 8.23 (d, J=6.6 Hz, 1H), 7.48 (s, 1H), 7.40 (m, 1H), 7.26 (d, J=6.6 Hz, 1H), 6.73 (s, 1H), 6.62 (d, J=6.8 Hz, 1H), 6.41 (d, J=6.8 Hz, 1H), 6.12 (s, 1H) ppm. $^{13}$C NMR (125 MHz, DMSO): δ 161.3, 152.8, 152.1, 150.1, 146.0, 141.1, 138.9, 138.5, 137.6, 134.5, 134.1, 131.2, 124.7, 122.8, 120.3, 120.0, 118.6, 118.0, 115.1, ppm. MS (EI, m/z): 436 (M$^+$+1).

Embodiment 97

(Z)-1-(4-(N-(3-chloro-4-fluorophenyl)-N'-hydroxyaminoiminomethyl)-isoxazole-3-substituted)-3-(4-methoxyphenyl)urea

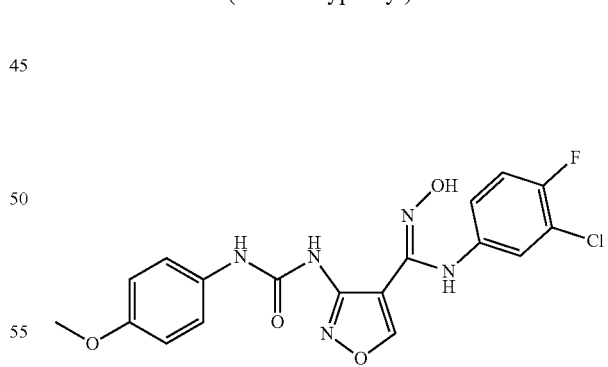

The synthesis method was the same as that in Embodiment 1.

$^1$H NMR (400 MHz, DMSO): δ 10.28 (s, 1H), 8.75 (s, 1H), 7.53 (d, J=6.8 Hz, 1H), 7.48 (s, 1H), 6.79 (d, J=6.8 Hz, 1H), 6.73 (s, 1H), 6.62 (d, J=6.8 Hz, 1H), 6.41 (d, J=6.8 Hz, 1H), 6.12 (s, 1H), ppm. $^{13}$C NMR (125 MHz, DMSO): δ 161.3, 156.3, 152.8, 152.1, 150.1, 146.0, 141.1, 138.5, 134.1, 131.2, 128.2, 122.6, 120.3, 120.0, 118.6, 118.0, 115.1, 114.5, 55.9 ppm. MS (EI, m/z): 420 (M$^+$+1).

Embodiment 98

(Z)-1-(4-(N-(3-chloro-4-fluorophenyl)-N'-hydroxyaminoiminomethyl)-isoxazole-3-substituted)-3-(phenyl)urea

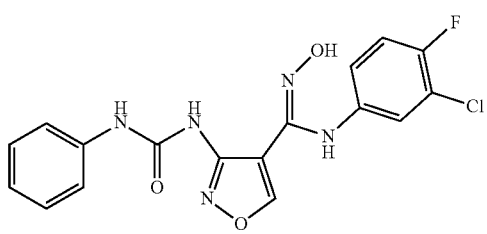 [SMILES: O=C(Nc1ccccc1)Nc1nocc1/C(=N/O)Nc1ccc(F)c(Cl)c1]

The synthesis method was the same as that in Embodiment 1.

$^1$H NMR (400 MHz, DMSO): δ 10.28 (s, 1H), 8.75 (s, 1H), 7.64-7.24 (m, 5H), 7.48 (s, 1H), 6.73 (s, 1H), 6.62 (d, J=6.8 Hz, 1H), 6.41 (d, J=6.8 Hz, 1H), 6.12 (s, 1H), ppm. $^{13}$C NMR (125 MHz, DMSO): δ 161.3, 152.8, 152.1, 150.1, 146.0, 141.1, 138.5, 135.9, 134.1, 131.2, 129.0, 124.4, 121.6, 120.3, 120.0, 118.6, 118.0, 115.1 ppm. MS (EI, m/z): 390 (M$^+$+1).

Embodiment 99

(Z)-1-(4-(N-(3-chloro-4-fluorophenyl)-N'-hydroxyaminoiminomethyl)-isoxazole-3-substituted)-3-(cyclohexyl)urea

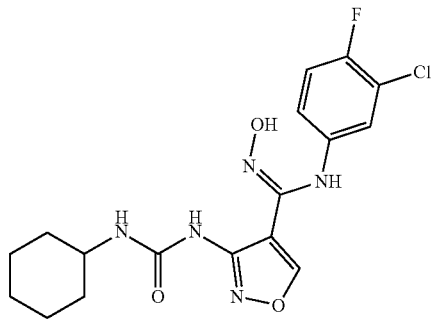 [SMILES: O=C(Nc1nocc1/C(=N/O)Nc1ccc(F)c(Cl)c1)NC1CCCCC1]

The synthesis method was the same as that in Embodiment 1.

$^1$H NMR (400 MHz, DMSO): δ 10.28 (s, 1H), 8.75 (s, 1H), 7.48 (s, 1H), 6.73 (s, 1H), 6.62 (d, J=6.8 Hz, 1H), 6.41 (d, J=6.8 Hz, 1H), 6.12 (s, 1H), 3.57 (m, 1H), 1.79-1.57 (m, 4H), 1.49-1.39 (m, 6H) ppm. $^{13}$C NMR (125 MHz, DMSO): δ 161.3, 152.8, 152.1, 150.1, 146.0, 141.1, 138.5, 134.1, 131.2, 120.3, 120.0, 118.6, 118.0, 115.1, 49.5, 33.3, 28.0, 22.5 ppm. MS (EI, m/z): 396 (M$^+$+1).

Embodiment 100

(Z)-1-(4-(N-(3-bromo-4-fluorophenyl)-N'-hydroxyaminoiminomethyl)-isoxazole-3-substituted)-4-(4-methoxyphenyl)urea

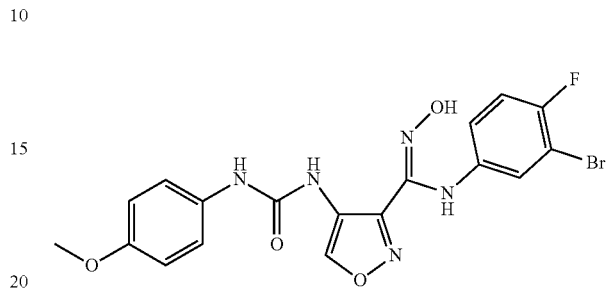

The synthesis method was the same as that in Embodiment 1.

$^1$H NMR (400 MHz, DMSO): δ 10.28 (s, 1H), 8.75 (s, 1H), 7.51 (d, J=7.2 Hz, 2H), 7.48 (s, 1H), 6.77 (d, J=7.2 Hz, 2H), 6.73 (s, 1H), 6.61 (d, J=6.8 Hz, 1H), 6.40 (d, J=6.8 Hz, 1H), 6.13 (s, 1H), 3.73 (s, 3H) ppm. $^{13}$C NMR (125 MHz, DMSO): δ 161.3, 156.3, 152.8, 152.1, 150.1, 146.0, 141.1, 138.5, 134.1, 131.2, 128.2, 122.6, 120.3, 120.0, 118.6, 118.0, 115.1, 114.5, 57.8 ppm. MS (EI, m/z): 465 (M$^+$+1).

Embodiment 101

(Z)-1-(4-(N-(3-bromo-4-fluorophenyl)-N'-hydroxyaminoiminomethyl)-isoxazole-3-substituted)-4-(3-methoxyphenyl)urea

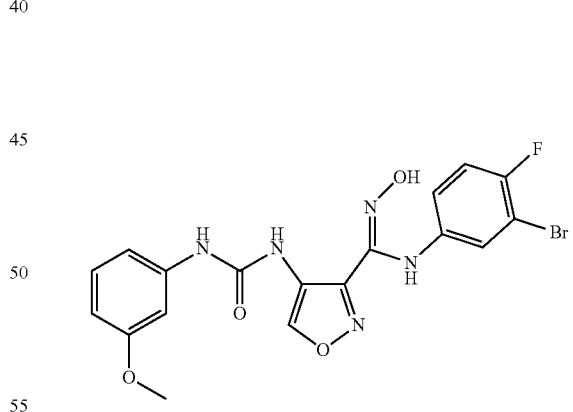

The synthesis method was the same as that in Embodiment 1.

$^1$H NMR (400 MHz, DMSO): δ 10.28 (s, 1H), 8.75 (s, 1H), 7.48 (s, 1H), 7.19 (d, J=6.6 Hz, 1H), 7.16 (s, 1H), 7.13 (m, 1H), 6.72 (s, 1H), 6.61 (d, J=6.8 Hz, 1H), 6.51 (d, J=6.6 Hz, 1H), 6.40 (d, J=6.8 Hz, 1H), 6.13 (s, 1H), 3.71 (s, 3H) ppm. $^{13}$C NMR (125 MHz, DMSO): δ 161.3, 160.9, 152.8, 152.1, 150.1, 146.0, 141.1, 138.5, 136.9, 134.1, 131.2, 130.1, 120.3, 120.0, 118.5, 118.0, 115.1, 113.8, 109.7, 104.7, 55.7 ppm. MS (EI, m/z): 465 (M$^+$+1).

Embodiment 102

(Z)-1-(4-(N-(3-bromo-4-fluorophenyl)-N'-hydroxyaminoiminomethyl)-isoxazole-3-substituted)-4-phenylurea

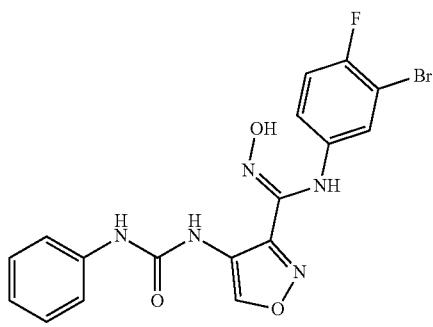 [SMILES: O=C(Nc1ccccc1)Nc1conc1/C(=N/O)Nc1ccc(F)c(Br)c1]

The synthesis method was the same as that in Embodiment 1.

¹H NMR (400 MHz, DMSO): δ 10.27 (s, 1H), 8.74 (s, 1H), 7.48 (s, 1H), 7.43-7.21 (m, 5H), 6.71 (s, 1H), 6.61 (d, J=6.8 Hz, 1H), 6.40 (d, J=6.8 Hz, 1H), 6.10 (s, 1H) ppm. ¹³C NMR (125 MHz, DMSO): δ 161.1, 152.6, 152.1, 150.1, 146.0, 141.1, 138.3, 135.6, 134.1, 131.2, 129.0, 124.3, 121.4, 120.3, 120.0, 118.3, 118.0, 115.1 ppm. MS (EI, m/z): 435 (M⁺+1).

Embodiment 103

(Z)-1-(4-(N-(3-bromo-4-fluorophenyl)-N'-hydroxyaminoiminomethyl)-isoxazole-3-substituted)-4-(cyclohexyl)urea

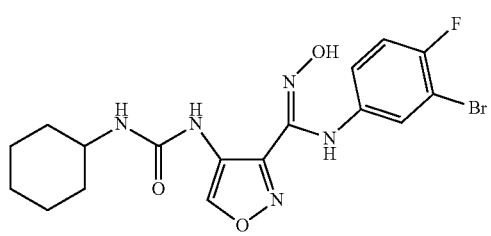 [SMILES: O=C(Nc1conc1/C(=N/O)Nc1ccc(F)c(Br)c1)NC1CCCCC1]

The synthesis method was the same as that in Embodiment 1.

¹H NMR (400 MHz, DMSO): δ 10.27 (s, 1H), 8.74 (s, 1H), 7.47 (s, 1H), 6.73 (s, 1H), 6.62 (d, J=6.8 Hz, 1H), 6.41 (d, J=6.8 Hz, 1H), 6.12 (s, 1H), 3.54 (m, 1H), 1.79-1.55 (m, 4H), 1.49-1.38 (m, 6H) ppm. ¹³C NMR (125 MHz, DMSO): δ 161.3, 152.8, 152.1, 150.1, 146.0, 141.1, 138.5, 134.1, 131.2, 120.3, 120.0, 118.6, 118.0, 115.1, 49.8, 33.6, 28.1, 22.6 ppm. MS (EI, m/z): 441 (M⁺+1).

Embodiment 104

(Z)-1-(4-(N-(3-bromo-4-fluorophenyl)-N'-hydroxyaminoiminomethyl)-isoxazole-3-substituted)-4-(cyclopentyl)urea

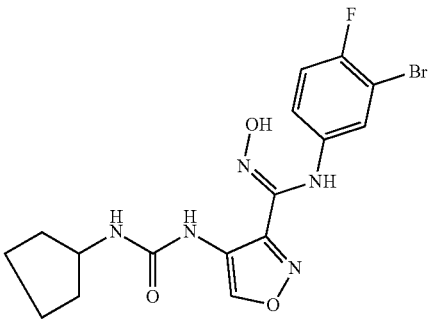 [SMILES: O=C(Nc1conc1/C(=N/O)Nc1ccc(F)c(Br)c1)NC1CCCC1]

The synthesis method was the same as that in Embodiment 1.

¹H NMR (400 MHz, DMSO): δ 10.29 (s, 1H), 8.74 (s, 1H), 7.48 (s, 1H), 6.72 (s, 1H), 6.61 (d, J=6.8 Hz, 1H), 6.41 (d, J=6.8 Hz, 1H), 6.15 (s, 1H), 3.62 (m, 1H), 1.89-1.66 (m, 4H), 1.55-1.46 (m, 4H) ppm. ¹³C NMR (125 MHz, DMSO): δ 161.3, 152.8, 152.1, 150.1, 146.0, 141.2, 138.6, 134.1, 131.1, 120.2, 120.0, 118.5, 118.0, 115.1, 56.3, 34.3, 24.8 ppm. MS (EI, m/z): 427 (M⁺+1).

Embodiment 105

(Z)-1-(4-(N-(3-bromo-4-fluorophenyl)-N'-hydroxyaminoiminomethyl)-isoxazole-3-substituted)-4-(4-hydroxycyclohexyl))urea

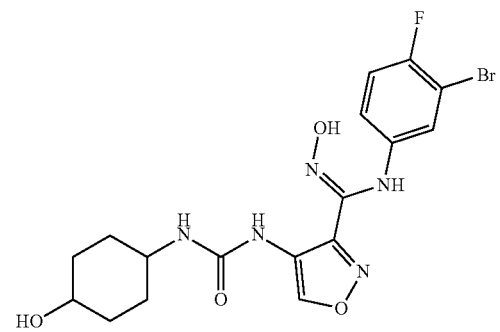 [SMILES: O=C(Nc1conc1/C(=N/O)Nc1ccc(F)c(Br)c1)NC1CCC(O)CC1]

The synthesis method was the same as that in Embodiment 1.

¹H NMR (400 MHz, DMSO): δ 10.30 (s, 1H), 8.77 (s, 1H), 7.49 (s, 1H), 6.75 (s, 1H), 6.62 (d, J=6.8 Hz, 1H), 6.41 (d, J=6.8 Hz, 1H), 6.12 (s, 1H), 3.58 (m, 1H), 3.23 (m, 1H), 1.76-1.49 (m, 8H) ppm. ¹³C NMR (125 MHz, DMSO): δ 161.3, 152.8, 152.2, 150.1, 146.1, 141.2, 138.5, 134.2, 131.3, 120.3, 120.0, 118.6, 118.0, 115.2, 72.8, 49.9, 31.1, 27.2 ppm. MS (EI, m/z): 457 (M⁺+1).

Embodiment 106

(Z)-1-(4-(N-(3-bromo-4-fluorophenyl)-N'-hydroxyaminoiminomethyl)-isoxazole-3-substituted)-4-(piperidine-4-substituted))urea

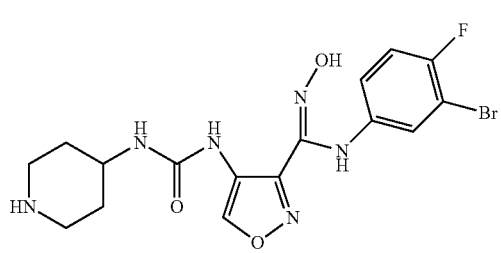 [SMILES: O=C(Nc1conc1/C(=N/O)Nc1ccc(F)c(Br)c1)NC1CCNCC1]

The synthesis method was the same as that in Embodiment 1.

$^1$H NMR (400 MHz, DMSO): δ 10.27 (s, 1H), 8.74 (s, 1H), 7.47 (s, 1H), 6.72 (s, 1H), 6.61 (d, J=6.8 Hz, 1H), 6.40 (d, J=6.8 Hz, 1H), 6.13 (s, 1H), 3.62 (m, 1H), 2.78-2.68 (m, 4H), 1.86-1.61 (m, 4H) ppm. $^{13}$C NMR (125 MHz, DMSO): δ 161.3, 152.8, 152.1, 150.1, 146.0, 141.2, 138.6, 134.0, 131.1, 120.3, 120.1, 118.5, 118.1, 115.1, 46.1, 42.8, 32.1 ppm. MS (EI, m/z): 442 (M$^+$+1).

Embodiment 107

(Z)-1-(4-(N-(3-bromo-4-fluorophenyl)-N'-hydroxyaminoiminomethyl)-isoxazole-3-substituted)-4-cyclopropylurea

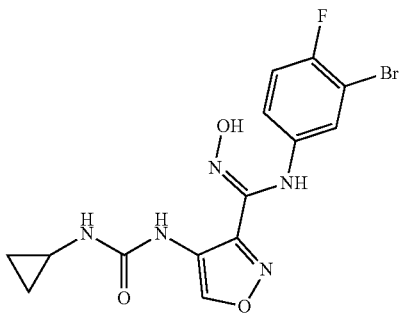

The synthesis method was the same as that in Embodiment 1.

$^1$H NMR (400 MHz, DMSO): δ 10.25 (s, 1H), 8.73 (s, 1H), 7.46 (s, 1H), 6.71 (s, 1H), 6.60 (d, J=6.8 Hz, 1H), 6.39 (d, J=6.8 Hz, 1H), 6.12 (s, 1H), 2.32 (m, 1H), 0.56-0.31 (m, 4H) ppm. $^{13}$C NMR (125 MHz, DMSO): δ 161.2, 152.7, 152.0, 150.1, 146.0, 141.1, 138.5, 134.0, 131.0, 120.2, 120.1, 118.4, 118.1, 115.1, 26.3, 7.2 ppm. MS (EI, m/z): 399 (M$^+$+1).

Embodiment 108

(Z)-1-(4-(N-(3-bromo-4-fluorophenyl)-N'-hydroxyaminoiminomethyl)-isoxazole-3-substituted)-4-(4-aminocyclohexyl))urea

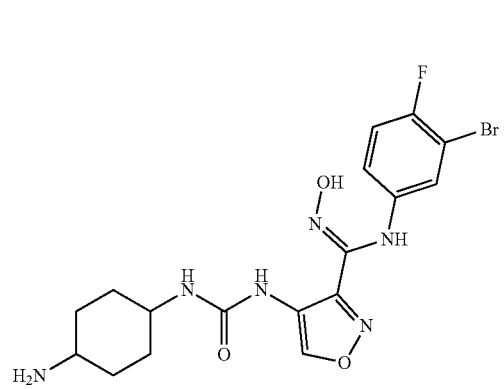

The synthesis method was the same as that in Embodiment 1.

$^1$H NMR (400 MHz, DMSO): δ 10.27 (s, 1H), 8.74 (s, 1H), 7.47 (s, 1H), 6.72 (s, 1H), 6.61 (d, J=6.8 Hz, 1H), 6.40 (d, J=6.8 Hz, 1H), 6.13 (s, 1H), 3.56 (t, J=6.6 Hz, 1H), 2.56 (t, J=6.8 Hz, 1H), 1.80-1.53 (m, 8H) ppm. 13C NMR (125 MHz, DMSO): δ 161.3, 152.8, 152.1, 150.1, 146.0, 141.2, 138.6, 134.0, 131.1, 120.3, 120.1, 118.5, 118.1, 115.1, 50.3, 49.6, 31.0, 28.2 ppm. MS (EI, m/z): 456 (M$^+$+1).

Embodiment 109

(Z)-1-(4-(N-(3-bromo-4-fluorophenyl)-N'-hydroxyaminoiminomethyl)-isoxazole-3-substituted)-)-4-(3-hydroxypropyl))urea

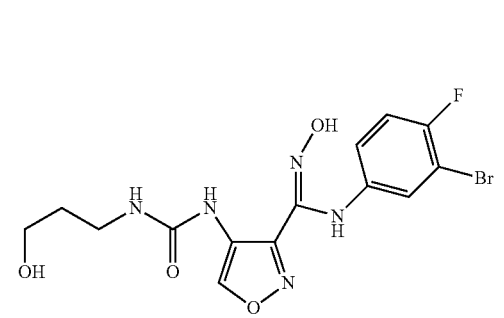

The synthesis method was the same as that in Embodiment 1.

$^1$H NMR (400 MHz, DMSO): δ 10.28 (s, 1H), 8.76 (s, 1H), 7.48 (s, 1H), 6.73 (s, 1H), 6.62 (d, J=6.8 Hz, 1H), 6.41 (d, J=6.8 Hz, 1H), 6.14 (s, 1H), 3.53 (t, J=6.6 Hz, 2H), 3.16 (t, J=6.5 Hz, 2H), 1.73 (m, 2H) ppm. $^{13}$C NMR (125 MHz, DMSO): δ 161.3, 152.8, 152.2, 150.3, 146.1, 141.2, 138.7, 134.1, 131.2, 120.3, 120.2, 118.6, 118.1, 115.1, 59.6, 38.7, 31.7 ppm. MS (EI, m/z): 417 (M$^+$+1).

Embodiment 110

(Z)-1-(4-(N-(3-bromo-4-fluorophenyl)-N'-hydroxyaminoiminomethyl)-isoxazole-3-substituted)-)-4-(2-hydroxyethyl))urea

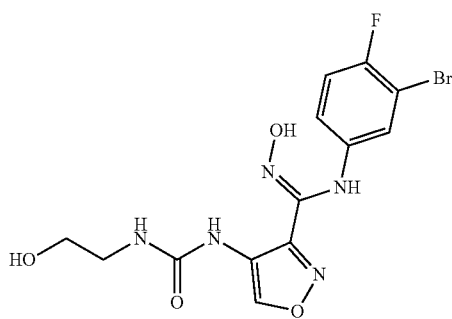

The synthesis method was the same as that in Embodiment 1.

¹H NMR (400 MHz, DMSO): δ 10.29 (s, 1H), 8.76 (s, 1H), 7.48 (s, 1H), 6.73 (s, 1H), 6.63 (d, J=6.8 Hz, 1H), 6.42 (d, J=6.8 Hz, 1H), 6.15 (s, 1H), 3.79 (t, J=6.8 Hz, 2H), 3.36 (t, J=6.8 Hz, 2H) ppm. ¹³C NMR (125 MHz, DMSO): δ 161.4, 152.9, 152.2, 150.4, 146.1, 141.3, 138.7, 134.2, 131.2, 120.4, 120.2, 118.7, 118.1, 115.2, 60.6, 43.7 ppm. MS (EI, m/z): 403 (M$^+$+1).

Embodiment 111

(Z)-1-(4-(N-(3-bromo-4-fluorophenyl)-N'-hydroxyaminoiminomethyl)-isoxazole-3-substituted)-)-4-(2-aminoethyl))urea

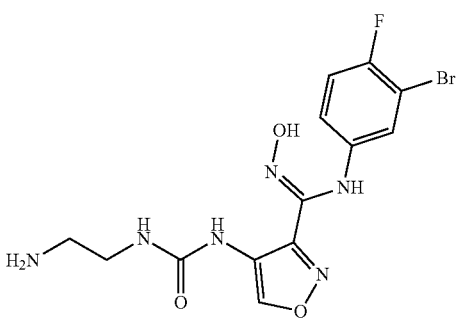 [SMILES: NCCNC(=O)Nc1conc1/C(=N/O)Nc1ccc(F)c(Br)c1]

The synthesis method was the same as that in Embodiment 1.

¹H NMR (400 MHz, DMSO): δ 10.28 (s, 1H), 8.76 (s, 1H), 7.47 (s, 1H), 6.73 (s, 1H), 6.62 (d, J=6.8 Hz, 1H), 6.42 (d, J=6.8 Hz, 1H), 6.14 (s, 1H), 3.43 (t, J=6.6 Hz, 2H), 2.92 (t, J=6.6 Hz, 2H) ppm. ¹³C NMR (125 MHz, DMSO): δ 161.4, 152.9, 152.2, 150.3, 146.1, 141.2, 138.7, 134.2, 131.1, 120.3, 120.2, 118.6, 118.1, 115.1, 45.6, 40.2 ppm. MS (EI, m/z): 402 (M$^+$+1).

Embodiment 112

(Z)-1-(4-(N-(3-chloro-4-fluorophenyl)-N'-hydroxyaminoiminomethyl)-isoxazole-3-substituted)-4-(4-methoxyphenyl)urea

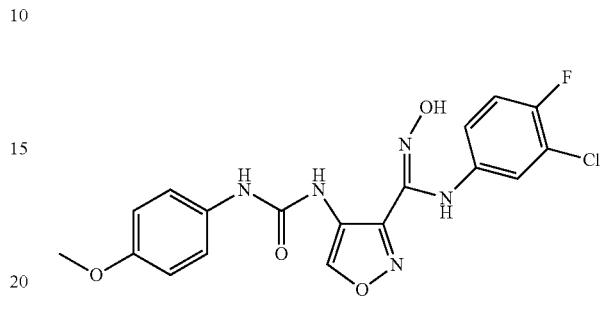

The synthesis method was the same as that in Embodiment 1.

¹H NMR (400 MHz, DMSO): δ 10.27 (s, 1H), 8.72 (s, 1H), 7.50 (d, J=7.2 Hz, 2H), 7.48 (s, 1H), 6.75 (d, J=7.2 Hz, 2H), 6.71 (s, 1H), 6.61 (d, J=6.8 Hz, 1H), 6.39 (d, J=6.8 Hz, 1H), 6.11 (s, 1H), 3.72 (s, 3H) ppm. ¹³C NMR (125 MHz, DMSO): δ 161.1, 156.2, 152.8, 152.0, 150.1, 146.1, 141.0, 138.3, 134.1, 131.1, 128.0, 122.5, 120.2, 120.0, 118.5, 118.0, 115.0, 114.5, 55.9 ppm. MS (EI, m/z): 420 (M$^+$+1).

Embodiment 113

(Z)-1-(4-(N-(3-chloro-4-fluorophenyl)-N'-hydroxyaminoiminomethyl)-isoxazole-3-substituted)-4-phenylurea

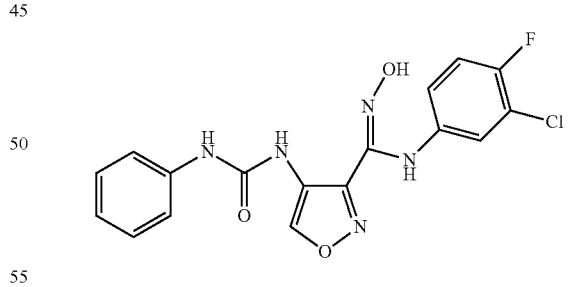

The synthesis method was the same as that in Embodiment 1.

¹H NMR (400 MHz, DMSO): δ 10.27 (s, 1H), 8.74 (s, 1H), 7.48 (s, 1H), 7.43-7.20 (m, 5H), 6.71 (s, 1H), 6.61 (d, J=6.8 Hz, 1H), 6.40 (d, J=6.8 Hz, 1H), 6.10 (s, 1H) ppm. ¹³C NMR (125 MHz, DMSO): δ 161.1, 152.6, 152.1, 150.1, 146.2, 141.1, 138.1, 135.6, 134.1, 131.2, 129.0, 124.3, 121.4, 120.3, 120.0, 118.3, 118.0, 115.0 ppm. MS (EI, m/z): 390 (M$^+$+1).

Embodiment 114

(Z)-1-(4-(N-(3-bromo-4-fluorophenyl)-N'-hydroxyaminoiminomethyl)-isoxazole-3-substituted)-4-(cyclohexyl)urea

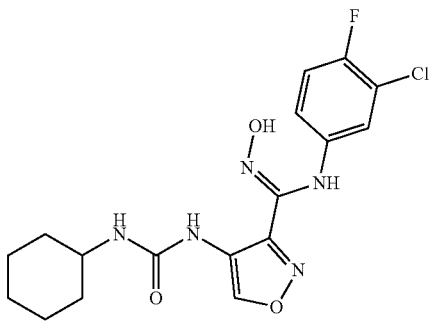 [SMILES: O=C(Nc1conc1/C(=N/O)Nc1ccc(F)c(Cl)c1)NC1CCCCC1]

The synthesis method was the same as that in Embodiment 1.

$^1$H NMR (400 MHz, DMSO): δ 10.26 (s, 1H), 8.74 (s, 1H), 7.46 (s, 1H), 6.72 (s, 1H), 6.61 (d, J=6.8 Hz, 1H), 6.40 (d, J=6.8 Hz, 1H), 6.11 (s, 1H), 3.52 (m, 1H), 1.78-1.53 (m, 4H), 1.497-1.38 (m, 6H) ppm. $^{13}$C NMR (125 MHz, DMSO): δ 161.2, 152.7, 152.1, 150.0, 146.0, 141.1, 138.4, 134.1, 131.1, 120.2, 120.0, 118.5, 118.0, 115.1, 49.5, 33.3, 28.0, 22.3 ppm. MS (EI, m/z): 396 (M$^+$+1).

Embodiment 115

(Z)-1-(4-(N-(3-bromo-4-fluorophenyl)-N'-hydroxyaminoiminomethyl)-1,2,5-oxadiazole-3-substituted)-3-(4-methoxyphenyl)thiourea

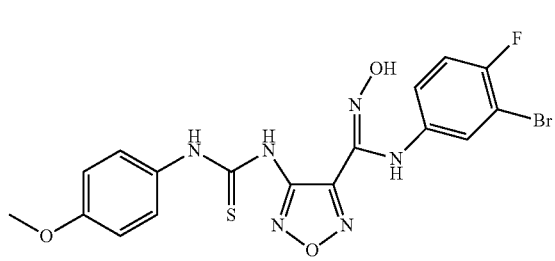 [SMILES: COc1ccc(NC(=S)Nc2nonc2/C(=N/O)Nc2ccc(F)c(Br)c2)cc1]

The synthesis method was the same as that in Embodiment 1.

$^1$H NMR (400 MHz, DMSO): 510.36 (s, 1H), 8.85 (s, 1H), 7.17 (t, J=8.8 Hz, 1H), 7.10 (m, 1H), 6.77 (m, 1H), 6.24 (s, 1H), 3.56 (m, 1H), 1.84-1.80 (m, 2H), 1.63-1.58 (m, 2H), 1.45-1.18 (m, 4H) ppm. $^{13}$C NMR (125 MHz, DMSO): δ 179.6, 158.0, 154.1, 150.2, 148.2, 139.5, 133.5, 130.4, 120.1, 119.5, 119.1, 118.8, 114.7, 113.6, 54.6 ppm. MS (EI, m/z): 482 (M$^+$+1).

Embodiment 116

(Z)-1-(4-(N-(4-bromo-3-fluorophenyl)-N'-hydroxyaminoiminomethyl)-1,2,5-oxadiazole-3-substituted)-3-phenylthiourea

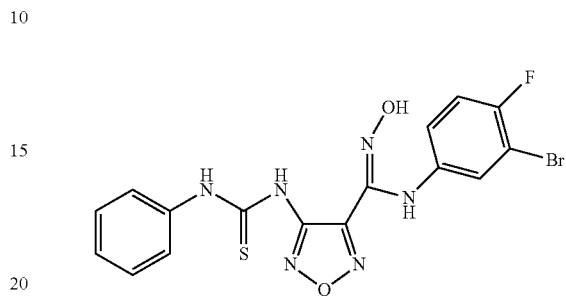

The synthesis method was the same as that in Embodiment 1.

$^1$H NMR (400 MHz, DMSO): δ 10.29 (s, 1H), 8.81 (s, 1H), 7.83 (d, J=8.4 Hz, 1H), 7.19-7.15 (m, 2H), 7.15-7.02 (m, 4H), 6.73-6.52 (m, 3H), 6.21 (s, 1H), 6.07 (s, 1H) ppm. $^{13}$C NMR (125 MHz, DMSO): δ 179.5, 160.1, 154.0, 151.3, 148.1, 140.2, 135.3, 134.8, 121.5, 120.6, 119.0, 118.5, 115.5, 114.3 ppm. MS (EI, m/z): 452 (M$^+$+1).

Embodiment 117

(Z)-1-(4-(N-(3-bromo-4-fluorophenyl)-N'-hydroxyaminoiminomethyl)-1,2,5-oxadiazole-3-substituted)-3-(4-hydroxyphenyl)thiourea

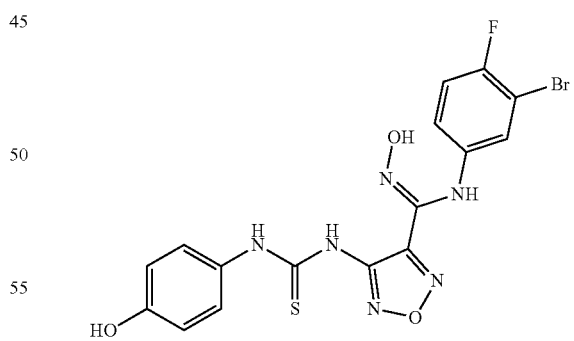

The synthesis method was the same as that in Embodiment 1.

$^1$H NMR (400 MHz, DMSO): δ 11.22 (s, 1H), 8.79 (s, 1H), 7.16 (t, J=8.8 Hz, 1H), 7.08 (m, 1H), 6.76 (m, 1H), 6.23 (s, 1H), 3.53 (m, 1H) ppm. $^{13}$C NMR (125 MHz, DMSO): δ 178.9, 158.0, 153.7, 150.1, 148.3, 139.1, 133.6, 130.6, 120.1, 119.5, 119.0, 118.6, 114.5, 113.3 ppm. MS (EI, m/z): 468 (M$^+$+1).

Embodiment 118

(Z)-1-(4-(N-(3-bromo-4-fluorophenyl)-N'-hydroxyaminoiminomethyl)-1,2,5-oxadiazole-3-substituted)-3-(4-aminophenyl)thiourea

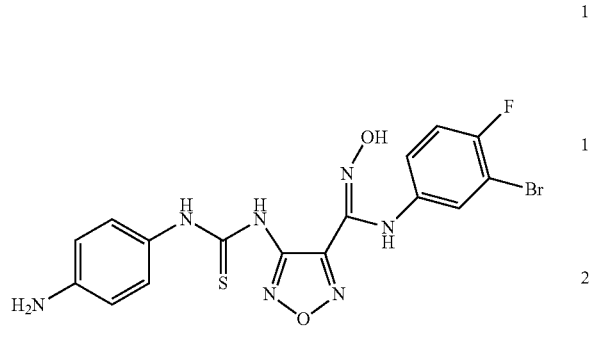

The synthesis method was the same as that in Embodiment 1.

$^1$H NMR (400 MHz, DMSO): δ 11.39 (s, 1H), 8.81 (s, 1H), 7.16 (t, J=8.8 Hz, 1H), 7.05 (m, 1H), 6.74 (m, 1H), 6.23 (s, 1H), ppm. $^{13}$C NMR (125 MHz, DMSO): δ 179.6, 157.9, 153.7, 150.3, 148.2, 139.0, 133.4, 130.5, 120.0, 119.5, 119.0, 118.5, 114.2, 113.3 ppm. MS (EI, m/z): 467 (M$^+$+1).

Embodiment 119

(Z)-1-(4-(N-(3-bromo-4-fluorophenyl)-N'-hydroxyaminoiminomethyl)-1,2,5-oxadiazole-3-substituted)-3-(4-trifluoromethylphenyl)thiourea

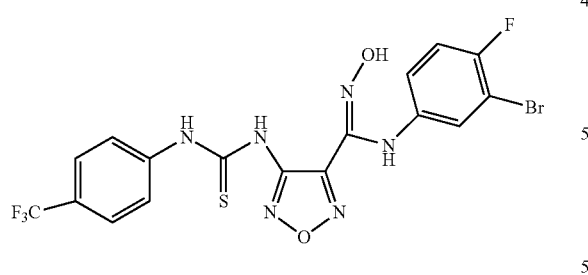

The synthesis method was the same as that in Embodiment 1.

$^1$H NMR (400 MHz, DMSO): δ 11.43 (s, 1H), 8.85 (s, 1H), 7.60 (d, J=6.6 Hz, 2H), 7.25 (d, J=6.6 Hz, 2H), 7.16 (t, J=8.8 Hz, 1H), 7.20-7.06 (m, 1H), 6.73-6.55 (m, 1H), 6.23 (s, 1H), 6.06 (s, 1H) ppm. $^{13}$C NMR (125 MHz, DMSO): δ 178.9, 160.2, 154.3, 151.7, 148.1, 140.8, 135.6, 121.8, 120.9, 119.6, 118.8, 115.9, 115.1 ppm. MS (EI, m/z): 520 (M$^+$+1).

Embodiment 120

(Z)-1-(4-(N-(3-bromo-4-fluorophenyl)-N'-hydroxyaminoiminomethyl)-1,2,5-oxadiazole-3-substituted)-3-(2-fluoro-4-methoxyphenyl)urea

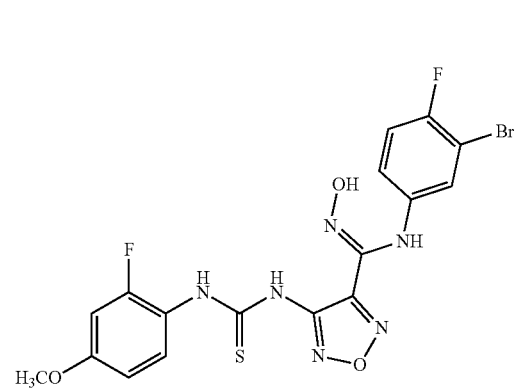 [SMILES: COc1ccc(NC(=S)Nc2nonc2/C(=N/O)Nc2ccc(F)c(Br)c2)c(F)c1]

The synthesis method was the same as that in Embodiment 1.

$^1$H NMR (400 MHz, DMSO): δ 11.47 (s, 1H), 8.89 (s, 1H), 7.59 (s, 1H), 7.29-7.23 (m, 2H), 7.21 (d, J=8.8 Hz, 1H), 7.13 (m, 1H), 6.79-6.53 (m, 1H), 6.22 (s, 1H), 6.13 (s, 1H), 3.79 (s, 3H) ppm. $^{13}$C NMR (125 MHz, DMSO): δ 179.9, 154.5, 151.3, 147.3, 140.5, 136.3, 134.8, 139.3, 120.9, 119.8, 118.7, 114.5, 55.6 ppm. MS (EI, m/z): 500 (M$^+$+1).

Embodiment 121

(Z)-1-(4-(N-(3-bromo-4-fluorophenyl)-N'-hydroxyaminoiminomethyl)-1,2,5-oxadiazole-3-substituted-)-3-(cyclohexyl)thiourea

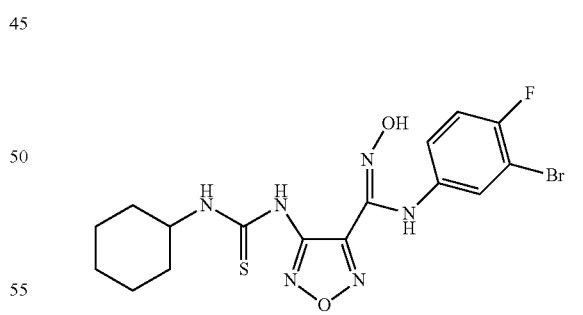

The synthesis method was the same as that in Embodiment 1.

$^1$H NMR (400 MHz, DMSO): δ 11.46 (s, 1H), 8.85 (s, 1H), 7.19 (t, J=8.8 Hz, 1H), 7.12 (m, 1H), 6.81-6.77 (m, 1H), 6.27 (s, 1H), 3.59-3.53 (m, 1H), 1.85-1.81 (m, 2H), 1.63-1.59 (m, 2H), 1.46-1.21 (m, 6H) ppm. $^{13}$C NMR (125 MHz, DMSO): δ 179.8, 159.3, 154.5, 149.2, 145.8, 135.1, 134.6, 112.7, 107.6, 100.4, 52.3, 31.9, 26.3, 24.9 ppm. MS (EI, m/z): 458 (M$^+$+1).

Embodiment 122

(Z)-1-(4-(N-(3-bromo-4-fluorophenyl)-N'-hydroxyaminoiminomethyl)-1,2,5-oxadiazole-3-substituted)-3-(cyclopentyl)thiourea

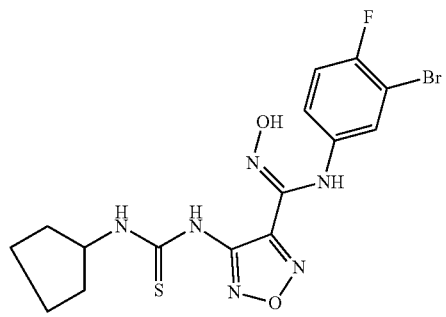 [SMILES: O/N=C(\Nc1ccc(F)c(Br)c1)c1nonc1NC(=S)NC1CCCC1]

The synthesis method was the same as that in Embodiment 1.

$^1$H NMR (400 MHz, DMSO): δ 11.53 (s, 1H), 8.83 (s, 1H), 7.18 (t, J=8.8 Hz, 1H), 7.13-7.02 (m, 1H), 6.77-6.61 (m, 1H), 6.15 (s, 1H), 3.62-3.58 (m, 1H), 1.85-1.62 (m, 4H), 1.56-1.48 (m, 4H) ppm. $^{13}$C NMR (125 MHz, DMSO): δ 179.8, 158.3, 153.9, 148.2, 145.9, 135.2, 134.5, 112.3, 107.5, 101.1, 58.2, 32.5, 24.7 ppm. MS (EI, m/z): 444 (M$^+$+1).

Embodiment 123

(Z)-1-(4-(N-(3-bromo-4-fluorophenyl)-N'-hydroxyaminoiminomethyl)-1,2,5-oxadiazole-3-substituted)-3-(4-hydroxycyclohexyl)thiourea

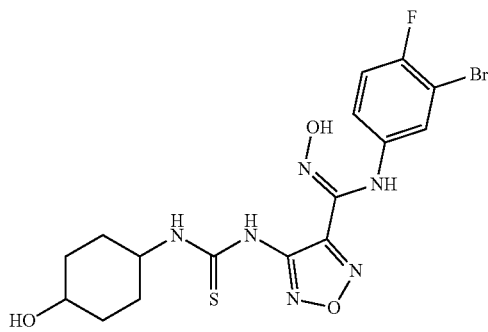 [SMILES: O/N=C(\Nc1ccc(F)c(Br)c1)c1nonc1NC(=S)NC1CCC(O)CC1]

The synthesis method was the same as that in Embodiment 1.

$^1$H NMR (400 MHz, DMSO): δ 11.48 (s, 1H), 8.84 (s, 1H), 7.13 (t, J=8.8 Hz, 1H), 7.12-7.06 (m, 1H), 6.83-6.72 (m, 1H), 6.23 (s, 1H), 3.57-3.53 (m, 1H), 3.37 (m, 1H), 1.85-1.82 (m, 2H), 1.66-1.56 (m, 2H), 1.47-1.21 (m, 5H) ppm. $^{13}$C NMR (125 MHz, DMSO): δ 179.9, 159.2, 153.8, 149.3, 145.4, 135.3, 133.9, 112.9, 107.3, 100.8, 53.6, 51.9, 33.9, 32.7, 31.6 ppm. MS (EI, m/z): 474 (M$^+$+1).

Embodiment 124

(Z)-1-(4-(N-(3-bromo-4-fluorophenyl)-N'-hydroxyaminoiminomethyl)-1,2,5-oxadiazole-3-substituted)-3-(piperidine-4-substituted)thiourea The synthesis method was the same as that in Embodiment 1.

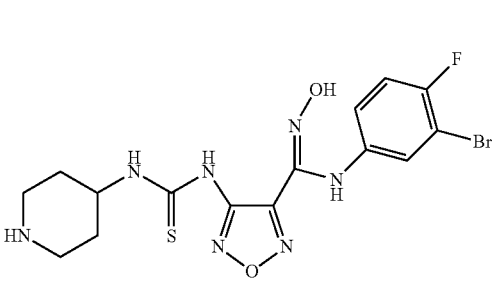 [SMILES: O/N=C(\Nc1ccc(F)c(Br)c1)c1nonc1NC(=S)NC1CCNCC1]

$^1$H NMR (400 MHz, DMSO): δ 11.51 (s, 1H), 8.82 (s, 1H), 7.16 (t, J=8.8 Hz, 1H), 7.11 (m, 1H), 6.84 (m, 1H), 6.28 (s, 1H), 3.55 (m, 1H), 2.79-2.67 (m, 4H), 1.67-1.55 (m, 4H) ppm. $^{13}$C NMR (125 MHz, DMSO): 5179.6, 159.3, 154.4, 149.3, 145.6, 135.3, 134.7, 112.7, 107.3, 100.6, 51.6, 42.5, 32.0 ppm. MS (EI, m/z): 459 (M$^+$+1).

Embodiment 125

(Z)-1-(4-(N-(3-bromo-4-fluorophenyl)-N'-hydroxyaminoiminomethyl)-1,2,5-oxadiazole-3-substituted)-3-(cyclopropyl)thiourea

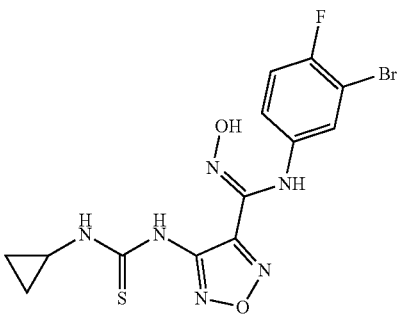 [SMILES: O/N=C(\Nc1ccc(F)c(Br)c1)c1nonc1NC(=S)NC1CC1]

The synthesis method was the same as that in Embodiment 1.

$^1$H NMR (400 MHz, DMSO): δ 11.50 (s, 1H), 8.79 (s, 1H), 7.14 (t, J=8.8 Hz, 1H), 7.13-7.01 (m, 1H), 6.74-6.60 (m, 1H), 6.12 (s, 1H), 3.32 (m, 1H), 1.23-1.03 (m, 4H) ppm. $^{13}$C NMR (125 MHz, DMSO): δ 179.6, 158.0, 153.5, 148.0, 145.4, 135.1, 134.1, 112.3, 107.1, 101.0, 38.2, 11.0 ppm. MS (EI, m/z): 416 (M$^+$+1).

Embodiment 126

(Z)-1-(4-(N-(3-bromo-4-fluorophenyl)-N'-hydroxyaminoiminomethyl)-1,2,5-oxadiazole-3-substituted)-3-(4-aminocyclohexyl)thiourea

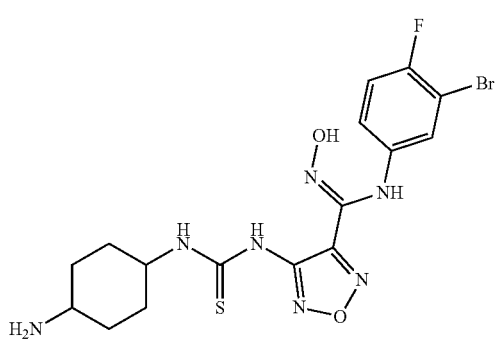 [SMILES: NC1CCC(NC(=S)Nc2nonc2/C(=N/O)Nc2ccc(F)c(Br)c2)CC1]

The synthesis method was the same as that in Embodiment 1.

$^1$H NMR (400 MHz, DMSO): δ 11.45 (s, 1H), 8.81 (s, 1H), 7.10 (t, J=8.8 Hz, 1H), 7.13-7.07 (m, 1H), 6.81-6.70 (m, 1H), 6.21 (s, 1H), 3.54-3.50 (m, 1H), 2.85 (m, 1H), 1.82-1.81 (m, 2H), 1.63-1.55 (m, 2H), 1.46-1.21 (m, 5H) ppm. $^{13}$C NMR (125 MHz, DMSO): δ 179.5, 159.0, 153.4, 149.1, 145.1, 135.0, 133.6, 112.5, 107.0, 100.3, 53.0, 33.6, 32.1, 31.2 ppm. MS (EI, m/z): 473 (M$^+$+1).

Embodiment 127

(Z)-1-(4-(N-(3-bromo-4-fluorophenyl)-N'-hydroxyaminoiminomethyl)-1,2,5-oxadiazole-3-substituted)-3-(3-hydroxypropyl)thiourea

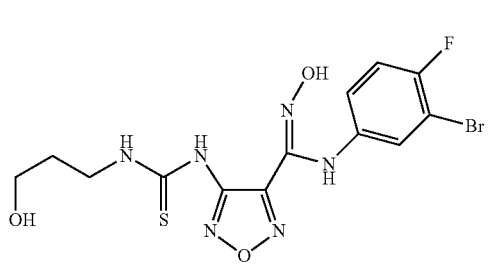 [SMILES: OCCCNC(=S)Nc1nonc1/C(=N/O)Nc1ccc(F)c(Br)c1]

The synthesis method was the same as that in Embodiment 1.

$^1$H NMR (400 MHz, DMSO): δ 11.50 (s, 1H), 8.82 (s, 1H), 7.16 (t, J=8.8 Hz, 1H), 7.10 (m, 1H), 6.82 (m, 1H), 6.26 (s, 1H), 3.55 (t, J=6.8 Hz, 2H), 3.14 (t, J=6.6 Hz, 2H), 1.78 (m, 2H) ppm. $^{13}$C NMR (125 MHz, DMSO): 5179.7, 159.2, 154.2, 149.2, 145.3, 135.1, 134.7, 112.6, 107.2, 100.5, 59.8, 39.3, 31.5 ppm. MS (EI, m/z): 434 (M$^+$+1).

Embodiment 128

(Z)-1-(4-(N-(3-bromo-4-fluorophenyl)-N'-hydroxyaminoiminomethyl)-1,2,5-oxadiazole-3-substituted)-3-(2-hydroxyethyl)thiourea

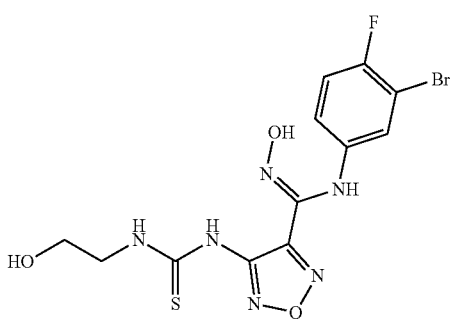 [SMILES: OCCNC(=S)Nc1nonc1/C(=N/O)Nc1ccc(F)c(Br)c1]

The synthesis method was the same as that in Embodiment 1.

$^1$H NMR (400 MHz, DMSO): δ 11.52 (s, 1H), 8.84 (s, 1H), 7.19 (t, J=8.8 Hz, 1H), 7.13 (m, 1H), 6.83 (m, 1H), 6.28 (s, 1H), 3.57 (t, J=6.8 Hz, 2H), 3.17 (t, J=6.8 Hz, 2H) ppm. $^{13}$C NMR (125 MHz, DMSO): δ 179.9, 159.3, 154.5, 149.5, 145.6, 135.3, 134.8, 112.8, 107.4, 100.6, 59.8, 39.6 ppm. MS (EI, m/z): 420 (M$^+$+1).

Embodiment 129

(Z)-1-(4-(N-(3-bromo-4-fluorophenyl)-N'-hydroxyaminoiminomethyl)-1,2,5-oxadiazole-3-substituted)-3-(2-aminoethyl)thiourea

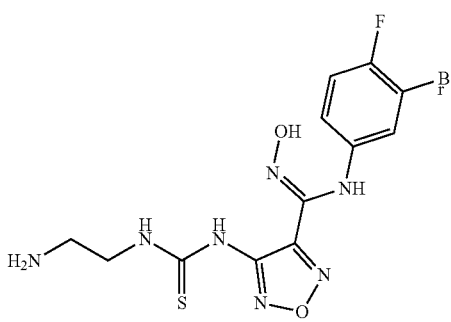 [SMILES: NCCNC(=S)Nc1nonc1/C(=N/O)Nc1ccc(F)c(Br)c1]

The synthesis method was the same as that in Embodiment 1.

$^1$H NMR (400 MHz, DMSO): δ 11.46 (s, 1H), 8.80 (s, 1H), 7.12 (t, J=8.8 Hz, 1H), 7.03 (m, 1H), 6.80 (m, 1H), 6.22 (s, 1H), 3.34 (t, J=6.8 Hz, 2H), 2.85 (t, J=6.8 Hz, 2H) ppm. $^{13}$C NMR (125 MHz, DMSO): δ 179.6, 159.1, 154.0, 149.0, 144.9, 135.0, 134.2, 112.3, 106.9, 100.1, 43.6, 39.5, ppm. MS (EI, m/z): 419 (M$^+$+1).

Embodiment 130

(Z)-1-(4-(N-(3-chloro-4-fluorophenyl)-N'-hydroxyaminoiminomethyl)-isoxazole-3-substituted)-4-(4-methoxyphenyl)thiourea

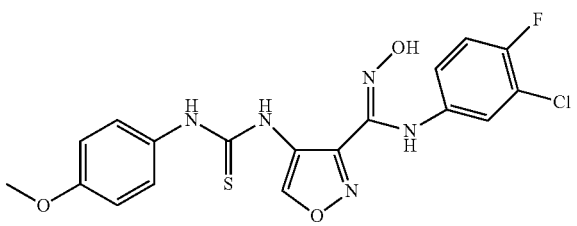 [SMILES: COc1ccc(NC(=S)Nc2conc2/C(=N/O)Nc2ccc(F)c(Cl)c2)cc1]

The synthesis method was the same as that in Embodiment 1.

$^1$H NMR (400 MHz, DMSO): δ 10.28 (s, 1H), 8.75 (s, 1H), 7.51 (d, J=7.2 Hz, 2H), 7.48 (s, 1H), 6.77 (d, J=7.2 Hz, 2H), 6.73 (s, 1H), 6.61 (d, J=6.8 Hz, 1H), 6.40 (d, J=6.8 Hz, 1H), 6.13 (s, 1H), 3.73 (s, 3H) ppm. $^{13}$C NMR (125 MHz, DMSO): δ 179.3, 156.3, 152.7, 152.1, 150.0, 146.0, 140.8, 138.5, 134.0, 131.2, 128.1, 122.5, 120.3, 118.5, 118.0, 115.0, 114.3, 57.6 ppm. MS (EI, m/z): 436 (M$^+$+1).

Embodiment 131

(Z)-1-(4-(N-(3-chloro-4-fluorophenyl)-N'-hydroxyaminoiminomethyl)-isoxazole-3-substituted)-4-(phenyl)thiourea

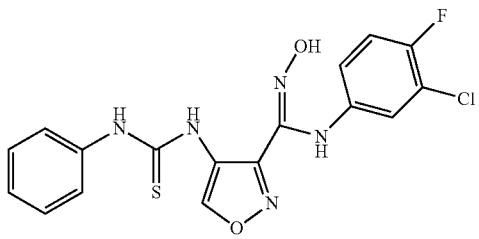

The synthesis method was the same as that in Embodiment 1.

$^1$H NMR (400 MHz, DMSO): δ 10.26 (s, 1H), 8.73 (s, 1H), 7.46 (s, 1H), 7.43-7.21 (m, 5H), 6.72 (s, 1H), 6.61 (d, J=6.8 Hz, 1H), 6.38 (d, J=6.8 Hz, 1H), 6.10 (s, 1H) ppm. $^{13}$C NMR (125 MHz, DMSO): δ 179.6, 152.5, 150.0, 146.0, 141.0, 138.2, 135.4, 134.1, 131.1, 129.0, 124.2, 121.3, 120.3, 119.8, 118.2, 115.0 ppm. MS (EI, m/z): 406 (M$^+$+1).

Embodiment 132

(Z)-1-(4-(N-(3-chloro-4-fluorophenyl)-N'-hydroxyaminoiminomethyl)-isoxazole-3-substituted)-4-(cyclohexyl)thiourea

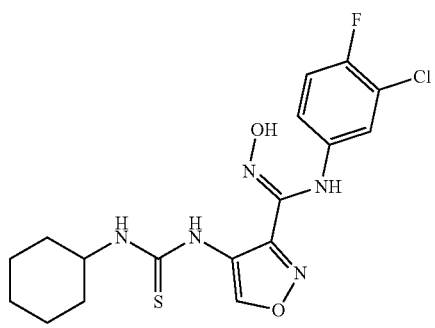 [SMILES: O/N=C(\Nc1ccc(F)c(Cl)c1)c1nocc1NC(=S)NC1CCCCC1]

The synthesis method was the same as that in Embodiment 1.

$^1$H NMR (400 MHz, DMSO): δ 10.27 (s, 1H), 8.74 (s, 1H), 7.47 (s, 1H), 6.73 (s, 1H), 6.62 (d, J=6.8 Hz, 1H), 6.41 (d, J=6.8 Hz, 1H), 6.12 (s, 1H), 3.54 (m, 1H), 1.79-1.55 (m, 4H), 1.49-1.38 (m, 6H) ppm. $^{13}$C NMR (125 MHz, DMSO): δ 179.6, 152.7, 152.1, 150.1, 145.8, 141.1, 138.3, 134.1, 131.1, 120.2, 118.5, 118.0, 115.0, 49.7, 33.5, 28.1, 22.5 ppm. MS (EI, m/z): 412 (M$^+$+1).

Embodiment 133

(Z)-1-(4-(N-(3-bromo-4-fluorophenyl)-N'-hydroxyaminoiminomethyl)-isoxazole-3-substituted)-3-(4-methoxyphenyl)thiourea

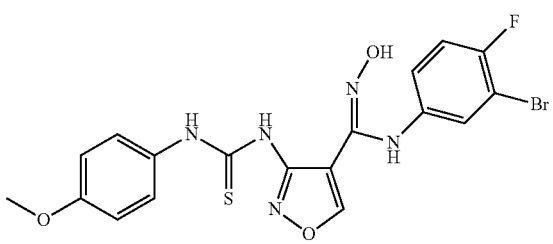 [SMILES: COc1ccc(NC(=S)Nc2nocc2/C(=N/O)Nc2ccc(F)c(Br)c2)cc1]

The synthesis method was the same as that in Embodiment 1.

$^1$H NMR (400 MHz, DMSO): δ 10.27 (s, 1H), 8.74 (s, 1H), 7.50 (d, J=7.2 Hz, 2H), 7.48 (s, 1H), 6.76 (d, J=7.2 Hz, 2H), 6.73 (s, 1H), 6.61 (d, J=6.8 Hz, 1H), 6.40 (d, J=6.8 Hz, 1H), 6.12 (s, 1H), 3.73 (s, 3H) ppm. $^{13}$C NMR (125 MHz, DMSO): δ 179.4, 156.3, 152.7, 152.1, 150.1, 146.0, 140.8, 138.5, 134.0, 131.3, 128.1, 122.5, 120.2, 118.5, 118.1, 115.0, 114.4, 57.6 ppm. MS (EI, m/z): 481 (M$^+$+1).

Embodiment 134

(Z)-1-(4-(N-(3-bromo-4-fluorophenyl)-N'-hydroxyaminoiminomethyl)-isoxazole-3-substituted)-3-(phenyl)thiourea

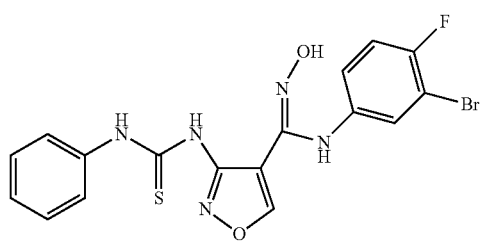 [SMILES: O/N=C(\Nc1ccc(F)c(Br)c1)c1conc1NC(=S)Nc1ccccc1]

The synthesis method was the same as that in Embodiment 1.

$^1$H NMR (400 MHz, DMSO): δ 10.27 (s, 1H), 8.73 (s, 1H), 7.47 (s, 1H), 7.43-7.21 (m, 5H), 6.73 (s, 1H), 6.61 (d, J=6.8 Hz, 1H), 6.39 (d, J=6.8 Hz, 1H), 6.10 (s, 1H) ppm. $^{13}$C NMR (125 MHz, DMSO): δ 179.6, 152.6, 150.0, 146.1, 141.0, 138.3, 135.4, 134.2, 131.1, 129.0, 124.2, 121.5, 120.3, 119.9, 118.2, 115.1 ppm. MS (EI, m/z): 451 (M$^+$+1).

Embodiment 135

(Z)-1-(4-(N-(3-bromo-4-fluorophenyl)-N'-hydroxyaminoiminomethyl)-isoxazole-3-substituted)-3-(cyclohexyl)thiourea

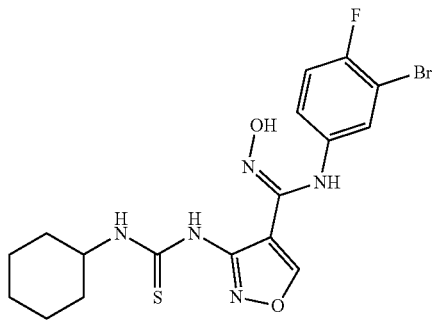 [SMILES: O/N=C(\Nc1ccc(F)c(Br)c1)c1conc1NC(=S)NC1CCCCC1]

The synthesis method was the same as that in Embodiment 1.

¹H NMR (400 MHz, DMSO): δ 10.28 (s, 1H), 8.75 (s, 1H), 7.47 (s, 1H), 6.74 (s, 1H), 6.63 (d, J=6.8 Hz, 1H), 6.42 (d, J=6.8 Hz, 1H), 6.13 (s, 1H), 3.55 (m, 1H), 1.79-1.55 (m, 4H), 1.49-1.38 (m, 6H) ppm. ¹³C NMR (125 MHz, DMSO): δ 179.7, 152.7, 152.2, 150.1, 145.9, 141.1, 138.4, 134.1, 131.2, 120.2, 118.6, 118.0, 115.1, 49.8, 33.5, 28.2, 22.6 ppm. MS (EI, m/z): 457 (M⁺+1).

Embodiment 136

(Z)-1-(4-(N-(3-bromo-4-fluorophenyl)-N'-hydroxyaminoiminomethyl)-furan-3-substituted)-3-(4-methoxyphenyl)thiourea

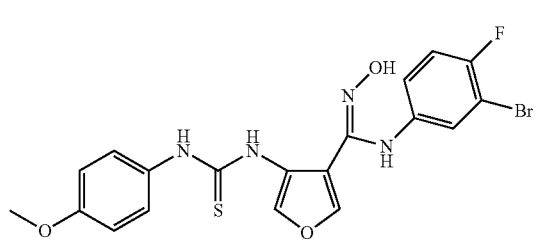 [SMILES: COc1ccc(NC(=S)Nc2cocc2/C(=N/O)Nc2ccc(F)c(Br)c2)cc1]

The synthesis method was the same as that in Embodiment 1.

¹H NMR (400 MHz, DMSO): δ 10.31 (s, 1H), 8.79 (s, 1H), 7.53 (d, J=8.6 Hz, 2H), 7.43 (s, 1H), 7.41 (s, 1H), 6.84 (d, J=8.6 Hz, 2H), 6.72 (s, 1H), 6.62 (d, J=8.0 Hz, 1H), 6.42 (d, J=8.0 Hz, 1H), 6.13 (s, 1H), 3.72 (s, 3H) ppm. ¹³C NMR (125 MHz, DMSO): δ 178.9, 152.0, 149.8, 146.1, 142.6, 141.7, 141.1, 139.0, 134.2, 131.7, 120.5, 120.1, 118.6, 115.6, 55.7 ppm. MS (EI, m/z): 480 (M⁺+1).

Embodiment 137

(Z)-1-(4-(N-(3-bromo-4-fluorophenyl)-N'-hydroxyaminoiminomethyl)-furan-3-substituted)-3-phenylthiourea

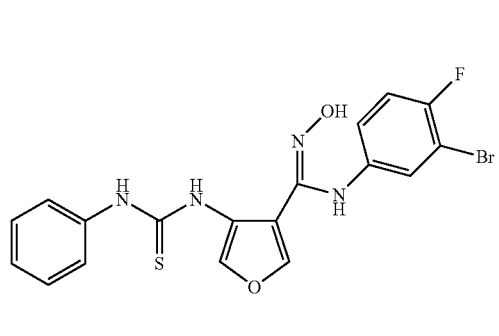 [SMILES: O/N=C(\Nc1ccc(F)c(Br)c1)c1cocc1NC(=S)Nc1ccccc1]

The synthesis method was the same as that in Embodiment 1.

¹H NMR (400 MHz, DMSO): δ 10.30 (s, 1H), 8.78 (s, 1H), 7.60-7.28 (m, 5H), 7.42 (s, 1H), 7.39 (s, 1H), 6.78 (s, 1H), 6.69 (d, J=6.8 Hz, 1H), 6.49 (d, J=6.8 Hz, 1H), 6.15 (s, 1H) ppm. ¹³C NMR (125 MHz, DMSO): δ 178.7, 152.1, 149.8, 146.1, 142.5, 141.3, 141.0, 138.8, 134.0, 131.3, 120.2, 120.0, 118.5, 118.1, 115.0 ppm. MS (EI, m/z): 450 (M⁺+1).

Embodiment 138

(Z)-1-(4-(N-(3-bromo-4-fluorophenyl)-N'-hydroxyaminoiminomethyl)-furan-3-substituted)-3-cyclohexylthiourea

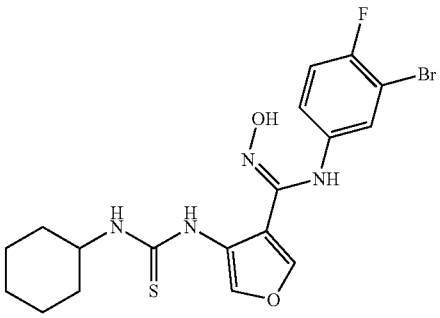 [SMILES: O/N=C(\Nc1ccc(F)c(Br)c1)c1cocc1NC(=S)NC1CCCCC1]

The synthesis method was the same as that in Embodiment 1.

¹H NMR (400 MHz, DMSO): δ 10.27 (s, 1H), 8.73 (s, 1H), 7.40 (s, 1H), 7.39 (s, 1H), 6.76 (s, 1H), 6.65 (d, J=6.8 Hz, 1H), 6.43 (d, J=6.8 Hz, 1H), 6.11 (s, 1H), 1.83-1.78 (m, 2H), 1.63-1.56 (m, 2H), 1.43-1.19 (m, 6H) ppm. ¹³C NMR (125 MHz, DMSO): δ 178.3, 152.0, 148.9, 146.1, 142.5, 141.5, 141.0, 138.7, 134.0, 131.3, 120.2, 118.5, 118.1, 115.1, 49.3, 33.5, 28.1, 22.3 ppm. MS (EI, m/z): 456 (M⁺+1).

Embodiment 139

(Z)-1-(4-(N-(3-bromo-4-fluorophenyl)-N'-hydroxyaminoiminomethyl)-1,2,5-oxadiazole-3-substituted)-3-(4-methoxyphenyl)guanidine

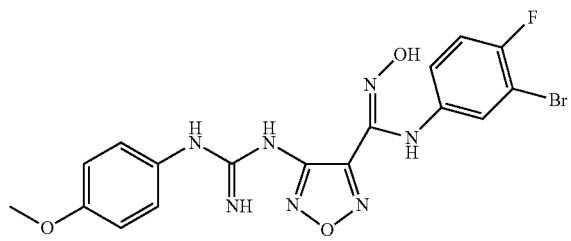 [SMILES: COc1ccc(NC(=N)Nc2nonc2/C(=N/O)Nc2ccc(F)c(Br)c2)cc1]

The synthesis method was the same as that in Embodiment 1.

$^1$H NMR (400 MHz, DMSO): δ 11.41 (s, 1H), 9.05 (s, 1H), 8.83 (s, 1H), 7.17 (t, J=8.8 Hz, 1H), 7.09 (m, 1H), 6.77 (m, 1H), 6.25 (s, 1H), 3.56 (m, 1H), 1.85-1.81 (m, 2H), 1.63-1.59 (m, 2H), 1.46-1.19 (m, 4H) ppm. $^{13}$C NMR (125 MHz, DMSO): δ 163.1, 157.1, 153.1, 150.2, 148.2, 139.2, 133.5, 130.6, 120.0, 119.3, 119.0, 118.8, 114.8, 113.5, 54.5 ppm. MS (EI, m/z): 465 (M$^+$+1).

Embodiment 140

(Z)-1-(4-(N-(3-bromo-4-fluorophenyl)-N'-hydroxyaminoiminomethyl)-1,2,5-oxadiazole-3-substituted)-3-phenylguanidine

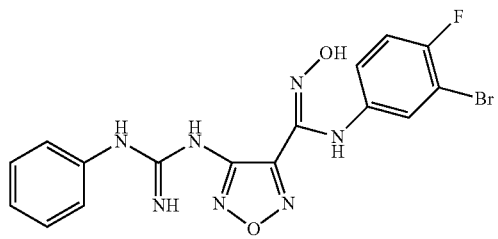 [SMILES: N=C(Nc1ccccc1)Nc1nonc1/C(=N/O)Nc1ccc(F)c(Br)c1]

The synthesis method was the same as that in Embodiment 1.

$^1$H NMR (400 MHz, DMSO): δ 11.40 (s, 1H), 9.03 (s, 1H), 8.78 (s, 1H), 7.82 (d, J=8.4 Hz, 1H), 7.16-7.12 (m, 2H), 7.13-7.01 (m, 4H), 6.73-6.52 (m, 3H), 6.21 (s, 1H), 6.06 (s, 1H) ppm. $^{13}$C NMR (125 MHz, DMSO): δ 163.0, 159.2, 154.0, 151.3, 148.1, 140.2, 135.1, 134.7, 121.6, 120.5, 119.0, 118.5, 115.6, 114.3 ppm. MS (EI, m/z): 435 (M$^+$+1).

Embodiment 141

(Z)-1-(4-(N-(3-bromo-4-fluorophenyl)-N'-hydroxyaminoiminomethyl)-1,2,5-oxadiazole-3-substituted)-3-(4-hydroxyphenyl)guanidine

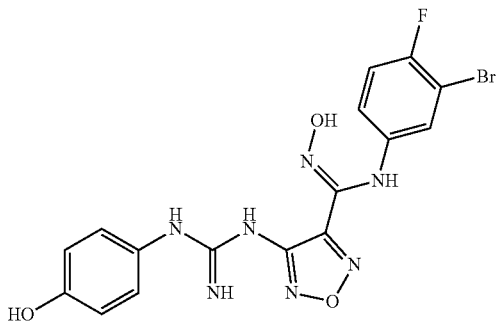 [SMILES: N=C(Nc1ccc(O)cc1)Nc1nonc1/C(=N/O)Nc1ccc(F)c(Br)c1]

The synthesis method was the same as that in Embodiment 1.

$^1$H NMR (400 MHz, DMSO): δ 11.38 (s, 1H), 9.05 (s, 1H), 8.78 (s, 1H), 7.13 (t, J=8.8 Hz, 1H), 7.05 (m, 1H), 6.75 (m, 1H), 6.22 (s, 1H), 3.52 (m, 1H) ppm. $^{13}$C NMR (125 MHz, DMSO): δ 162.8, 157.6, 153.7, 150.0, 148.1, 139.1, 133.2, 130.5, 120.1, 119.2, 119.0, 118.3, 114.2, 113.1 ppm. MS (EI, m/z): 406 (M$^+$+1).

Embodiment 142

(Z)-1-(4-(N-(3-bromo-4-fluorophenyl)-N'-hydroxyaminoiminomethyl)-1,2,5-oxadiazole-3-substituted)-3-(4-aminophenyl)guanidine

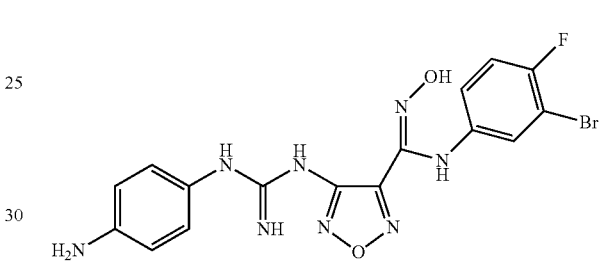

The synthesis method was the same as that in Embodiment 1.

$^1$H NMR (400 MHz, DMSO): δ 11.35 (s, 1H), 9.04 (s, 1H), 8.76 (s, 1H), 7.12 (t, J=8.8 Hz, 1H), 7.03 (m, 1H), 6.71 (m, 1H), 6.21 (s, 1H) ppm. $^{13}$C NMR (125 MHz, DMSO): δ 162.8, 157.5, 153.5, 150.0, 148.1, 138.9, 133.2, 130.1, 120.0, 119.1, 119.0, 118.2, 114.1, 113.0 ppm. MS (EI, m/z): 405 (M$^+$+1).

Embodiment 143

(Z)-1-(4-(N-(3-bromo-4-fluorophenyl)-N'-hydroxyaminoiminomethyl)-1,2,5-oxadiazole-3-substituted)-3-(4-trifluorophenyl)guanidine

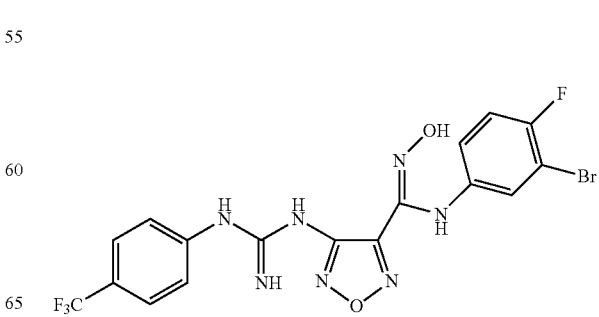

The synthesis method was the same as that in Embodiment 1.

¹H NMR (400 MHz, DMSO): δ 11.46 (s, 1H), 9.10 (s, 1H), 8.87 (s, 1H), 7.63 (d, J=6.6 Hz, 2H), 7.26 (d, J=6.6 Hz, 2H), 7.17 (t, J=8.8 Hz, 1H), 7.20-7.06 (m, 1H), 6.73-6.55 (m, 1H), 6.23 (s, 1H), 6.09 (s, 1H) ppm. ¹³C NMR (125 MHz, DMSO): δ 164.3, 160.1, 154.5, 151.6, 148.1, 140.8, 135.6, 121.9, 120.9, 119.6, 118.9, 115.9, 115.2 ppm. MS (EI, m/z): 503 (M⁺+1).

Embodiment 144

(Z)-1-(4-(N-(3-bromo-4-fluorophenyl)-N'-hydroxyaminoiminomethyl)-1,2,5-oxadiazole-3-substituted)-3-(2-fluoro-4-trimethoxyphenyl)guanidine

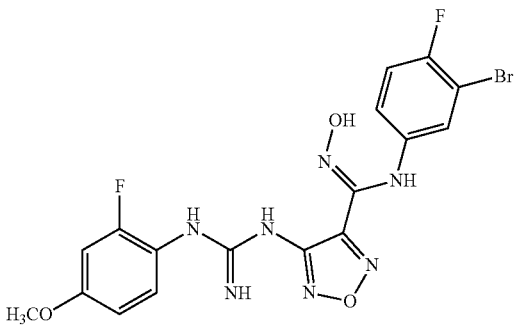 [SMILES: COc1ccc(NC(=N)Nc2nonc2/C(=N/O)Nc2ccc(F)c(Br)c2)c(F)c1]

The synthesis method was the same as that in Embodiment 1.

¹H NMR (400 MHz, DMSO): δ 11.43 (s, 1H), 9.05 (s, 1H), 8.85 (s, 1H), 7.56 (s, 1H), 7.25-7.21 (m, 2H), 7.20 (d, J=8.8 Hz, 1H), 7.11 (m, 1H), 6.76-6.51 (m, 1H), 6.21 (s, 1H), 6.10 (s, 1H), 3.75 (s, 3H) ppm. ¹³C NMR (125 MHz, DMSO): δ 163.3, 154.0, 150.9, 147.1, 140.1, 136.2, 134.5, 139.3, 120.6, 119.5, 119.3, 118.6, 114.2, 54.7 ppm. MS (EI, m/z): 483 (M⁺+1).

Embodiment 145

(Z)-1-(4-(N-(3-bromo-4-fluorophenyl)-N'-hydroxyaminoiminomethyl)-1,2,5-oxadiazole-3-substituted)-3-cyclohexylguanidine

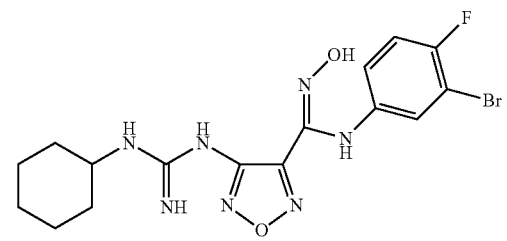 [SMILES: N=C(Nc1nonc1/C(=N/O)Nc1ccc(F)c(Br)c1)NC1CCCCC1]

The synthesis method was the same as that in Embodiment 1.

¹H NMR (400 MHz, DMSO): δ 11.41 (s, 1H), 9.01 (s, 1H), 8.83 (s, 1H), 7.16 (t, J=8.8 Hz, 1H), 7.10 (m, 1H), 6.78-6.73 (m, 1H), 6.24 (s, 1H), 3.58-3.52 (m, 1H), 1.85-1.81 (m, 2H), 1.63-1.59 (m, 2H), 1.46-1.19 (m, 6H) ppm. ¹³C NMR (125 MHz, DMSO): δ 163.0, 159.1, 154.2, 149.2, 145.6, 135.1, 134.5, 112.5, 107.3, 100.3, 52.1, 31.8, 25.6, 24.7 ppm. MS (EI, m/z): 441 (M⁺+1).

Embodiment 146

(Z)-1-(4-(N-(3-bromo-4-fluorophenyl)-N'-hydroxyaminoiminomethyl)-1,2,5-oxadiazole-3-substituted)-3-cyclopentylguanidine

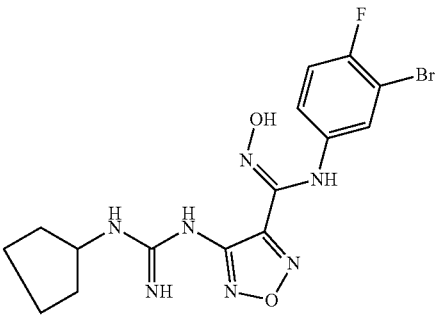 [SMILES: N=C(Nc1nonc1/C(=N/O)Nc1ccc(F)c(Br)c1)NC1CCCC1]

The synthesis method was the same as that in Embodiment 1.

¹H NMR (400 MHz, DMSO): δ 11.48 (s, 1H), 9.00 (s, 1H), 8.81 (s, 1H), 7.15 (t, J=8.8 Hz, 1H), 7.13-7.01 (m, 1H), 6.77-6.61 (m, 1H), 6.13 (s, 1H), 3.61-3.58 (m, 1H), 1.85-1.62 (m, 4H), 1.56-1.48 (m, 4H) ppm. ¹³C NMR (125 MHz, DMSO): δ 163.6, 158.1, 153.7, 148.1, 145.8, 135.2, 134.2, 112.1, 107.4, 101.1, 57.9, 32.3, 24.5 ppm. MS (EI, m/z): 427 (M⁺+1).

Embodiment 147

(Z)-1-(4-(N-(3-bromo-4-fluorophenyl)-N'-hydroxyaminoiminomethyl)-1,2,5-oxadiazole-3-substituted)-3-(4-hydroxycyclohexyl)guanidine

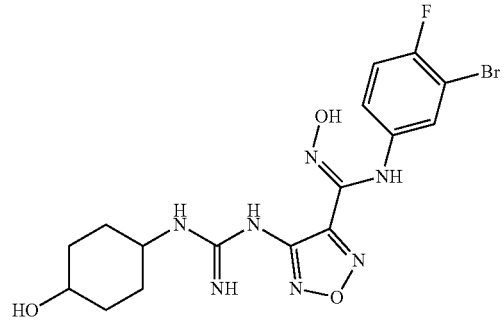 [SMILES: N=C(Nc1nonc1/C(=N/O)Nc1ccc(F)c(Br)c1)NC1CCC(O)CC1]

The synthesis method was the same as that in Embodiment 1.

¹H NMR (400 MHz, DMSO): δ 11.51 (s, 1H), 9.05 (s, 1H), 8.87 (s, 1H), 7.16 (t, J=8.8 Hz, 1H), 7.13-7.06 (m, 1H), 6.84-6.73 (m, 1H), 6.26 (s, 1H), 3.57-3.53 (m, 1H), 3.39 (m, 1H), 1.85-1.82 (m, 2H), 1.68-1.56 (m, 2H), 1.48-1.23 (m, 5H) ppm. ¹³C NMR (125 MHz, DMSO): δ 163.9, 159.1, 153.6, 149.3, 145.2, 135.1, 133.8, 112.7, 107.3, 100.6, 53.4, 51.8, 33.8, 32.5, 31.3 ppm. MS (EI, m/z): 412 (M⁺+1).

Embodiment 148

(Z)-1-(4-(N-(3-bromo-4-fluorophenyl)-N'-hydroxyaminoiminomethyl)-1,2,5-oxadiazole-3-substituted)-3-(piperidine-4-substituted)guanidine

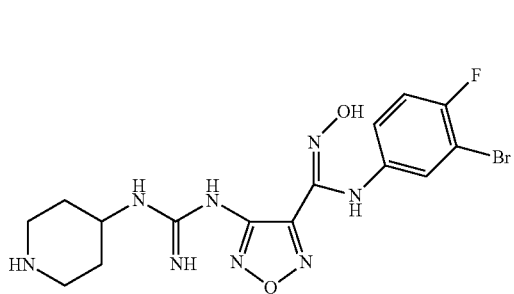 [SMILES: N=C(Nc1nonc1/C(=N/O)Nc1ccc(F)c(Br)c1)NC1CCNCC1]

The synthesis method was the same as that in Embodiment 1.

$^1$H NMR (400 MHz, DMSO): δ 11.48 (s, 1H), 9.02 (s, 1H), 8.82 (s, 1H), 7.16 (t, J=8.8 Hz, 1H), 7.10 (m, 1H), 6.84 (m, 1H), 6.27 (s, 1H), 3.55 (m, 1H), 2.79-2.69 (m, 4H), 1.68-1.54 (m, 4H) ppm. $^{13}$C NMR (125 MHz, DMSO): δ 163.2, 159.4, 154.3, 149.2, 145.6, 135.2, 134.7, 112.6, 107.4, 100.5, 51.7, 42.5, 32.0 ppm. MS (EI, m/z): 442 (M$^+$+1).

Embodiment 149

(Z)-1-(4-(N-(3-bromo-4-fluorophenyl)-N'-hydroxyaminoiminomethyl)-1,2,5-oxadiazole-3-substituted)-3-(cyclopropyl)guanidine

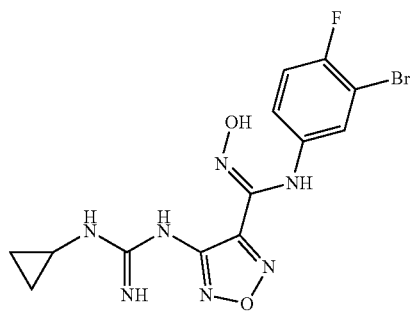 [SMILES: N=C(Nc1nonc1/C(=N/O)Nc1ccc(F)c(Br)c1)NC1CC1]

The synthesis method was the same as that in Embodiment 1.

$^1$H NMR (400 MHz, DMSO): δ 11.49 (s, 1H), 8.98 (s, 1H), 8.79 (s, 1H), 7.14 (t, J=8.8 Hz, 1H), 7.13-7.01 (m, 1H), 6.76-6.59 (m, 1H), 6.12 (s, 1H), 3.33 (m, 1H), 1.25-1.03 (m, 4H) ppm. $^{13}$C NMR (125 MHz, DMSO): δ 163.1, 159.8, 153.5, 148.0, 145.4, 135.0, 134.1, 112.2, 107.1, 100.8, 38.2, 11.1 ppm. MS (EI, m/z): 399 (M$^+$+1).

Embodiment 150

(Z)-1-(4-(N-(3-bromo-4-fluorophenyl)-N'-hydroxyaminoiminomethyl)-1,2,5-oxadiazole-3-substituted)-3-(4-aminocyclohexyl)guanidine

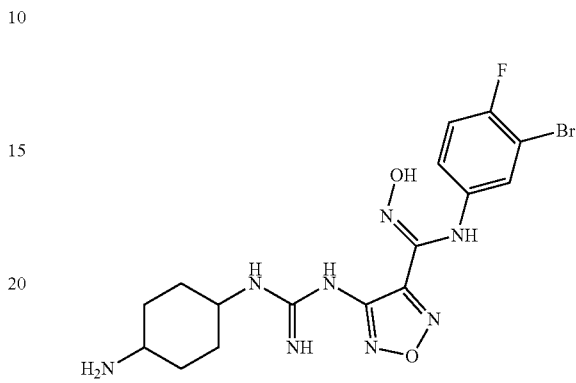

The synthesis method was the same as that in Embodiment 1.

$^1$H NMR (400 MHz, DMSO): δ 11.45 (s, 1H), 9.03 (s, 1H), 8.83 (s, 1H), 7.13 (t, J=8.8 Hz, 1H), 7.15-7.08 (m, 1H), 6.82-6.70 (m, 1H), 6.23 (s, 1H), 3.56-3.50 (m, 1H), 2.87 (m, 1H), 1.83-1.81 (m, 2H), 1.65-1.55 (m, 2H), 1.48-1.21 (m, 5H) ppm. $^{13}$C NMR (125 MHz, DMSO): δ 163.2, 159.0, 153.4, 149.0, 145.1, 134.8, 133.7, 112.4, 107.0, 100.3, 53.1, 33.7, 32.1, 31.2 ppm. MS (EI, m/z): 411 (M$^+$+1).

Embodiment 151

(Z)-1-(4-(N-(3-bromo-4-fluorophenyl)-N'-hydroxyaminoiminomethyl)-1,2,5-oxadiazole-3-substituted)-3-(3-hydroxypropyl)guanidine

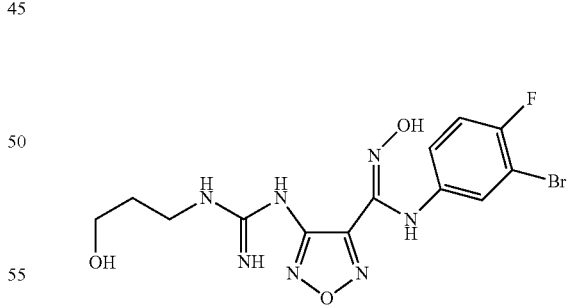

The synthesis method was the same as that in Embodiment 1.

$^1$H NMR (400 MHz, DMSO): δ 11.50 (s, 1H), 9.05 (s, 1H), 8.82 (s, 1H), 7.16 (t, J=8.8 Hz, 1H), 7.10 (m, 1H), 6.82 (m, 1H), 6.26 (s, 1H), 3.56 (t, J=6.8 Hz, 2H), 3.13 (t, J=6.6 Hz, 2H), 1.79 (m, 2H) ppm. $^{13}$C NMR (125 MHz, DMSO): 5163.2, 159.1, 154.3, 149.1, 145.3, 135.1, 134.6, 112.5, 107.3, 100.4, 59.8, 39.3, 31.5 ppm. MS (EI, m/z): 417 (M$^+$+1).

Embodiment 152

(Z)-1-(4-(N-(3-bromo-4-fluorophenyl)-N'-hydroxyaminoiminomethyl)-1,2,5-oxadiazole-3-substituted)-3-(2-hydroxyethyl)guanidine

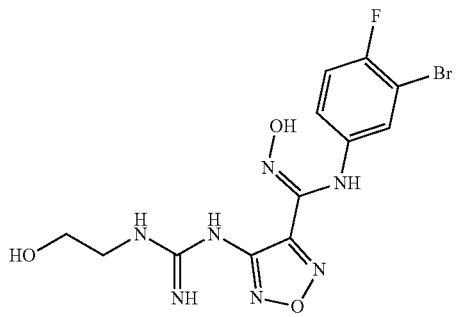 [SMILES: N=C(NCCO)Nc1nonc1/C(=N/O)Nc1ccc(F)c(Br)c1]

The synthesis method was the same as that in Embodiment 1.

$^1$H NMR (400 MHz, DMSO): δ 11.53 (s, 1H), 9.08 (s, 1H), 8.84 (s, 1H), 7.18 (t, J=8.8 Hz, 1H), 7.12 (m, 1H), 6.84 (m, 1H), 6.28 (s, 1H), 3.79 (t, J=6.8 Hz, 2H), 2.87 (t, J=6.6 Hz, 2H), ppm. $^{13}$C NMR (125 MHz, DMSO): 5163.2, 159.3, 154.5, 149.3, 145.5, 135.3, 134.8, 112.7, 107.5, 100.6, 59.9, 39.6, 31.8 ppm. MS (EI, m/z): 403 (M$^+$+1).

Embodiment 153

(Z)-1-(4-(N-(3-bromo-4-fluorophenyl)-N'-hydroxyaminoiminomethyl)-1,2,5-oxadiazole-3-substituted)-3-(2-hydroxyethyl)guanidine

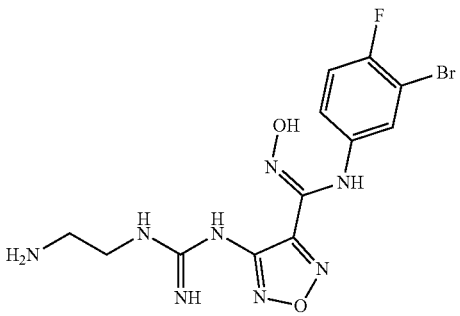 [SMILES: N=C(NCCN)Nc1nonc1/C(=N/O)Nc1ccc(F)c(Br)c1]

The synthesis method was the same as that in Embodiment 1.

$^1$H NMR (400 MHz, DMSO): δ 11.47 (s, 1H), 9.05 (s, 1H), 8.80 (s, 1H), 7.11 (t, J=8.8 Hz, 1H), 7.04 (m, 1H), 6.80 (m, 1H), 6.22 (s, 1H), 3.35 (t, J=6.8 Hz, 2H), 2.86 (t, J=6.8 Hz, 2H) ppm. $^{13}$C NMR (125 MHz, DMSO): δ 163.1, 159.0, 153.9, 148.8, 145.1, 134.9, 134.1, 112.2, 106.9, 100.0, 43.6, 39.5, ppm. MS (EI, m/z): 402 (M$^+$+1).

Embodiment 154

(Z)-1-(4-(N-(3-chloro-4-fluorophenyl)-N'-hydroxyaminoiminomethyl)-isoxazole-3-substituted)-4-(4-methoxyphenyl)guanidine

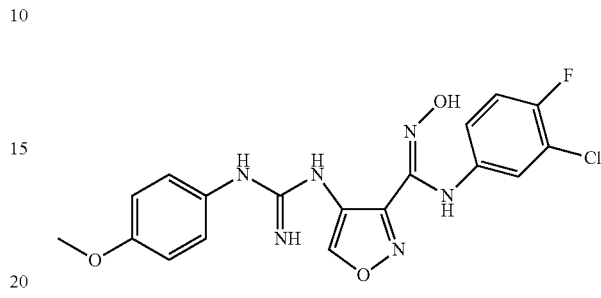

The synthesis method was the same as that in Embodiment 1.

$^1$H NMR (400 MHz, DMSO): δ 10.27 (s, 1H), 8.96 (s, 1H), 8.753 (s, 1H), 7.50 (d, J=7.2 Hz, 2H), 7.47 (s, 1H), 6.76 (d, J=7.2 Hz, 2H), 6.72 (s, 1H), 6.60 (d, J=6.8 Hz, 1H), 6.39 (d, J=6.8 Hz, 1H), 6.12 (s, 1H), 3.73 (s, 3H) ppm. $^{13}$C NMR (125 MHz, DMSO): δ 163.0, 156.2, 152.7, 152.0, 150.0, 145.8, 140.9, 138.4, 134.0, 131.1, 128.1, 122.5, 120.2, 120.0, 118.5, 118.0, 115.0, 114.4, 57.7 ppm. MS (EI, m/z): 419 (M$^+$+1).

Embodiment 155

(Z)-1-(4-(N-(3-chloro-4-fluorophenyl)-N'-hydroxyaminoiminomethyl)-isoxazole-3-substituted)-4-phenylguanidine

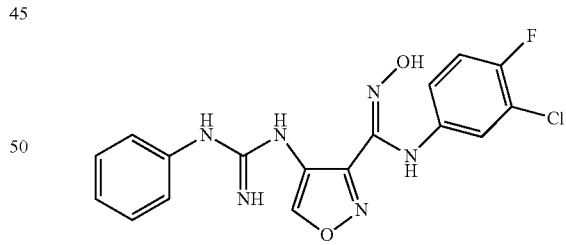

The synthesis method was the same as that in Embodiment 1.

$^1$H NMR (400 MHz, DMSO): δ 10.26 (s, 1H), 8.97 (s, 1H), 8.73 (s, 1H), 7.47 (s, 1H), 7.42-7.21 (m, 5H), 6.70 (s, 1H), 6.61 (d, J=6.8 Hz, 1H), 6.39 (d, J=6.8 Hz, 1H), 6.09 (s, 1H) ppm. $^{13}$C NMR (125 MHz, DMSO): δ 162.9, 152.5, 152.0, 149.9, 146.0, 140.8, 138.2, 135.5, 134.0, 131.1, 128.9, 124.2, 121.3, 120.2, 118.2, 117.9, 115.1 ppm. MS (EI, m/z): 389 (M$^+$+1).

Embodiment 156

(Z)-1-(4-(N-(3-chloro-4-fluorophenyl)-N'-hydroxyaminoiminomethyl)-isoxazole-3-substituted)-4-cyclohexylguanidine

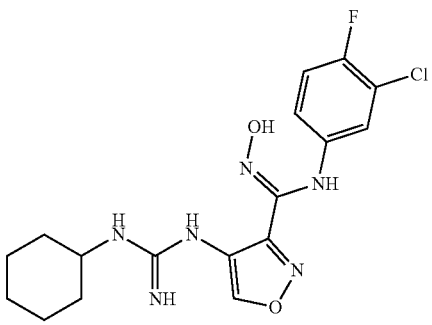 [SMILES: N=C(Nc1conc1/C(=N/O)Nc1ccc(F)c(Cl)c1)NC1CCCCC1]

The synthesis method was the same as that in Embodiment 1.

¹H NMR (400 MHz, DMSO): δ 10.23 (s, 1H), 8.95 (s, 1H), 8.72 (s, 1H), 7.46 (s, 1H), 6.72 (s, 1H), 6.61 (d, J=6.8 Hz, 1H), 6.40 (d, J=6.8 Hz, 1H), 6.11 (s, 1H), 3.53 (m, 1H), 1.79-1.55 (m, 4H), 1.49-1.38 (m, 6H) ppm.

¹³C NMR (125 MHz, DMSO): δ 163.0, 152.7, 152.0, 150.1, 145.9, 141.1, 138.4, 134.1, 131.1, 120.2, 118.5, 118.0, 115.0, 49.7, 33.5, 28.0, 22.5 ppm. MS (EI, m/z): 395 (M$^+$+1).

Embodiment 157

(Z)-1-(4-(N-(3-bromo-4-fluorophenyl)-N'-hydroxyaminoiminomethyl)-isoxazole-3-substituted)-3-(4-methoxyphenyl)guanidine

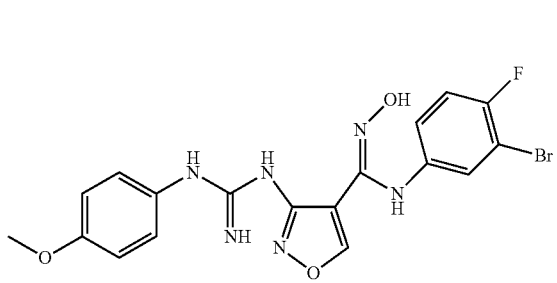 [SMILES: COc1ccc(NC(=N)Nc2nocc2/C(=N/O)Nc2ccc(F)c(Br)c2)cc1]

The synthesis method was the same as that in Embodiment 1.

¹H NMR (400 MHz, DMSO): δ 10.27 (s, 1H), 8.97 (s, 1H), 8.74 (s, 1H), 7.52 (d, J=7.2 Hz, 2H), 7.47 (s, 1H), 6.76 (d, J=7.2 Hz, 2H), 6.72 (s, 1H), 6.61 (d, J=6.8 Hz, 1H), 6.40 (d, J=6.8 Hz, 1H), 6.11 (s, 1H), 3.73 (s, 3H) ppm. ¹³C NMR (125 MHz, DMSO): δ 163.1, 156.2, 152.7, 152.1, 150.0, 145.9, 141.0, 138.4, 134.0, 131.2, 128.1, 122.5, 120.2, 118.5, 117.9, 115.0, 114.5, 57.7 ppm. MS (EI, m/z): 464 (M$^+$+1).

Embodiment 158

(Z)-1-(4-(N-(3-bromo-4-fluorophenyl)-N'-hydroxyaminoiminomethyl)-isoxazole-3-substituted)-3-phenylguanidine

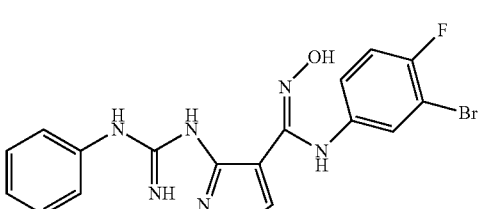

The synthesis method was the same as that in Embodiment 1.

¹H NMR (400 MHz, DMSO): δ 10.26 (s, 1H), 8.95 (s, 1H), 8.74 (s, 1H), 7.47 (s, 1H), 7.42-7.22 (m, 5H), 6.72 (s, 1H), 6.61 (d, J=6.8 Hz, 1H), 6.40 (d, J=6.8 Hz, 1H), 6.11 (s, 1H) ppm. ¹³C NMR (125 MHz, DMSO): δ 163.0, 152.7, 152.1, 149.9, 145.8, 141.0, 138.4, 135.8, 134.0, 131.1, 128.8, 124.3, 121.5, 120.2, 118.5, 117.8, 115.0 ppm. MS (EI, m/z): 434 (M$^+$+1).

Embodiment 159

(Z)-1-(4-(N-(3-bromo-4-fluorophenyl)-N'-hydroxyaminoiminomethyl)-isoxazole-3-substituted)-3-cyclohexylguanidine

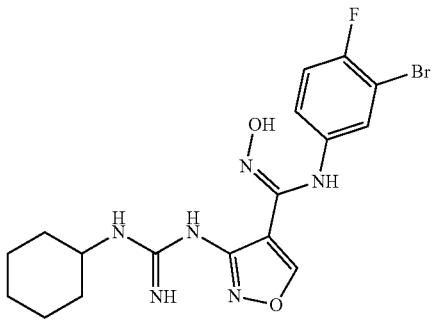 [SMILES: N=C(Nc1nocc1/C(=N/O)Nc1ccc(F)c(Br)c1)NC1CCCCC1]

The synthesis method was the same as that in Embodiment 1.

¹H NMR (400 MHz, DMSO): δ 10.27 (s, 1H), 8.92 (s, 1H), 8.73 (s, 1H), 7.47 (s, 1H), 6.72 (s, 1H), 6.62 (d, J=6.8 Hz, 1H), 6.40 (d, J=6.8 Hz, 1H), 6.12 (s, 1H), 3.52 (m, 1H), 1.79-1.55 (m, 4H), 1.49-1.38 (m, 6H) ppm. ¹³C NMR (125 MHz, DMSO): δ 162.9, 152.7, 152.1, 150.0, 145.8, 141.0, 138.3, 133.9, 131.1, 120.2, 119.9, 118.5, 117.8, 115.0, 49.5, 33.2, 27.9, 22.4 ppm. MS (EI, m/z): 440 (M$^+$+1).

Embodiment 160

(Z)-1-(4-(N-(3-bromo-4-fluorophenyl)-N'-hydroxyaminoiminomethyl)-furan-3-substituted)-3-(4-methoxyphenyl)guanidine

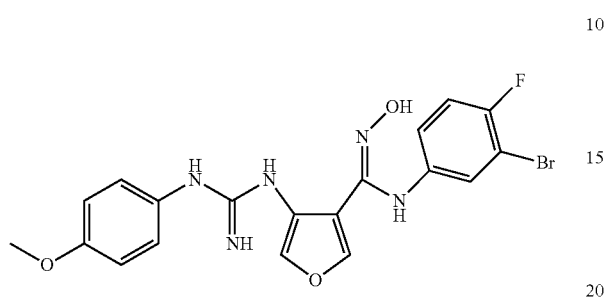

The synthesis method was the same as that in Embodiment 1.

$^1$H NMR (400 MHz, DMSO): δ 10.32 (s, 1H), 8.94 (s, 1H), 8.79 (s, 1H), 7.52 (d, J=8.6 Hz, 2H), 7.43 (s, 1H), 7.40 (s, 1H), 6.85 (d, J=8.6 Hz, 2H), 6.73 (s, 1H), 6.62 (d, J=8.0 Hz, 1H), 6.42 (d, J=8.0 Hz, 1H), 6.15 (s, 1H), 3.73 (s, 3H) ppm. $^{13}$C NMR (125 MHz, DMSO): δ 163.1, 152.0, 149.8, 146.0, 142.6, 141.6, 141.3, 138.9, 134.2, 131.7, 120.5, 120.0, 118.6, 118.3, 115.5, 55.8 ppm. MS (EI, m/z): 463 (M$^+$+1).

Embodiment 161

(Z)-1-(4-(N-(3-bromo-4-fluorophenyl)-N'-hydroxyaminoiminomethyl)-furan-3-substituted)-3-phenylguanidine

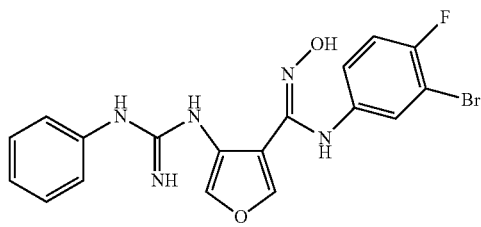 [SMILES: N=C(Nc1ccccc1)Nc1cocc1/C(=N/O)Nc1ccc(F)c(Br)c1]

The synthesis method was the same as that in Embodiment 1.

$^1$H NMR (400 MHz, DMSO): δ 10.29 (s, 1H), 8.95 (s, 1H), 8.77 (s, 1H), 7.60-7.27 (m, 5H), 7.41 (s, 1H), 7.38 (s, 1H), 6.76 (s, 1H), 6.68 (d, J=6.8 Hz, 1H), 6.48 (d, J=6.8 Hz, 1H), 6.15 (s, 1H) ppm. $^{13}$C NMR (125 MHz, DMSO): δ 163.2, 152.0, 150.0, 145.8, 142.6, 141.4, 140.9, 138.8, 134.0, 131.2, 120.1, 118.5, 118.0, 115.1 ppm. MS (EI, m/z): 433 (M$^+$+1).

Embodiment 162

(Z)-1-(4-(N-(3-bromo-4-fluorophenyl)-N'-hydroxyaminoiminomethyl)-furan-3-substituted)-3-cyclohexylguanidine

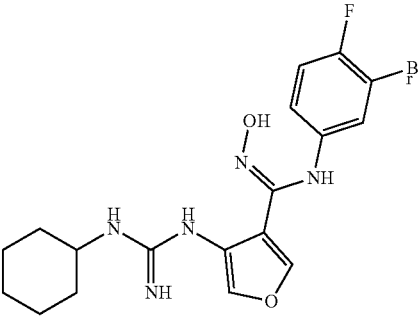 [SMILES: N=C(Nc1cocc1/C(=N/O)Nc1ccc(F)c(Br)c1)NC1CCCCC1]

The synthesis method was the same as that in Embodiment 1.

$^1$H NMR (400 MHz, DMSO): δ 10.28 (s, 1H), 8.93 (s, 1H), 8.75 (s, 1H), 7.40 (s, 1H), 7.38 (s, 1H), 6.75 (s, 1H), 6.65 (d, J=6.8 Hz, 1H), 6.43 (d, J=6.8 Hz, 1H), 6.11 (s, 1H), 1.83-1.78 (m, 2H), 1.63-1.56 (m, 2H), 1.42-1.18 (m, 6H) ppm. $^{13}$C NMR (125 MHz, DMSO): δ 163.1, 152.0, 149.8, 146.1, 142.5, 141.4, 140.8, 138.7, 133.8, 131.2, 120.3, 118.5, 118.0, 115.1, 49.4, 33.5, 28.0, 22.4 ppm. MS (EI, m/z): 439 (M$^+$+1).

Example 156 Determination of in vitro biochemical activity (1) Method for Determining Biochemical Activity of IDO1 Enzyme Firstly, 15 μl of buffer solution of sodium hydrogen phosphate (PH:7-8), 5 μl of reaction buffer solution containing a proper amount of IDO-1 enzyme and heterocyclic urea compound prepared by the invention were added into wells of a microplate, mixed evenly, and reacted at room temperature for 3 hours; then a light absorption value at 320 nm wavelength was detected by using Envision Multilabel Reader of PE company, an inhibition rate of the heterocyclic urea compound on the enzyme reaction was calculated according to an absorption ratio, and an IC50 value of the heterocyclic urea compound was calculated through analysis by GraphPad.

(2) Method for Determining Cell Activity

Hela cells were cultured and passaged in a DMEM medium supplemented with antibiotics in a 37° C. CO$_2$ incubator, inoculated into a 96-well plate for overnight culture, then 1 μl of heterocyclic urea compound with appropriate concentration was added to each well, and then 100 μl of interferon γ (final concentration was 100 ng/ml) was added. After the cells were continuously cultured for 72 hours, 70 μl of cell culture supernatant was added to a 96-well V-bottom plate, 5 μl of trichloroacetic acid (6.1 N) was added to each well, incubated at 50° C. for 30 min, then taken out and centrifuged at 25000 rpm for 10 min. The above centrifuged supernatant was transferred to a 384-well microplate (20 μl/well), then 20 μl of 2% didimethylamino-benzaldehyde acetic acid solution was added to each well, shaken and mixed evenly, then photometric absorption was performed at 480 nm, and values were measured.

The determination results of IDO1 enzyme inhibitory activity and cell inhibitory activity of each heterocyclic urea compound are shown in Table 1.

C: IC$_{50}$>1 μM; B: IC$_{50}$=100 nM-1 μM; A: IC$_{50}$<1 nM;

TABLE 1

Determination results of IDO1 enzyme and cell inhibitory activity

| Urea compounds prepared in the embodiments | IDO1 (IC$_{50}$ μM) | Hela (IC$_{50}$ μM) |
|---|---|---|
| Embodiment 1 | B | B |
| Embodiment 2 | B | B |
| Embodiment 3 | C | C |
| Embodiment 4 | C | C |
| Embodiment 5 | C | C |
| Embodiment 6 | C | C |
| Embodiment 7 | B | B |
| Embodiment 8 | B | B |
| Embodiment 9 | C | C |
| Embodiment 10 | A | A |
| Embodiment 11 | A | A |
| Embodiment 12 | B | B |
| Embodiment 13 | A | A |
| Embodiment 14 | A | A |
| Embodiment 15 | A | A |
| Embodiment 16 | B | B |
| Embodiment 17 | A | A |
| Embodiment 18 | A | A |
| Embodiment 19 | B | B |
| Embodiment 20 | B | B |
| Embodiment 21 | B | B |
| Embodiment 22 | B | B |
| Embodiment 23 | A | A |
| Embodiment 24 | A | A |
| Embodiment 25 | B | B |
| Embodiment 26 | A | A |
| Embodiment 27 | A | A |
| Embodiment 28 | A | A |
| Embodiment 29 | A | A |
| Embodiment 30 | A | A |
| Embodiment 31 | B | B |
| Embodiment 32 | B | B |
| Embodiment 33 | B | B |
| Embodiment 34 | B | B |
| Embodiment 35 | B | B |
| Embodiment 36 | B | B |
| Embodiment 37 | B | B |
| Embodiment 38 | B | B |
| Embodiment 39 | B | B |
| Embodiment 40 | B | B |
| Embodiment 41 | B | B |
| Embodiment 42 | C | C |
| Embodiment 43 | C | C |
| Embodiment 44 | C | C |
| Embodiment 45 | C | C |
| Embodiment 46 | C | C |
| Embodiment 47 | B | B |
| Embodiment 48 | B | B |
| Embodiment 49 | B | B |
| Embodiment 50 | B | B |
| Embodiment 51 | B | B |
| Embodiment 52 | B | B |
| Embodiment 53 | B | B |
| Embodiment 54 | B | B |
| Embodiment 55 | A | A |
| Embodiment 56 | A | A |
| Embodiment 57 | C | C |
| Embodiment 58 | B | B |
| Embodiment 59 | C | C |
| Embodiment 60 | C | C |
| Embodiment 61 | B | B |
| Embodiment 62 | B | B |
| Embodiment 63 | A | A |
| Embodiment 64 | B | B |
| Embodiment 65 | B | B |
| Embodiment 66 | B | B |
| Embodiment 67 | B | B |
| Embodiment 68 | B | B |
| Embodiment 69 | B | B |
| Embodiment 70 | B | B |
| Embodiment 71 | B | B |
| Embodiment 72 | B | B |
| Embodiment 73 | B | B |
| Embodiment 74 | B | B |
| Embodiment 75 | B | B |
| Embodiment 76 | C | C |
| Embodiment 77 | C | C |
| Embodiment 78 | C | C |
| Embodiment 79 | B | B |
| Embodiment 80 | C | C |
| Embodiment 81 | B | B |
| Embodiment 82 | B | B |
| Embodiment 83 | C | C |
| Embodiment 84 | B | B |
| Embodiment 85 | A | A |
| Embodiment 86 | C | C |
| Embodiment 87 | A | A |
| Embodiment 88 | A | A |
| Embodiment 89 | A | A |
| Embodiment 90 | A | A |
| Embodiment 91 | B | B |
| Embodiment 92 | B | B |
| Embodiment 93 | A | A |
| Embodiment 94 | B | B |
| Embodiment 95 | B | B |
| Embodiment 96 | B | B |
| Embodiment 97 | B | B |
| Embodiment 98 | B | B |
| Embodiment 99 | B | B |
| Embodiment 100 | B | B |
| Embodiment 101 | B | B |
| Embodiment 102 | B | B |
| Embodiment 103 | B | B |
| Embodiment 104 | C | C |
| Embodiment 105 | A | A |
| Embodiment 106 | A | A |
| Embodiment 107 | C | C |
| Embodiment 108 | B | B |
| Embodiment 109 | A | A |
| Embodiment 110 | A | A |
| Embodiment 111 | A | A |
| Embodiment 112 | B | B |
| Embodiment 113 | B | B |
| Embodiment 114 | A | A |
| Embodiment 115 | B | B |
| Embodiment 116 | B | B |
| Embodiment 117 | A | A |
| Embodiment 118 | A | A |
| Embodiment 119 | C | C |
| Embodiment 120 | C | C |
| Embodiment 121 | B | B |
| Embodiment 122 | C | C |
| Embodiment 123 | A | A |
| Embodiment 124 | A | A |
| Embodiment 125 | C | C |
| Embodiment 126 | B | B |
| Embodiment 127 | A | A |
| Embodiment 128 | A | A |
| Embodiment 129 | B | B |
| Embodiment 130 | B | B |
| Embodiment 131 | B | B |
| Embodiment 132 | B | B |
| Embodiment 133 | B | B |
| Embodiment 134 | B | B |
| Embodiment 135 | B | B |
| Embodiment 136 | C | C |
| Embodiment 137 | B | B |
| Embodiment 138 | B | B |
| Embodiment 139 | A | A |
| Embodiment 140 | B | B |
| Embodiment 141 | A | A |
| Embodiment 142 | A | A |
| Embodiment 143 | C | C |
| Embodiment 144 | B | B |

TABLE 1-continued

Determination results of IDO1 enzyme and cell inhibitory activity

| Urea compounds prepared in the embodiments | IDO1 (IC$_{50}$ μM) | Hela (IC$_{50}$ μM) |
|---|---|---|
| Embodiment 145 | A | A |
| Embodiment 146 | C | C |
| Embodiment 147 | A | A |
| Embodiment 148 | A | A |
| Embodiment 149 | C | C |
| Embodiment 150 | B | B |
| Embodiment 151 | A | A |
| Embodiment 152 | A | A |
| Embodiment 153 | A | A |
| Embodiment 154 | B | B |
| Embodiment 155 | B | B |
| Embodiment 156 | B | B |
| Embodiment 157 | B | B |
| Embodiment 158 | B | B |
| Embodiment 159 | B | B |
| Embodiment 160 | B | B |
| Embodiment 161 | B | B |
| Embodiment 162 | B | B |
| INCB24360 | B | B |

IC$_{50}$ in Table 1 represents drug concentrations required for 50% growth inhibition of IDO1 enzyme and cell.

From the results in Table 1, it can be seen that the heterocyclic urea compounds prepared by the present invention have significantly inhibited the activity of the listed IDO1 enzyme and the activity of the IDO1 enzyme in the Hela cell in comparison with the positive control (INCB24360).

The heterocyclic urea compounds and the pharmaceutical compositions and applications thereof provided by the embodiments of the invention are described in detail above. Specific examples are applied to explain the principles and embodiments of the invention. The above embodiments are merely used to help understand the method of the invention and the core ideas thereof. Meanwhile, those skilled in the art may make changes in the specific implementations and application scopes according to the idea of the invention. To sum up, the contents of this description should not be construed as limiting the invention.

What is claimed is:

1. A heterocyclic urea compound having a chemical structure of general formula I, or a pharmaceutically acceptable salt, a stereoisomer, a racemate, a prodrug or a solvate thereof:

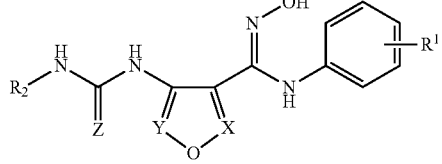

I wherein,
X is N or CH;
Y is N or CH;
Z is O, S, or NH;
R$^1$ represents a substituent on a benzene ring, and is selected from a group consisting of hydrogen, halogen, nitro, cyano, hydroxyl, amino, dimethylamino, C$_{1-6}$ alkyl, C$_{1-6}$ perfluoroalkyl, C$_{2-6}$ alkenyl, C$_{2-6}$ alkynyl, C$_{3-6}$ cycloalkyl, C$_{3-12}$ heterocyclyl and C$_{1-6}$ alkoxy; and R$_2$ group is selected from a group consisting of hydrogen, C$_1$-C$_{12}$ alkyl, —CH$_2$—O—CH$_2$—(C$_1$-C$_{12}$ alkyl), —CH$_2$—NH—CH$_2$—(C$_1$-C$_{12}$ alkyl), —CH$_2$—S—(C$_1$-C$_{12}$ alkyl), C$_7$-C$_{12}$ aryl, heteroaryl, —CH$_2$—(C$_7$-C$_{12}$ aryl), —CH$_2$-heteroaryl, C$_3$-C$_4$ cycloalkyl, C$_6$-C$_{12}$ cycloalkyl, C$_4$-C$_9$ heterocycloalkyl and —CH$_2$—NH—SO$_2$—NH$_2$.

2. The heterocyclic urea compound according to claim 1, wherein the C$_7$-C$_{12}$ aryl, the heteroaryl, the —CH$_2$—(C$_7$-C$_{12}$ aryl) and the —CH$_2$-heteroaryl contain one or more substituent(s) that is selected from a group consisting of halogen, amino, hydroxyl, nitro, cyano, C$_1$-C$_{12}$ alkyl, C$_1$-C$_{12}$ alkoxy, C$_1$-C$_{12}$ aminoalkyl, C$_1$-C$_{12}$ acyl, C$_1$-C$_{12}$ acyloxy, C$_1$-C$_{12}$ thioalkyl, carboxyl and phenyl; and the C$_6$-C$_{12}$ cycloalkyl contains one or more substituent(s) that is selected from a group consisting of halogen, amino, hydroxyl, nitro, cyano, C$_1$-C$_{12}$ alkyl, C$_1$-C$_{12}$ alkoxy, C$_1$-C$_{12}$ aminoalkyl, C$_1$-C$_{12}$ acyl, C$_1$-C$_{12}$ acyloxy, C$_1$-C$_{12}$ sulfonylalkyl, carboxyl and phenyl.

3. The heterocyclic urea compound according to claim 1, the heterocyclic urea compound is prepared by the following steps of:

(1) performing a chlorination reaction on a compound of formula II under an action of an acid and a chlorination reagent in an organic solvent to obtain a compound of formula III, a reaction process being as follows:

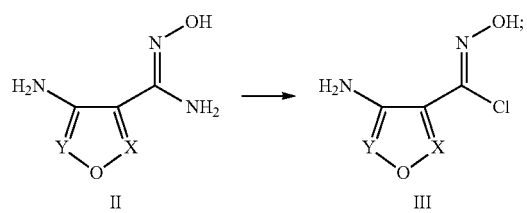

(2) reacting the compound of formula III with an aromatic amine under an action of an alkali in the organic solvent to obtain a compound of formula IV, a reaction process being as follows:

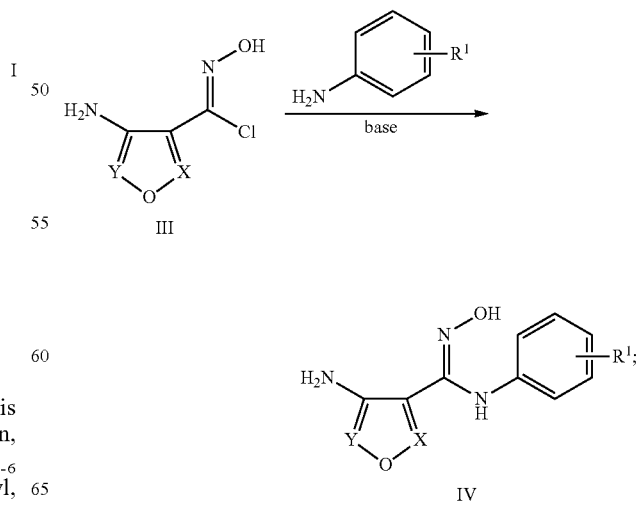

(3) reacting the compound of formula IV under an action of a CDI in the organic solvent to obtain a compound of formula V, a reaction process being as follows:

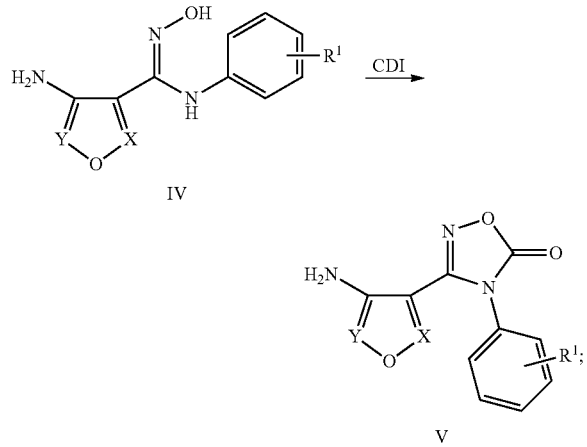

IV

V (4) reacting the compound of formula V with a compound of formula $R_2$—N=C=Z in the organic solvent to obtain a compound of formula VI, a reaction process being as follows:

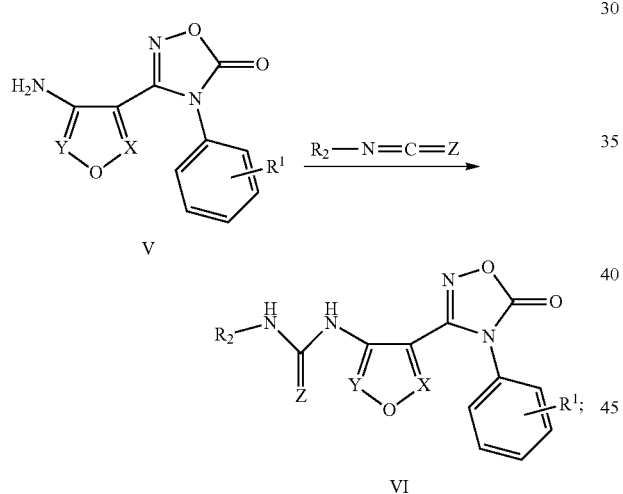

V

VI and (5) deprotecting the compound of formula VI under the action of the alkali to obtain a compound of formula I, a reaction process being as follows:

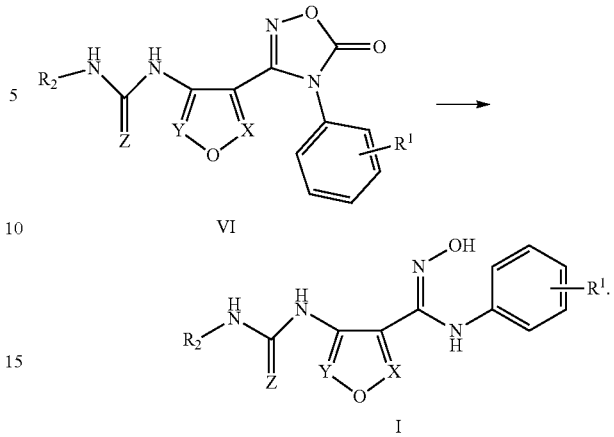

VI

I

4. The heterocyclic urea compound according to claim 3, wherein the organic solvent is one or more selected from a group consisting of dichloromethane, tetrahydrofuran, dimethylformamide, ethylene glycol dimethyl ether, 1,2-dichloroethane, dimethyl phthalate, methanol, ethanol, petroleum ether, n-hexane and diethyl ether;

the acid is one or more selected from a group consisting of acetic acid, trifluoroacetic acid, formic acid, propionic acid, sulfuric acid, nitric acid and hydrochloric acid;

the alkali is one or more selected from a group consisting of potassium carbonate, sodium carbonate, sodium bicarbonate, magnesium carbonate, calcium carbonate, cesium carbonate, sodium hydroxide, potassium hydroxide, lithium hydroxide, cesium hydroxide, magnesium hydroxide, imidazole hydroxide, triethylamine, diisopropylethylamine, piperidine, dimethylpyridine, N-methylmorpholine, DABCO and pyridine;

the $R^1$ group is selected from hydrogen, halogen, nitro, cyano, hydroxyl, amino, dimethylamino, $C_{1-6}$ alkyl, $C_{1-6}$ perfluoroalkyl, $C_{2-6}$ alkenyl, $C_{2-6}$ alkynyl, $C_{3-6}$ cycloalkyl, $C_{3-12}$ heterocyclyl and $C_{1-6}$ alkoxy; and the $R_2$ group is selected from a group consisting of $C_1$-$C_{12}$ alkyl, —$CH_2$—O—$CH_2$—($C_1$-$C_{12}$ alkyl), —$CH_2$—NH—$CH_2$—($C_1$-$C_{12}$ alkyl), —$CH_2$—S—($C_1$-$C_{12}$ alkyl), $C_7$-$C_{12}$ aryl, heteroaryl, —$CH_2$—($C_6$-$C_{12}$ aryl), —$CH_2$— heteroaryl, $C_3$-$C_9$ cycloalkyl and; $C_4$-$C_9$ heterocycloalkyl.

5. An anti-tumor drug composition, comprising the heterocyclic urea compound having a chemical structure of general formula I, or the pharmaceutically acceptable salt, the stereoisomer, the racemate, the prodrug or the solvate thereof according to claim 1, and a pharmaceutically acceptable vector.

* * * * *